United States Patent [19]

Farwell

[11] Patent Number: 5,406,956
[45] Date of Patent: Apr. 18, 1995

[54] METHOD AND APPARATUS FOR TRUTH DETECTION

[75] Inventor: Lawrence A. Farwell, Potomac, Md.

[73] Assignee: Francis Luca Conte, Swampscott, Mass.

[21] Appl. No.: 16,215

[22] Filed: Feb. 11, 1993

[51] Int. Cl.$^6$ ............................................ A61B 5/0484
[52] U.S. Cl. ..................................................... 128/731
[58] Field of Search ................................. 128/731–732

[56] References Cited

U.S. PATENT DOCUMENTS

| | | | |
|---|---|---|---|
| 3,998,213 | 12/1976 | Price | 128/664 |
| 4,537,198 | 8/1985 | Corbett | 128/644 X |
| 4,932,416 | 6/1990 | Rosenfeld | 128/731 |
| 4,941,477 | 7/1990 | Farwell | 128/731 |

(List continued on next page.)

OTHER PUBLICATIONS

Farwell, L. A. (1992) The Brain-Wave Information Detection (BID) System: A New Paradigm for Psychophysiological Detection of Information. Doctoral Dissertation, University of Illinois at Urbana-Champaign. pp: Cover, iii–vii, 1–165.

Farwell, L. A. (1992) Two New Twists on the Truth Detector: Brain-Wave Detection of Occupational Information, *Psychophysology* 29: 4A: S3. p. 20 Sep. 1992.

Farwell, L. A. and Donchin, E. (1986). The Brain Detector: P300 in the Detection of Deception. *Psychophysiology*, 24: 434. p. Cover, 434 Jul. 1986.

Farwell, L. A. and Donchin, E. (1991). The Truth Will Out: Interrogative Polygraphy ("Lie Detection") with Event-Related Brain Potentials. *Psychophysiology*, 28, 5: 531–47. Sep. 1991.

Farwell, L. A. and Donchin, E. (1988). Talking Off the Top of Your Head: Toward a Mental Prosthesis Utilizing Event-Related Brain Potentials. *Electroencephalography and Clinical Neurophysiology*, 70:510–523. Apr. 1988.

Farwell, L. A., Martinerie, J. M., Bashore, T. H., Rapp, P. E., and Goddard, P. H. (1993). Optimal Digital Filters for Long-Latency Components of the Event-Related Brain Potential. *Psychophysiology*, 30, 306–315. May 1993.

Johnson, M. and Rosenfeld, J. P. (1992). Oddball-Evoked P300-Based Method of Deception Detection in the Laboratory II: Utilization of Non-Selective Activation of Relevant Knowledge, *International Journal of Psychophysiology* 12:289–306 Feb. 1992.

Rapp, P. E., Albano, A. M., Schmah, T. I., and Farwell, L. A., Filtered Noise Can Mimic Low-Dimensional Chaotic Attractors, *Physical Review E*, 47, 4:2289–97 Apr. 1993.

Rosenfeld, J. P., Angell, A., Johnson, M., and Quan, J. (1991). An ERP-Based, Control-Question Lie Detector
(List continued on next page.)

*Primary Examiner*—Angela D. Sykes
*Attorney, Agent, or Firm*—Francis L. Conte

[57] ABSTRACT

A method of detecting information stored in the brain of a subject includes presenting to the subject in oddball series Probe, Target, and Irrelevant stimuli. The Probe stimuli are relevant to a situation under investigation; the Irrelevant stimuli are not; and the Target stimuli are identified to the subject as being noteworthy, and in response to which the subject is instructed to perform a task. The Target stimuli like the Probe stimuli are relevant to the situation under investigation. The method also includes detecting electrical brain responses for each of the stimuli; analyzing the responses for uncovering an event related brain potential; and comparing the Probe responses with the Target responses to determine whether the subject recognizes the Probes, and comparing the Probe responses with the Irrelevant responses to determine whether the subject does not recognize the Probes. Three exemplary headbands are disclosed for positioning electrodes at preferred locations on the subject's scalp for obtaining electrical responses therefrom.

31 Claims, 10 Drawing Sheets

U.S. PATENT DOCUMENTS 5,113,870  5/1992  Rosenfeld ............................ 128/731
5,137,027  8/1992  Rosenfeld ............................ 128/731
5,170,780  12/1992  Rosenfeld ............................ 128/731

OTHER PUBLICATIONS

Analog: Algorithms for Discriminating Effects Within Individual's Average Waveforms. *Psychophysiology*, 28, 3: 319–335. May 1991.

Rosenfled, J. P. and Kim, M. (1991). Ongoing Pain as a Mental Workload Indexed by P300 Depression: Discrimination of Real and Feigned Pain Conditions. *Psychophysiology 28, 3: 336–343 May 1991*.

Rosenfeld, J. P., Nasman, V. T., Whalen, R., Cantwell, B., and Mazzeri, L. (1987). Late Vertex Positivity in Event-Related Potentials as a Guilty Knowledge Indicator: A New Method of Lie Detection, *International Journal of Neuroscience*, 34: 125–129. Sep. 1987.

Sutter, E. (1983) An Oculo-Encephalographic Communication System. *Proc. 6th Annual Conf. of Rehabilitation Engineering*, 171–173. Sep., 1983.

Wasserman, S. and Bockenholt, U. (1989). Bootstrapping: Applications to Psychophysiology, *Psychophysiology* 26: 208–221. Mar. 1989.

Rosenfeld, J. P., Bhat, K., Miltenberger, A., and Johnson, M. (1992). Event-Related Potentials in the Dual-Task Paradigm: P300 Discriminates engaging and non-engaging films when film-viewing is the primary task. *International Journal of Psychophysiology*, 12:221–232, Nov., 1992.

Rosenfeld, J. P, Cantwell, B., Nasman, V. T., Wojdak, V., Ivanov, S., and Mazzeri L. (1988). A Modified, Event-Related Potential-Based Guilty Knowledge Test, *International Journal of Neuroscience*, 42: 157–61. Oct. 1987.

Fabiani et al; *Psychophysiology*, "The Reliability of Measurement of the P300 Component of the Event-Related Brain Potential"; vol. 23, No. 4, p. 434, Jul. 1986.

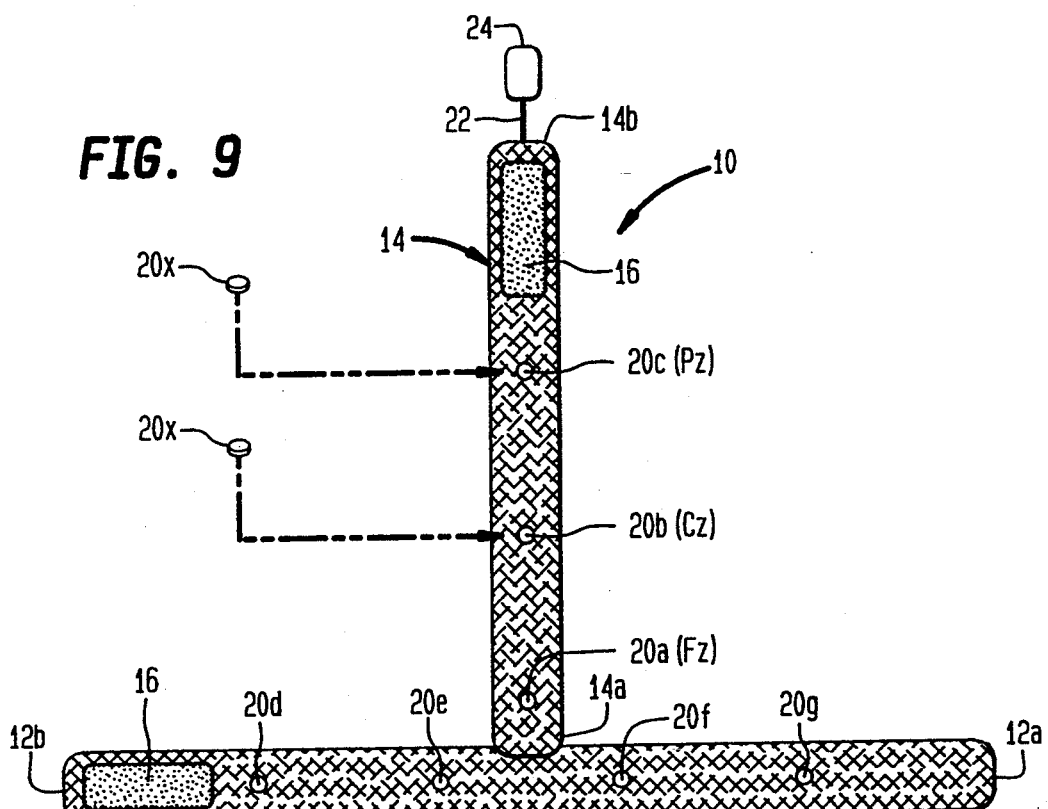
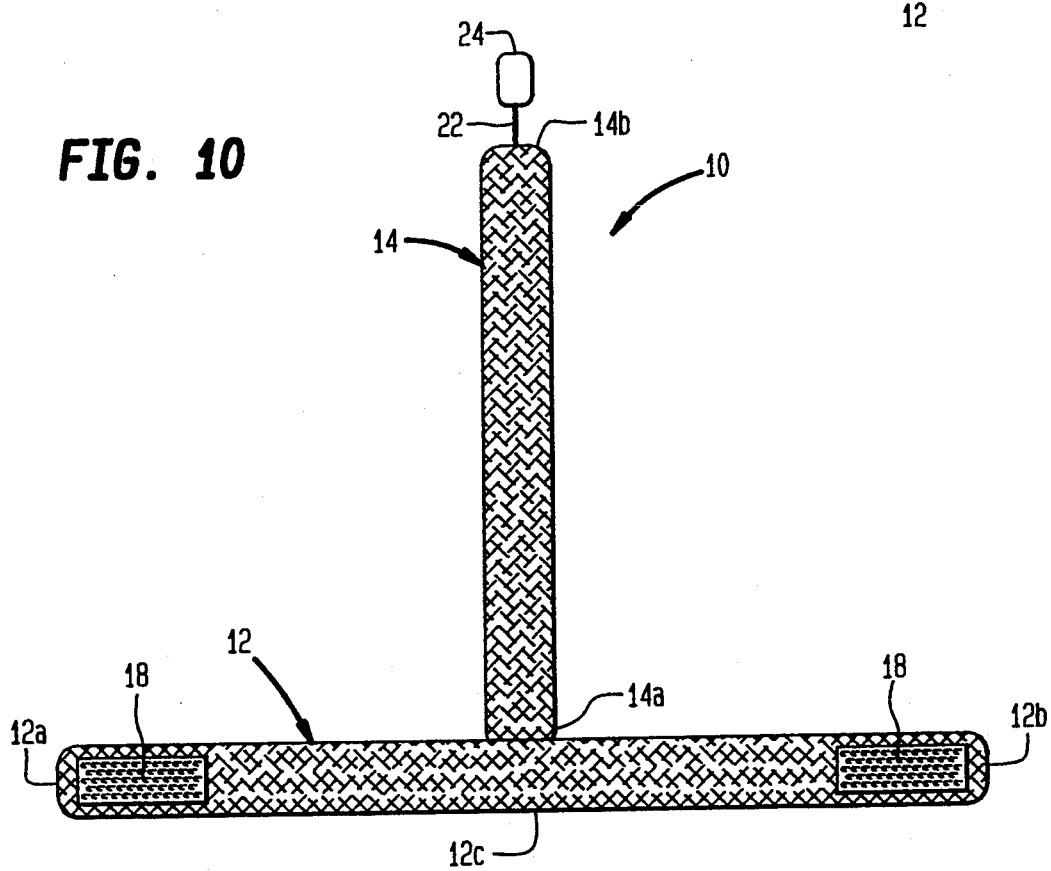

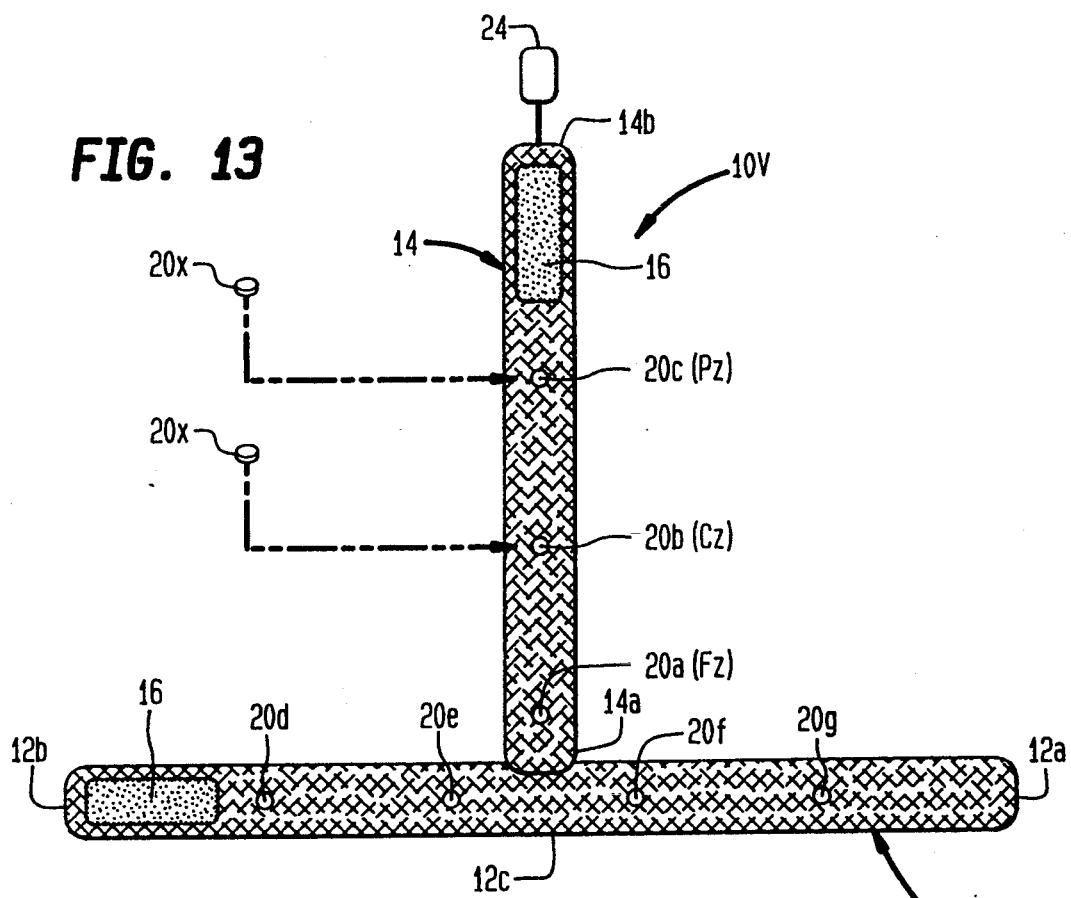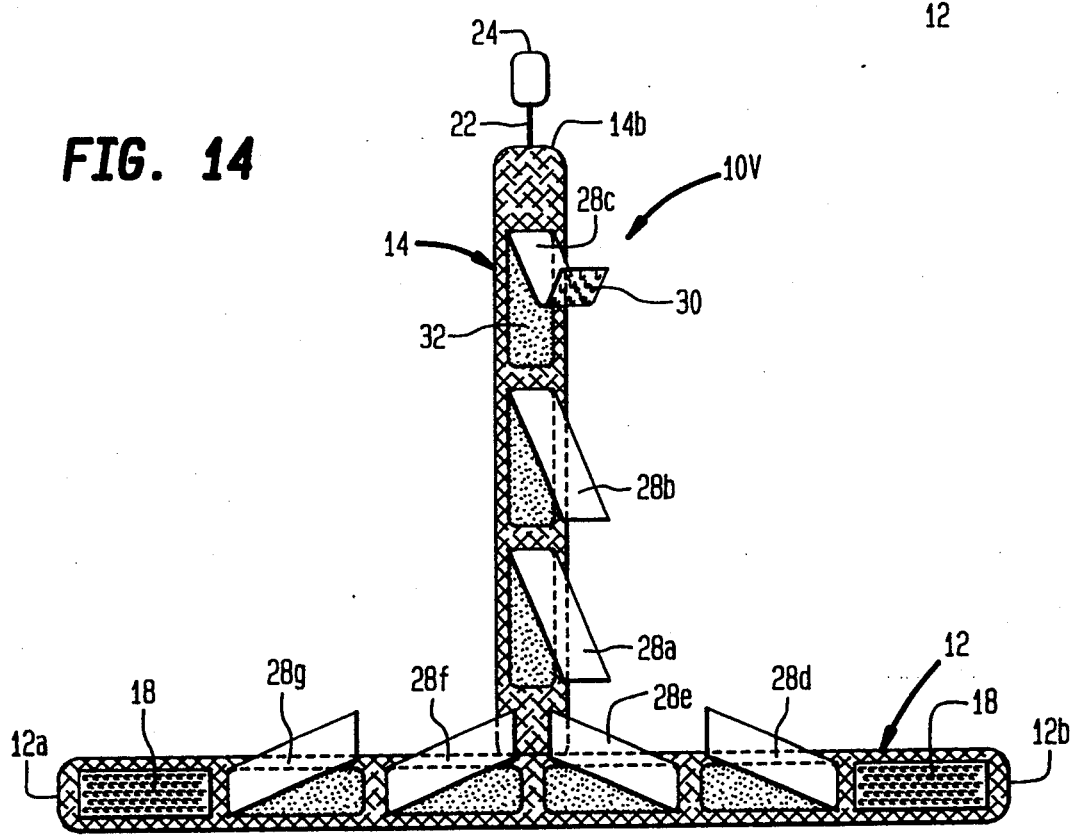

METHOD AND APPARATUS FOR TRUTH DETECTION

BACKGROUND OF THE INVENTION

The present invention relates generally to methods and apparatus for detecting concealed information based on human brain activity.

INTRODUCTION

Conventional Psychophysiological Detection of Concealed Information

Attempts to discover concealed information stored in the brain of another human being are as old as human history. The purpose of this report is to propose a new paradigm for the psychophysiological detection of concealed information, to test the new paradigm, to contrast it with the conventional paradigm, and to examine its theoretical and practical implications.

When an individual has a particular significant experience, information regarding that experience is stored in the brain. The task at hand for another person lacking knowledge of the original event who wishes to discover the facts regarding the event is to detect this concealed information stored in the brain.

For millennia, the method for achieving this end has been interrogation. Interrogation consists of asking the person questions regarding the information of interest, and attempting to motivate him/her to reveal the information (Aubry & Caputo, 1980). The Farwell Truth Detector introduced here detects the concealed information in a different manner: by measuring electrical brain activity that results, in certain circumstances, from the presence of the concealed information.

In conventional detection of concealed information, when an individual is questioned regarding information that he or she may be motivated to conceal, some means of assessing the credibility of the statements made must be practiced in order for the questioning to be productive (Richardson, 1963). Credibility assessment can be achieved in two ways: 1) through observation of overt behavior, and 2) through observation of non-overt behavior through psychophysiological measurement.

Although the detection of concealed information and credibility assessment through psychophysiological means have been practiced successfully for thousands of years, the utilization of scientific instrumentation in this pursuit has been practiced for only about a century.

This practice is generally known as lie detection, detection of deception, or polygraphy. What is actually detected, however, is neither lies nor deception; and there are many other uses of the polygraph. Thus, the term "interrogative polygraphy" is perhaps a more suitable term. I shall use the term "psychophysiological detection of concealed information" as inclusive of both interrogative polygraphy and alternative methods of detection involving the observation of psychophysiological responses without instrumentation.

Prior to the research reported here, interrogative polygraphy and all other recorded attempts to utilize psychophysiological measures in the service of detecting concealed information were based on an emotional/physiological arousal paradigm (Munsterberg, 1908; Reid & Inbau, 1977; Matte, 1980; Ansley, 1975). It is well known that when faced with a potentially threatening situation, the body prepares itself to become vigorously, physically active in order to deal with that situation. This preparation takes place when strong emotions are aroused, even if an actual physical response of fighting or fleeing is known to be out of the question. Psychophysiological methods of detecting concealed information have been founded on eliciting such emotions (Ferguson & Miller, 1973; Gugas, 1979).

The fundamental procedure that has been developed based on this phenomenon combines interrogation and psychophysiological credibility assessment (Inbau & Reid, 1953; 1962; Aubry & Caputo, 1980). There are three aspects to this procedure:

1) The subject is questioned regarding the event in question, and his/her answers are noted.
2) The subject is confronted with questions or statements regarding the event in question, in a context that is potentially threatening or fear inducing. According to the theory, a subject who has actual information that he has not accurately revealed (a "guilty" subject) will experience greater negative emotions than a subject who is not concealing information (an "innocent" subject).
3) According to the theory, this negative emotion will result in a physiological activation preparatory for strenuous physical activity that can be measured through various channels—primarily perspiration on the palms, changes in cardiovascular activity, and changes in breathing patterns (Reid & Inbau, 1977; Matte, 1980; Ferguson & Miller, 1974). (Several other responses, including salivation, peripheral blood flow, and pupillary responses, have also been measured.)

What is actually measured is the physiological response. According to the theory of conventional interrogative polygraphy, a large physiological response indicates a large emotional response, which in turn indicates guilt or deception (Ferguson & Miller, 1973; Matte, 1980). As will be described in detail in subsequent sections, this simple theory has remained essentially unchanged for two thousand years (Ferguson & Miller, 1974). This is not to say that there has been no progress in interrogative polygraphy during that time. The progress that has taken place—and, particularly during the last quarter century, this has been extensive—has been of an empirical nature. As a recent report prepared under the auspices of the Department of Defense (Department of Defense, 1984) concluded, "The polygraph field is one of those rare situations where the practice has outpaced the research."

Polygraphers have had extensive opportunities to develop a database consisting of physiological responses on the one hand and confessions or other determinations of guilt or innocence on the other. An extensive and systematic body of knowledge has developed regarding the specific patterns of responses that correspond with an ultimate determination that the subject was guilty or innocent (Munsterberg, 1908; Marston, 1917; Larson, 1922, 1932, 1969; Keeler, 1930; Reid & Inbau, 1977; Raskin, 1989). In parallel with this, much has been learned about criminal psychology and the interrogative techniques that are most effective in eliciting revealing responses, both overt and psychophysiological (Munsterberg, 1908; Inbau & Reid, 1962; Gugas, 1979; Aubry & Caputo, 1980).

A simple theory provided the original impetus to make physiological measurements. For the purpose of practical results in investigations, the theoretical foundations, theoretical implications, and intervening variables are not of primary importance (Department of Defense, 1984). What has been systematically and extensively investigated is 1) what physiological patterns can be taken as reliable indicators of guilt, and 2) what techniques of interrogation are most effective in making use of these responses (Reid & Inbau, 1977; Aubry & Caputo, 1980).

In order to detect information that is stored in the brain, conventional interrogative polygraphy resorts to interrogations to elicit true or false statements, and psychophysiological credibility assessment or lie detection to determine whether the subject can be believed or not. The lie detection procedure involves presenting a stimulus that is relevant to the concealed information in a potentially threatening or upsetting situation and measuring physiological responses—on the theory that a guilty individual will emit a greater emotional response to the relevant stimuli, and this greater emotional response will be reflected in a greater physiological response (Munsterberg, 1908; Marston, 1917; Selling, 1938; Ansley, 1975; Matte, 1980; Gale, 1988; Raskin, 1989).

The theoretical basis, then, of conventional psychophysiological detection of concealed information is a general arousal theory. Since the origin of interrogative polygraphy, psychophysiological research has gone beyond a general theory of arousal to explore a variety of more specific psychophysiological responses related to emotions (Lacey, 1967; Obrist, Webb, Sutterer, & Howard, 1970; Schwartz, Weinberger, & Singer, 1981; Mathews, May, Mogg, & Eysenck, 1990; Davidson, Ekman, Saron, Senulis, & Friesen, 1990; Ekman, Davidson, & Friesen, 1990; Lang, Bradley, & Cuthbert, 1990; Eysenck, Mogg, May, Richards, & Mathews, 1991). This further development, however, has not fundamentally changed the theory of interrogative polygraphy. Progress in conventional interrogative polygraphy has consisted primarily of an empirical investigation of what psychophysiological responses are indicative of guilt or deception. A variety of different patterns have been shown to be reliable predictors in this regard (Reid & Inbau, 1977; Matte, 1980; Ansley, 1975).

Two closely related areas where considerable theoretical, as well as practical, advances have taken place in recent years are criminal assessment through observation of overt behavior, and criminal psychology and interrogation (Richardson, 1963; Inbau & Reid, 1962; Gugas, 1979; Aubry & Caputo, 1980). These are beyond the scope of this paper.

Remaining within the realm of general arousal theory, two different methods of interrogative polygraphy employing brain waves could be designed. Alpha waves have been hypothesized to be an indicator of cortical deactivation and general relaxation, and both alpha blocking and beta waves have been hypothesized to be an indicator of cortical activation. Although these hypotheses are not universally accepted, they have received a considerable measure of empirical support. (See, for example, Nowlis & Kamiya, 1970; Brown, 1971; Andersen & Andersson, 1968; Lippold & Novotny, 1970; Shaw, Foley, & Blowers, 1970; Plotkin & Cohen, 1976; Travis, Kondo, & Knott, 1975; Lynch & Paskewitz, 1971; Davidson, 1984a, 1984b; 1987; Kinsbourne & Bemporad, 1984; Leventhal & Tomarken, 1986; Silberman & Weingartner, 1986; Tucker & Frederick, 1989; Davidson & Tomarken, 1989; Davidson, Ekman, Saron, Senulis, & Friesen, 1990). Based on this, one could reasonably advance the hypothesis that the presentation of a crime-relevant stimulus would elicit greater alpha blocking and/or greater beta activity in a guilty person than in an innocent person.

Another theory holds that voltage potential at the scalp is an indication of the level of activation of the brain. There is strong evidence that this is the case in certain limited circumstances, particularly situations involving motor potentials (Kornhuber & Deeke, 1965; Kutas & Donchin, 1980). Some have theorized that slow event-related brain potentials are the result of modulations in the level of widespread cortical activation: negative potentials indicate activation; apparently positive potentials can be explained as transient deactivation (Desmedt, 1980; Verleger, 1988). If this theory is correct, then one could on this basis predict increased cortical negativity in a guilty subject's response to crime-relevant stimuli, since these stimuli would, as indicated by other measures, result in a higher level of activation. As will be described in detail in subsequent sections, the findings predicted in this paper are incompatible with this theory and this predicted result.

The New Paradigm

This paper proposes a new paradigm regarding concealed information and its relationship to psychophysiological measurements, and describes a series of experiments implementing and evaluating this paradigm. The paradigm is distinct from the emotional/physiological arousal paradigm, based on a general arousal theory, that has formed the basis of interrogative polygraphy to date. If the results are as predicted, this new paradigm promises to provide a new means of psychophysiological detection of concealed information that detects the presence of the information more directly and reliably than the conventional methods—without recourse to the mandatory elicitation of negative emotions or dependence on the linkage between negative emotions and physiological arousal.

The P300 Component

The theory and research presented here are based on the P300 component of the event-related brain potential, also referred to as P3 and P3b. There is considerable evidence that P300s are elicited by relatively rare stimuli within a series of more frequent stimuli, when—and only when—these rare stimuli provide information needed by a subject for the performance of a task assigned by the experimenter. For example, if a subject is instructed to count low tones in a series of 20% low and 80% high tones, the low tones will elicit a P300. If the subject is asked to ignore the tones and solve a mental problem instead, the same tones do not elicit a P300 (Duncan-Johnson & Donchin, 1977). If a series of photographs is presented containing a majority of neutral photographs along with a few photographs of politicians and a few photographs of movie stars, a subject will emit P300s in response to one but not the other of these categories, depending on which category he or she is instructed to count (Towle, Heuer, & Donchin, 1980). P300's, then, have been shown to be elicited by stimuli that are rare and explicitly task-relevant.

There are two major classes of theories to explain this phenomenon. One class of theories, exemplified by the context updating theory (Donchin, 1981; Donchin, Karis, Bashore, Coles, & Gratton, 1986; Donchin & Coles, 1988a; 1988b), holds that the P300 is the manifestation of an active information processing "subroutine" in the brain. According to context updating, when the explicitly task-relevant stimulus arrives, the subject updates his internal representation of the environment, and it is this active process that is manifested in a P300 on the scalp.

Another class of theories of the functional significance of P300 holds that the P300 is the result of a transient deactivation of the cortex (Desmedt, 1980; Verleger, 1988). The cortex has been activated in anticipation of the arrival of the task-relevant stimulus. When the stimulus arrives "context closure" occurs, the subject momentarily relaxes his vigilance, and the cortex is deactivated, resulting in an apparent positivity. Then the cortex is again activated in anticipation of the next stimulus, resulting in a return to the previous state of cortical negativity (that appears to be a return to baseline).

Context updating, then, holds the P300 to be a manifestation of the activation of a specific, information-processing process. Brain deactivation/closure holds the P300 to be the result of a transient cortical deactivation. Note that these two theories are not directly comparable. Context updating specifies the functional significance of P300 in terms of a specific information-processing function; it does not specify particular brain structures or physiological brain functions. Brain deactivation specifies particular electrophysiological events in particular brain areas—specifically, deactivation of certain cortical areas—and explicitly denies the existence of any specific, concomitant information-processing process. These differences will be discussed in detail in subsequent sections.

Psychophysiological Detection of Concealed Information with the P300

If the context updating theory is correct, it may be possible to design an interrogative polygraphy technique that takes advantage of the specific nature of the information-processing process manifested in P300 to draw conclusions regarding the information that is processed—and therefore possessed—by the subject. This is the perspective taken in the research described here.

On the other hand, if the cortical activation/deactivation theory is valid, it may be possible to develop a method of interrogative polygraphy through the elicitation of increased cortical activation and corresponding negativity by the presentation of crime-relevant stimuli, or through other interrogative techniques eliciting cortical activation.

The different predictions made by these two theories, and the practical applications for psychophysiological detection of concealed information, will be discussed in detail in subsequent sections.

It is well established that P300's are elicited by stimuli that provide information necessary for the performance of an explicit task assigned by the experimenter (Sutton, Braren, Zubin, & John, 1965). In previous research, P300's have been absent in the absence of relevance to such an explicit task (Sutton, Tueting, Zubin, & John, 1967; Duncan-Johnson & Donchin, 1977).

The hypothesis advanced here is that stimuli that are not explicitly task-relevant will nevertheless elicit a P300 if they are particularly significant to the subject due to his past experience with the subject matter of the stimuli. This is based on the context updating model. If this model is correct, then when a stimulus that is significant for the individual arrives., he or she can be expected to take particular note of it, thus revising his/her internal representation of the current environment and emitting a P300. If this is shown to be the case, this will lend support to the notion that the P300 is indeed the manifestation of a particular, active process. Moreover, it will demonstrate that this is a process that takes place upon the arrival of relevant information even when the subject is not instructed or motivated to engage in this process—in fact, when it is to the subject's disadvantage to do so.

Again, previous research has indicated that stimuli will elicit a P300 only when they are explicitly task-relevant, and not when they are not explicitly task-relevant even if they are recognized by the subject (e.g., movie stars when one is counting politicians; Towle, Heuer, and Donchin, 1980). A hypothesis advanced here is that explicit task relevance is not a necessary condition for the elicitation of a P300. What could be called "implicit task relevance"—a high measure of significance for the subject—is a sufficient condition on the task relevance dimension.

This paper sets forth a series of experiments to test this hypothesis, and also to investigate further the nature and prerequisites for implicit task relevance or significance.

The Research Program

The original research program comprises three experiments. (Experiments 1 and 2 were reported by Farwell & Donchin, 1986, 1991. Experiment 3 was reported by Farwell, 1992.) In Experiment 1, a particular set of stimuli was made implicitly relevant to a subject by requiring the subject to learn them through an interactive computer program and to carry out a mock espionage scenario utilizing the relevant information. On the following day, subjects were presented with the implicitly relevant "probe" stimuli interspersed with two other types of stimuli: irrelevant stimuli and target stimuli. All stimuli were visually presented short phrases. Subjects were asked to memorize a list of targets, and to press one button in response to targets and another button in response to all others. Target and probe stimulus probability were 0.17; irrelevant probability were 0.66. Each subject was tested with two different sets of stimuli, one containing probes relevant to an espionage scenario he or she has carried out ("guilty" condition), and one with probes associated with another scenario unknown to the subject ("innocent" condition).

The innocent condition, then, was simply a standard experiment of the kind that has been shown to produce P300's. Since the subject cannot distinguish the probes from the irrelevants, he sees only two kinds of stimuli: rare and task-relevant targets, and frequent irrelevants. A P300 is expected in response to the targets and not in response to the irrelevants and the probes (which are not recognized as such).

The guilty condition provides a test of the implicit task relevance hypothesis and indirectly of the context updating model on which it is based. If my hypothesis is correct, the subject will display large P300's to probes as well as to targets.

Experiment 2 sought to delineate further the nature of implicit task relevance. In Experiment 1, probe stimuli are learned only one day prior to testing, and are learned in the context of the experiment. In Experiment 2, the probe stimuli consisted of phrases relevant to an actual crime or socially undesirable act committed by the subject up to several years before testing. Stimulus sets were developed through discussion with the subject on the day prior to testing. In other regards, experimental design and predicted results were similar to Experiment 1.

Even if the results of Experiment 2 are as predicted, it is still possible that the significance of the probes is a function of the discussions that take place shortly prior to testing. Experiment 3 was designed to test the hypothesis that personal relevance or implicit task relevance can be achieved on the basis of significant life events alone, outside of the experimental setting, and that it can be retained over a period of years. Experimental procedure was as before, except that all information regarding the personal life events that give rise to the probe stimuli will be supplied by a third party who knows the subject well. Subjects will not know what stimuli will be presented or what events will be investigated prior to the test session. As before, the predicted result for a guilty subject is large P300's to targets and probes and not to irrelevants. If the results of Experiment 3 are as predicted, this will serve to delineate further the nature and time course of implicit task relevance, and provide further support for the context updating model of the functional significance of the P300. This will be discussed in detail in the section on "Hypotheses and Theoretical Significance of this Research."

The permission of each subject will be obtained for the acquisition of information from each specific informant. Any information so obtained will remain confidential.

These three experiments, if results are as predicted, can serve as the theoretical and practical foundation of a new form of psychophysiological detection of concealed information. All previous methods involve interrogation—asking the subject about the situation under investigation—and credibility assessment—attempts to determine if the subject is telling the truth (Reid & Inbau, 1977; Matte, 1980; Department of Defense, 1984; Aubry and Caputo, 1980; Raskin, 1986; Lykken, 1978). Credibility assessment in turn involves measurement of physiological responses on the theory that large physiological responses indicate a large emotional response, which in turn indicates that the sought after, crime-relevant information is indeed stored in the brain (Ferguson & Miller, 1973).

The method proposed here seeks to reveal the crime-relevant information stored in the brain through measurement of the psychophysiological manifestations of information-processing brain activity. The Farwell Truth Detector described here does not depend on the elicitation of certain emotions or the measurement of the putative physiological correlates of emotions. The system creates a situation such that the presence of crime relevant information stored in the brain—regardless of emotions or arousal levels—will result in the implementation of a certain information-processing brain function that can be detected electrophysiologically.

One advantage of this approach is that both emotions and the accompanying autonomic nervous system arousal can be multiply determined, whereas the process manifested in the P300 is a quite specific one. On the emotional level, there may be many reasons other than guilt or falsehood why a person may be aroused (or fail to be aroused) by being questioned about a crime. Moreover, the autonomic nervous system is activated not only by emotions. It is responsible for maintaining homeostasis in the system as a whole. It continually readjusts the balance between anabolic and catabolic processes, maintains a suitable temperature in the different areas of the body, supplies nutrients and oxygen to different organs on demand and according to a complex system of shifting priorities, and makes a multitude of adjustments in different bodily systems in response to continually changing conditions in the internal and external environment. Thus, the changes in autonomic nervous system activity measured by conventional polygraphy may be the result of a multitude of psychological and physiological factors, some related to the subject of the investigation and some unrelated. Moreover, a knowledgeable subject may deliberately engage in psychological or physical activities that influence autonomic nervous system activity during an examination, and such countermeasures may have considerable effectiveness (Honts, Hodes, & Raskin, 1985; Honts, Raskin, & Kircher, 1987).

By contrast, there is strong evidence that the information-processing activity of which the P300 is a manifestation is a specific one (Donchin, Karis, Bashore, Coles, & Gratton, 1986). The brain-wave information detection (BID) system described here attempts to give the subject a task where that particular information-processing function comes into play if and only if the relevant information is stored in the brain. As will be described in detail in subsequent sections, the Farwell Truth Detector attempts in this way to establish a very specific link between a psychophysiological measurement and the presence or absence of specific, relevant information stored in the brain.

EARLY PSYCHOPHYSIOLOGICAL DETECTION OF CONCEALED INFORMATION

The Veda, the earliest record of human experience, contains the first record of systematic methods for the psychophysiological detection of concealed information. The Veda is said to be well over 10,000 years old. However, since it was passed down orally for many generations by pundits who memorized it syllable for syllable and taught it to the upcoming generation from an early age, it is difficult to ascertain its age accurately. It may have been first written down about 900 B.C. Ancient Vedic scientists used the pulse, measured from the wrist, to diagnose a wide variety of physical, mental, emotional, and spiritual imbalances, including both guilt over past deeds and tendencies to violence and other crime. The Mitakshara Shastra of the Ayur Veda, that section of the Vedic literature concerned with both psychophysiology and health, offered the following method for detecting individuals who had committed the particularly heinous crime of poisoning:

> A person who gives poison may be recognized. He does not answer questions, or they are evasive answers; he speaks nonsense, rubs the great toe along the ground, and shivers; his face is discolored; he rubs the roots of the hair with his fingers; and he tries by every means to leave the house . . . " (Mitakshara Shastra. See Wise, 1845, p. 394; see also Trovillo, 1939; Horvath, 1973).

Like the methods employed in modern interrogation, this ancient account calls for the observation of both psychophysiological and overt behavioral symptoms.

The first practice of psychophysiological detection of concealed information recorded in detail was by the Greek physician and physiologist Erasistratos in the third century B.C. (Appian of Alexandria, early second century A.D., 1962; Plutarch, first century A.D./1952; Valerius Maximus, first century A.D./1888; see also Mosso, 1896; Trovillo, 1939; Horvath, 1973; Mesulam & Perry, 1972). Erasistratos used psychophysiological detection of concealed information, without the benefit of modern psychophysiological recording equipment, to solve a particularly difficult medical case. His patient was a young man named Antiochus, the son of Seleucus I of Syria, a former general of Alexander the Great who had recently married a beautiful younger woman named Stratonice. Antiochus fell in love with his new stepmother, and realizing the hopelessness of his situation, attempted to hide his passion. He soon became very ill.

Erasistratos concluded that the young man had no physical ailment, and consequently his illness must have an emotional origin. He made careful psychophysiological observations of Antiochus' responses to various stimuli in the environment in order to determine the cause of the illness. Suspecting that the young man's difficulties arose from his feelings for another individual, and that he was doing his best to avoid any overt behavior that would give him a way, Erasistratos made some of the same measurements that are now incorporated in modern polygraph testing, along with other related observations. Here, in the words of Plutarch (first century A.D./1952), is what Erasistratos observed:

He . . . waited continually in his chamber, and when any of the beauties of the court made their visit to the sick prince, he observed the emotions and alterations in the countenance of Antiochus, and watched for the changes which he knew to be indicative of the inward passions and inclinations of the soul. He took notice that the presence of other women produced no effect upon him; but when Stratonice came as she often did, alone or with Seleucus, to see him, he observed in him all of Sappho's famous symptoms,—his voice faltered, his face flushed up, his eyes glanced stealthily, a sudden sweat broke out on his skin, the beatings of his heart were irregular and violent, and, unable to support the excess of his passion, he would sink into a state of faintness, prostration, and pallor.

The "sudden sweat" described by Erasistratos constitutes the primary symptom recorded by modern interrogative polygraphy. The "irregular and violent beatings of the heart"—also a response recorded in modern lie detection—could only have been observable if Erasistratos had actually taken the pulse at the appropriate times (a fact that was pointed out by another great early Greek physician and scientist, Galen of Pergamum, second century A.D.).

Here Erasistratos exhibits a sophisticated theoretical understanding of psychophysiology, the same theoretical understanding that forms the basis of all modern conventional interrogative polygraphy prior to the system proposed here (Matte, 1980; Ferguson & Miller, 1973). Erasistratos must have realized that emotions and bodily functioning are intimately related. He recognized that a stimulus in the external world could produce a visceral response due to its particular significance for an individual. He replicated his findings on the relationship of the stimulus and the psychophysiological response through repeated observations at different times. Erasistratos also must have understood that the visceral responses could reveal emotions—and, by inference, the concealed information that gave rise to them—even if the subject was determined to reveal neither the emotion nor the facts giving rise to it through any overt means. Moreover, Erasistratos' scientific study was a controlled one. He assured himself of the specificity of the stimulus by comparing the subject's response to the critical stimulus to his responses to the presence of other individuals of the court.

Galen of Pergamum, often hailed as the father of modern medicine and an admirer of Erasistratos, further developed the theoretical and practical approach introduced by his predecessor (Mesulam & Perry, 1972). He applied it to solve a similar problem, this time with a woman suffering from insomnia. After examining her, he concluded that it was likely that her problem was due to "some trouble she was unwilling to confess." (Galen, second century A.D.)

While I was convinced the woman was afflicted by not bodily disease, but rather that some emotional trouble grieved her, it happened that at the very moment I was examining her this was confirmed. Someone returning from the theater mentioned he had seen Pylades dancing. Indeed, at that instant, her expression and the color of her face were greatly altered. Attentive, my hand laid on the woman's wrist, I observed her pulse was irregular, suddenly violently agitated, which points to a troubled mind. The same thing occurs in people engaged in an argument over a given subject.

The next day, I told one of my following that when I went to visit the woman he was to arrive a little later and mention that Morpheus was dancing that day. When this was done the patient's pulse was in no way changed. And likewise, on the following day, while I was attending her, the name of the third dancer was mentioned, and in like fashion the pulse was hardly affected at all. I investigated the matter for a fourth time in the evening. Studying the pulse and seeing that it was excited and irregular when mention was made that Pylades was dancing, I concluded that the lady was in love with Pylades and in the days following, this conclusion was confirmed exactly.

Galen's scientific application of psychophysiology to detect concealed information goes beyond that of Erasistratos. Rather than passively waiting for the arrival of the critical stimulus, Galen intentionally manipulated the environment to elicit the responses in question. He used control stimuli as well as relevant ones. Moreover, he recognized the concept, fundamental to modern interrogative polygraphy, of stimulus generalization: the name, rather than the individual, was enough to elicit the response (Mesulam & Perry, 1972). In a criticism of physicians ignorant of the psychophysiological connection between mind and body, Galen (second century A.D.) clearly describes the intimate relationship that forms the basis of modern conventional interrogative polygraphy.

Why did these things escape the notice of earlier physicians attending the lady described above?. They are arrived at by ordinary deduction, if the physician has even a meager knowledge of medicine.

Indeed, I think that it is because these physicians possess no clear conception of the ways the body tends to be influenced by the state of the mind. Perhaps it is because they do not even know that the pulse becomes turbulent because of strife and fears which suddenly disturb the mind.

In the tenth century the great Persian physician Avicenna, in his Canon medicinae, describes similar success to that of Erasistratos and Galen in diagnosing "love-sickness," and systematic identification of its object, in an individual who had been unwilling to confess his condition. Avicenna also expanded the concept of stimulus generalization to include not only the name of the relevant person but other related items such as her place of residence. Avicenna's (also known as Ibn Sina, tenth century A.D) description of his method is extremely similar to the conventional lie detection practiced by interrogative polygraphers today (Ibn Sina, 1608; Mesulam & Perry, 1972). In the following passage, Avicenna (Ibn Sina, 1608) describes the detection of a love-sick individual.

> It is possible in this way to ascertain whom he loves, even when he will not reveal it himself . . . The nature of the cure is this: let several names be pronounced, repeating them many times, and place your finger on the patient's pulse. When it varies by a large fluctuation and then returns to normal, and this is repeated thereafter, and is put to the test many times, then the name of the one he loves will be known.
>
> Again, similarly, make mention of her looks and habits and that in which she excels, her family, where she lives, so that any one of these things may be associated with the name of his loved one. Observe his pulse in such a way that when it fluctuates at the mention of one of these details the particular characteristics of his loved one may then be associated with a name and with an outstanding feature, by all of which she is to be recognized.

It is clear that the theoretical foundations of conventional interrogative polygraphy, and indeed a recognition of many of the critical psychophysiological responses to be measured, are founded on a two-thousand-year-old tradition. Modern conventional interrogative polygraphy has built upon this foundation with sophisticated instrumentation, and has developed a rich empirical data base.

THE DEVELOPMENT OF MODERN CONVENTIONAL INTERROGATIVE POLYGRAPHY

Interrogative polygraphy, the use of scientific instrumentation in psychophysiological detection of concealed information, began with Lombroso in the late nineteenth century (Lombroso, 1890, 1887, 1911, 1912; Ferraro, 1911). Lombroso made continuous recordings of cardiovascular activity by placing a subject's hand in a water-filled tank covered with a rubber membrane. Cardiovascular activity was reflected by changes in the volume of the fist, which modulated the water level. Changes in the water level were transferred by an air-filled tube to a revolving smoked drum. Lombroso's measurement met with some success in detecting actual criminals.

The first "polygraph" for recording cardiac activity that contained the essential features utilized in the modern polygraph for recording cardiovascular phenomena was developed by heart specialist Sir James Mackenzie in 1906 (Mackenzie, 1908; Gay, 1948). It was used, however, not for the psychophysiological detection of concealed information but for medical purposes. As early as 1908 Harvard professor Hugo Munsterberg (1908), an innovator in the psychophysiological study of emotion, proposed the use of all three of the measurements now commonly used in lie detection, along with several other behavioral and psychophysiological parameters. His description of the techniques is both insightful and poetic.

> If a girl blushes when a boy's name is mentioned in the family sitting-room, we feel sure, even if she protests, that he is not quite indifferent to her young heart. If she opens a letter and grows pale while reading it, she may assure us that the event is unimportant; we know better . . .
>
> Yes, the hidden feeling betrays itself often against the will . . . It may be easy to suppress intentionally the conspicuous movements by which we usually accentuate the emotions . . . But the lips and the hands and arms and legs, which are under our control, are never the only witnesses to the drama which goes on inside—if they keep silent, others will speak.
>
> Our inspirations and expirations can be registered in finest detail and a variety of elegant methods are available. Perhaps the simplest "pneumograph" consists of a tube made of spiral wire and covered with rubber, to be attached by ribbons to the chest . . . As soon as such delicate methods of registration are applied, the intimate relation between feeling and breath becomes evident . . .
>
> The same holds true for the heart beat, measured by the blood wave in the arteries; such a pulse writer is called a sphygmograph. It may be attached, for instance, to the wrist; a delicate lever presses against the wall of the blood vessel just where the finger of the physician would feel the pulse . . . When we write pulse and breathing together on the same drum, we see at once that even ordinary inspiration changes the pulse; while we inhale we have a pulse different from the pulse when we exhale. Far more influential are the feelings . . .
>
> But there is still another way to observe the changes in our blood vessels. We may examine the quantity of blood, for instance, which streams to a limb, by means of the so-called plethysmograph . . . every emotional excitement speaks in the blood supply of every limb.
>
> But we may go still further and point to expressions of emotion which are entirely beyond human senses. If we put our hands on two copper plates and make the weak galvanic current of a battery run through the plates and our body, we can, with the help of a delicate galvanometer, measure the slightest variations of the resistance of the current. Experiment shows that such changes occur, indeed, if our brain is excited; any emotional disturbance influences the resistance: it seems that the activity of the sweat-glands in the skin is under the nervous influence of our feelings, and the functioning of these glands alters the electrical conditions. A word we hear may excite us and at once the needle of the galvanometer becomes restless: there is no more uncanny betrayal of our inmost mind. (Munsterberg, 1908, p. 113)

A device incorporating all three of the measures included in a modern polygraph—pulse, breathing, and skin conductance—was proposed to a congressional hearing by Arthur McDonald in 1908, but such a device was not constructed until years later.

In 1914 Vittoria Benussi reported some success in detecting deception through measuring changes in breathing patterns (Benussi, 1914). In 1915 William Marston (Marston, 1917; 1938), a student of Munsterberg's and later also a professor at Harvard, began a series of experiments using blood pressure in the detection of deception. He used an ordinary sphygmomanometer to record blood pressure periodically during questioning. Marston also recorded breathing patterns and experimented with skin resistance measurements.

Burtt (1918) also experimented with respiratory measurements and blood pressure in lie detection. He held the blood pressure changes to be of greater diagnostic value.

The first continuous recording of blood pressure in interrogative polygraphy was accomplished by Larson (1921; 1922). He developed an instrument that simultaneously recorded blood pressure, pulse, and respiration continuously throughout a test session. Larson's device was used extensively in criminal investigations, and reportedly enjoyed a high degree of success (Larson; 1932).

In 1926 Keeler (1930) developed a machine that accomplished the same measurements as Larson's and incorporated a number of technical improvements.

In 1938 Keeler incorporated the third major component of the modern polygraph, namely the psychogalvanometer invented by Galvani in 1891. This provided for the measurement of the skin's resistance to (or conductance of) an electrical current, commonly known as electrodermal response (EDR), galvanic skin resistance (GSR), or skin conductance response (SCR).

By this time, considerable research had been published on skin resistance, but little of it had been related to the psychophysiological detection of concealed information. An exception was Summers (1939), who conducted thousands of laboratory experiments and investigated about 50 actual cases using galvanic skin resistance, reportedly achieving a high level of accuracy in detecting deception or guilt.

Another early researcher in the use of galvanic skin resistance in psychophysiological detection of concealed information was Wilson (Trovillo, 1939), who developed a new recording psychogalvanometer in 1930 and used it in collaboration with Keeler in several investigations. Shortly thereafter, the Chicago Police Crime Detection Lab first used galvanic skin resistance in conjunction with blood pressure measurements in the psychophysiological detection of concealed information.

It was on this background that Keeler developed the first instrument incorporating the essential features of the modern polygraph. Keeler also refined the relevant-irrelevant test, in which crime-relevant questions are interspersed with irrelevant questions. He experimented with personally embarrassing questions and surprise questions in an attempt to introduce a control stimulus that would evoke a reaction in innocent as well as guilty subjects.

Summers (1939) provided the first descriptions of the control question technique, in which a third type of question is employed that is designed to elicit an emotional response in both guilty and innocent subjects for the sake of comparison with the responses to relevant questions. Previously Larson (1921, p. 396) had referred to a technique in which "a control question, or one not concerning the subject under investigation, and yet calculated to stimulate various emotions, was alternated with one pertinent to the investigation." He did not, however, clearly distinguish between control and irrelevant questions.

Reid (1947; Reid & Inbau, 1977), often credited with first introducing the control question technique, did in fact refine this technique to essentially the same form in which it is practiced today. He also introduced the recording of muscular activity as a means to detect attempted countermeasures. Reid and his colleague, Fred Inbau (Reid & Inbau, 1977; Matte, 1980) did much to systematize the methods for questioning and data acquisition in interrogative polygraphy. Over the years they accumulated voluminous data on the applicability and effectiveness of various techniques of conventional interrogative polygraphy.

INTERROGATIVE POLYGRAPHY: THE CURRENT STATE OF THE ART

Types of Questions

The questions asked of the subject in %conventional interrogative polygraphy fall into four categories: "relevant questions," "irrelevant questions," "control questions," and "concealed information questions." Relevant questions are directly related to the focus of an investigation. Irrelevant questions are irrelevant to the investigation and are structured so as to have little or no emotional significance for the subject. The response to these questions provides a baseline: they establish the typical pattern with which the subject responds to routine questions. Control questions are questions that, while not directly relevant to the situation or issue under investigation, are designed to elicit an emotional response from the subject that is similar to the response that the relevant questions will elicit in a guilty subject. The control questions are concerned with various undesirable behaviors in which the subject may have been involved in the past, and are designed to elicit concern and/or doubt in the subject about the veracity of his response. These questions are also used for the purpose of comparison; they establish the typical physiological response of a subject to questions about which he is concerned. Concealed information questions focus on information about the crime or issue under investigation that would be known only to the guilty party. It is assumed that a guilty individual will respond more vigorously to (that is, be more physiologically aroused by) correct details associated with the crime than to incorrect details, whereas innocent subjects lacking in knowledge of the correct details will have the same response to both classes of items.

The Three Classes of Conventional Interrogative Polygraphy Tests

These four classes of questions are employed in three different interrogatory systems: 1) the relevant/irrelevant test, 2) the control question test, and 3) the concealed information test.

1) The Relevant/Irrelevant Test

In the relevant/irrelevant test (Larson, 1922, 1932; Keeler, 1930), two types of questions are presented: relevant and irrelevant. It is presumed that innocent people will respond in a similar manner to the questions from both classes, because they are unconcerned about the crime. Guilty persons will be more aroused by the relevant questions, because they are more concerned about the crime.

This technique has serious drawbacks, the most obvious of which is that the relevant questions concern subject matter that is inherently more upsetting than the irrelevant questions. Some innocent people, as well as guilty individuals, may respond to "Did you shoot John Jones last Tuesday?" or "Have you ever used cocaine?" more strongly than to "Do you live on Cherry Street?"

Therefore a large response to the relevant questions may not be indicative of deception; rather it may be the result of the emotional tendencies and the physiological lability of the subject. Moreover, in the cases where the subject does not respond to the relevant questions, there is no indication how the subjects would have responded had the questions been about criminal activity of which the subject was guilty. In short, there is no control, and as a result both false negatives and false positives will occur. Because of this, the relevant/irrelevant technique is seldom used in investigations of a specific crime or situation, although it is still used in nonspecific investigations such as pre-employment and personnel screening.

2) The Control Question Test

The most frequently employed technique in the investigation of specific crimes or critical situations is the control question test, which was developed to solve some of the problems of the relevant/irrelevant test (Reid & Inbau, 1977; Kircher, Horowitz, & Raskin, 1988). In the control question test, control questions are added to relevant and irrelevant questions. These control questions are designed to elicit an almost obligatory emotional response. It is assumed that an innocent subject will respond more strongly to the control questions, since he/she should not be concerned about the crime or issue at hand. Guilty persons are expected to respond more to the relevant questions, since they are more concerned with the specific issue under investigation than with a general question about something undesirable they may have done in the past.

Summers (1939) referred to the control questions as "emotional standards." Their purpose was "to evoke within the individual rather intense psychogalvanic reactions due to surprise, anger, shame, or anxiety over situations which he would ordinarily prefer to conceal" (p. 341).

The usual control questions are somewhat vague, and cover a long period of time. They are designed to encourage the subject to lie, or at least to be unsure of the truthfulness of his or her answer (Reid & Inbau, 1977). Such control questions are sometimes referred to as "probable lie" questions. An alternative control question is the "directed lie" control question. These are questions regarding past activities, usually very minor negative activities that everyone is assumed to have committed, to which the subject is instructed to lie.

The control question test has been the subject of two classes of studies: 1) field studies involving actual crimes (e.g., Raskin, 1976; Horvath & Reid, 1971; Barland & Raskin 1976; Bersh, 1969; Davidson, 1979; Horvath, 1977; Hunter & Ash, 1973; Kleinmuntz & Szucko, 1984; Sicwick & Buckley, 1975; Wicklander & Hunter, 1975; Raskin, Barland, & Podlesny, 1978), and 2) studies of mock crimes or similar deception-oriented circumstances conducted in laboratories (e.g., Barland & Raskin 1975; Podlesny & Raskin 1978; Raskin & Hare 1978; Rovner, Raskin, & Kircher, 1978; Widacki & Horvath 1978; Dawson 1980; Hammond, 1980; Bradley & Janisse 1981; Szucko & Kleinmuntz, 1981; Ginton, Dale, Elaad, & Ben-Shakhar, 1982; Kircher & Raskin, 1982; Honts, Raskin, & Kircher, 1983; Kircher, 1983; Bradley & Ainsworth, 1984; Gatchel, Smith, & Kaplan, 1984; Honts, Hodes, & Raskin, 1985; Forman & McCauley, 1986).

The results of these studies have been the subject of considerable controversy over the effectiveness of the technique (see, for example, Lykken, 1978, 1979, 1988; Raskin, 1978, 1987, 1988; Raskin & Podlesny, 1979). Accuracy rates for detecting mock guilty subjects have ranged from a low of 71% (Szucko & Kleinmuntz, 1981) to a high of 100% (Dawson, 1980; Dale, Elaad, & Ben-Shakhar, 1982; Raskin & Hare, 1978). Accuracy for the detection of mock innocent subjects has generally been found to be lower, ranging from 49% correct (Szucko & Kleinmuntz, 1981) to 97% (Kircher & Raskin, 1982). A number of factors may contribute to the differences in accuracy rates reported. Studies varied widely in the type of subjects, the motivation of the subjects (higher motivation typically yielded higher detection accuracy), access by examiners to information (e.g., behavioral data) not included in the charts, the amount and type of psychophysiological information provided to the interpreters, the skill of the interpreters, and the method of scoring the charts.

One major difficulty with mock crime and other laboratory studies is that it would be exceedingly difficult (not to mention highly unethical) to subject individuals participating in a study to anything approaching the level of negative emotional arousal experienced by individuals who are actually guilty of major crimes in examinations attempting to detect that fact.

A few laboratory analog studies have provided a somewhat realistic experience. Ginton, Dale, Elaad, and Ben-Shakhar (1982) gave cadets at the Israeli Police Academy an opportunity to cheat on scoring a test they had taken, where the paper was chemically treated to reveal any changes. The officers, some of whom had cheated, were told that they were suspected of cheating, and offered an opportunity to take a polygraph test. They were told that their careers might depend on the outcome of the test. Such manipulations, though undoubtedly at least somewhat effective in simulating an actual field polygraph examination, are highly questionable on ethical grounds, and undoubtedly would not pass a review by a human subjects committee in the United States.

Accuracy rates for field studies have varied even more than those of mock crime studies. Accuracy of detection of criterion guilty individuals has ranged from 71% (Bersh, 1969) to 99% in one condition reported by Wicklander & Hunter (1975). Innocent subjects have been detected with accuracies ranging from 12% (with judicial outcome as the criterion of guilt, reported by Barland & Raskin, 1976) to 94% in one condition reported by Bersh (1969). In addition to many of the same variables affecting analog studies, field studies have varied in the method of selection of cases, the type of crimes, the suspected role in the crimes of the individuals examined, and the criterion for ground truth.

Ground truth is a particularly difficult issue, since in field studies it can never be known with certainty. Confession is held by some to be the most accurate criterion (Raskin, 1989), since it is rather unlikely that a suspect will confess who is not indeed guilty. However, confessions are not independent of the polygraph outcome, and tend to inflate the accuracy of both innocent and guilty determinations by systematically excluding cases where an error has been made. If a guilty subject is falsely found innocent, it is less likely that he or she will confess, and more likely that the investigators will continue mistakenly to seek a suspect who is guilty—which they will not find. Thus, no one will confess, the false negative will go undetected, and the case will be excluded from the analysis. If, on the other hand, an innocent suspect is falsely found guilty, and does not confess, the investigators may tend to lessen their efforts to find the guilty party since they think they already have found him. Again, no confession takes place, the false positive goes undetected, and the case is excluded from the analysis. (In the rare case in which an innocent subject does confess after failing the polygraph test, he is mistakenly scored as a correct detection.)

The other common methods of establishing guilt or innocence in field studies are judicial outcome and decision by a panel of experts. These methods, too, have their share of difficulties (Barland, 1982; Raskin, 1988). The judicial system in the United States, where virtually all of the field research has taken place, is based on the principal of "innocent until proven guilty beyond a reasonable doubt." Thus, both judges and juries and panels of experts who are trained in this legal tradition often tend to err on the side of finding the subject innocent. Also, in both judicial and panel decisions, the quantity of evidence available for consideration may be low, in which case the subject also will generally not be found guilty. This situation is a favorable one for human rights, of course, but it renders these methods of determination of culpability problematical for scientific purposes.

In an attempt to reduce some of the variability across examiners in the interpretation of polygraph charts and to supplement examiner interpretation of polygraph data, computerized statistical techniques have been developed which extract information from polygraph data (Kircher, 1983; Kircher & Raskin, 1981, 1988). The accuracy of this more objective approach is similar to the accuracy of examiner judgments.

The control question test is sometimes used in screening situations to investigate particular classes of activities or future intentions. This involves questioning similar to that employed in screening uses of the relevant/irrelevant technique, with the addition of control questions. Such a use of the control question test involves a difficult balance between control questions of a general nature designed to elicit an emotional response in both innocent and guilty subjects, and relevant questions, also often of a general nature, designed to elicit a response only in the guilty.

A few studies have been conducted on the use of polygraphy in actual government security screening applications. In a study by the Director of Central Intelligence (U.S. CIA, DCI, 1982) on background investigations in the CIA, the polygraph was used in an attempt to evaluate adverse information that had arisen regarding individuals being considered for employment or security clearances. In two-thirds of the cases where the information was resolved against the individual, the individual admitted the adverse information. There is no indication of whether the adverse information was correctly identified in the remaining one-third of the cases; and since the polygraph was used only after a thorough investigation had already revealed evidence against the individuals, it is impossible to know precisely what role the polygraph played or how effective it would have been in the absence of such an investigation and such pre-existing evidence. Edel & Jacoby (1975) showed that polygraph examiner ratings of a "physiological reaction" in applicants for U.S. government employment were reliable across examiners; but they did not determine whether the reaction actually was indicative of deception. In a laboratory study analogous to government security screening applications that used military intelligence personnel as subjects, Barland (1981) used the directed lie technique. Three different blind analysis techniques were used to identify subjects who were lying to any question, and the same three techniques were uses to identify which specific questions elicited lie responses. The average accuracy in identifying both truthful/lying subjects and truth/lie responses to specific questions was 69%.

3) Concealed Information Tests

Concealed information techniques are of two kinds: the guilty knowledge or concealed knowledge test and the peak of tension test. Both work on the premise that a guilty person will exhibit a larger response when confronted with correct details relevant to the crime under investigation than to similar details that are unrelated to the crime. An innocent person is expected to respond identically to both. The guilty knowledge test has been proposed as an alternative to control question techniques (Lykken, 1959, 1960, 1981, 1988; Giesen & Rollison, 1980; Ben-Shakhar, Bar-Hillel, & Lieblich, 1986; Furedy & Helsgrave, 1988). Lykken (1959) is often credited with the development of the guilty knowledge technique, although in fact it was described as early as 1908 by Munsterberg (1908), and its successful application was reported and analyzed in detail by Keeler (1930). In this technique, subjects are asked a variety of questions about details of the crime that would be known only to the guilty party. It is assumed that a guilty person will respond differentially to the correct, crime-relevant details. Scientific studies of the guilty knowledge test, like studies on the control question test, have produced mixed results (Lykken, 1959; Davidson, 1968; Podlesny & Raskin, 1978; Balloun & Holmes 1979; Giesen & Rollison, 1980; Bradley & Janisse, 1981; Stern, Breen, Watanable, & Perry, 1981; Bradley and Warfield, 1984; Iacono, Boisvenu, & Fleming, 1984; Elaad & Ben-Shakhar, 1989). It has been studied almost exclusively in the laboratory. Because the innocent subject does not know which are the relevant questions, the guilty knowledge test has often achieved a very low level of false positives (e.g., 0% in Lykken, 1959; Davidson, 1968; and Podlesny & Raskin, 1978). False negatives, however, have been a significant problem, sometimes reaching levels of about 40% (e.g., Balloun & Holmes, 1979; Bradley & Janisse, 1981).

In the peak of tension test (Harrelson, 1964), a question concerning a relevant and correct detail about a crime is embedded in a series of questions mentioning similar but irrelevant details. The sequence of presentation of the questions is known in advance to the subject. It is assumed that the physiological response will peak at the time of the relevant question (Barland & Raskin, 1973; Lykken, 1981).

Theory in Conventional Interrogative Polygraphy

In the two thousand years since Erasistratos made his successful discoveries, a large and rich data base has accumulated regarding the appearance and measurement of the changes . . . indicative of the inward passions and inclinations of the soul" (Plutarch, first century A.D./1952). Much more is now known about the mechanism through which the autonomic nervous system, when activated by emotion, brings about the changes measured by polygraphers. (See, for example, Lacey, 1967; Obrist, Webb, Sutterer, & Howard, 1970; Porges & Coles, 1976; Schwartz, Weinberger, & Singer, 1981; Kandel and Schwartz, 1985; Coles, Donchin, & Porges, 1986; Mathews, May, Mogg, & Eysenck, 1990; Davidson, Ekman, Saron, Senulis, & Friesen, 1990;

Ekman, Davidson, & Friesen, 1990; Lang, Bradley, & Cuthbert, 1990; Eysenck, Mogg, May, Richards, & Mathews, 1991).

The fundamental psychophysiological theoretical foundation driving modern conventional interrogative polygraphy, however, is fundamentally the same as that which led Erasistratos to his early success in the psychophysiological detection of concealed information. One addition of modern interrogative polygraphy is the understanding of the adaptive value that these psychophysiological changes have in a physically dangerous situation.

> Emotions consist of intensified feelings regarding a situation, which are caused by an interaction between the mind and the body resulting in physiological changes within the body to cope with the situation ... When these feelings are strong ... the accompanying physiological changes are extensive. Under strong fear, these changes have the effect of preparing the body for a fight or flight ..
>
> The system that prepares the body's defenses to meet these emergencies is...the sympathetic subdivision of the autonomic nervous system ... In a polygraph situation, it is fear, fear of detection, fear of the consequences if the individual is detected, that causes the sympathetic system to activate in order to prepare the body to meet the emergency (Matte, 1980).

This modern description of the phenomenon is very similar to the ancient descriptions advanced by Erasistratos, and also to the descriptions set forth by early interrogative polygraphers. Munsterberg's (1908) explanations have been quoted above. Benussi (1914) attributed the physiological changes he measured to "internal excitement."

Marston (1917, 1938) analyzed in some detail the effect of the emotions of fear and rage on the sympathetic nervous system, and reached similar conclusions (although some of the details of Marston's analysis have not found favor with later experts). Similarly, Burtt (1921a, 1921b), after extensive experimentation and debriefing of subjects, implicated "fear or excitement." Keeler (1930) held that fear was the primary emotion behind the responses of a guilty subject.

There has been considerable controversy in recent years over the emotional/physiological arousal paradigm in interrogative polygraphy. One major contributing factor to this controversy may be the gulf that has developed between practicing polygraphers and academic scientists.

The ancient proponents of the emotional/physiological arousal paradigm for psychophysiological detection of concealed information were physician/scientists. Many of the early proponents of the introduction of modern instrumentation in the service of this paradigm in the first third of the twentieth century were scientists well within the mainstream of current scientific theory and methodology. They used the same equipment in interrogative polygraphy that they used for other, unrelated physiological and psychophysiological research (Munsterberg, 1908). After the introduction of the "polygraph" as a specific piece of machinery with the sole purpose of lie detection, however, a new breed of experts arose. The original field of expertise of these individuals was not physiology or psychophysiology but criminology and law enforcement.

Their expertise was primarily developed not in the scientific laboratory but in the applied, field setting, where both the theoretical and practical considerations held to be important differed from those that caught the attention of the academic psychophysiologists of the day. Critics and proponents alike agree that there was little contact between practicing polygraphers and the academic community. As Raskin (1979) stated, "It is interesting to note that field polygraphers (Backster, 1962; Reid, 1947) have managed to develop effective procedures for detection of deception in the field setting without the benefit of formal training in psychology and physiology and with minimal contact with the academic—scientific community."

Outside of the field of interrogative polygraphy, considerable attention was given to distinguishing between the psychophysiological manifestations of different emotions and developing a more detailed account of the psychophysiological signature of different emotional responses (Ax, 1953; Vanderhoof & Clancy, 1962; Lacey, 1967; Lacey & Lacey, 1970; Obrist, Webb, Sutterer, & Howard, 1970; Porges & Coles, 1976; Schwartz, Weinberger, & Singer, 1981; Mathews, May, Mogg, & Eysenck, 1990; Davidson, Ekman, Saron, Senulis, & Friesen, 1990; Ekman, Davidson, & Friesen, 1990; Lang, Bradley, & Cuthbert, 1990; Eysenck, Mogg, May, Richards, & Mathews, 1991). It has been shown, for example, that a unified theory of arousal is inadequate to explain some observed phenomena. Psychophysiologists have distinguished between different responses such as the orienting reflex and the defensive reflex: skin conductance increases in both cases, whereas heart rate decreases with the orienting reflex and increases with the defensive reflex.

Such distinctions, however, have by and large not been important for the actual practice of conventional interrogative polygraphy (Reid & Inbau, 1977).

Established on the original theoretical foundation recognizing the link between emotions and physiological responses, interrogative polygraphy has proceeded primarily empirically (Department of Defense, 1984; Raskin, 1979).

A strong psychophysiological response of any one of a number of flavors has been deemed sufficient to reveal that a relevant stimulus is emotionally arousing for an individual. In practice, polygraphers have come to recognize a wide variety of different, sometimes opposite responses as indicators of the state or states of heightened emotion that are hypothesized to accompany deception (Reid & Inbau, 1977).

> A person's body functions at one physiological pace during chart time...whether fast, slow, calm, "nervous," or excited. This pace will henceforth be referred to as "norm." The instrument merely records this norm and any deviation therefrom. A deviation from norm, commonly called a response or reaction, is the result of a verbal stimulus (a question) ... If a certain brain center interprets the question to mean harm to a person's well-being, providing the question is answered truthfully, a series of nerve impulses is generated. Specifically, the brain has delegated responsibility for protection of the body to the autonomic nervous system and its emergency subdivisions, the sympathetic and parasympathetic. As this emergency system goes into action, a minor to major change is recorded on a moving chart. (Ferguson & Miller, 1973, p. 146).

Although polygraphers have described in considerable detail the neurological mechanisms through which emotions and the concomitant autonomic nervous system activities are revealed in polygraph recordings (Ferguson & Miller, 1973), and some have indicated the need for some degree of specificity in the emotions elicited during a polygraph test (Matte, 1980), a fine-grained analysis of different emotions and their concomitant psychophysiological responses has not been necessary for the practice of conventional interrogative polygraphy. Some go so far as to reject such analysis as irrelevant.

> First and foremost, it must be emphatically stated that the polygraph examiner is not concerned with attempting to differentiate one emotion from another. He is only concerned that a verbal stimulus did provoke an emotion which produced a sufficient nerve impulse to create a deviation from norm on the chart (Ferguson & Miller, 1973, p. 168).

The primarily empirical approach of conventional interrogative polygraphy is exemplified by Reid & Inbau (1977) in their authoritative text that has become perhaps the greatest classic in the field. They describe in voluminous detail the various psychophysiological responses that have proven in their extensive experience and that of other experts to be indicative of deception. They present a comprehensive and detailed account of the procedures that have been shown to be most effective in producing these responses; considerable knowledge about the art and science of interrogation aside from psychophysiological techniques; numerous case histories; a thoughtful discussion of legal, philosophical and moral issues; historical perspective; and reviews of research. The psychophysiological theory regarding the connection between the mind, emotions, and body that underlies psychophysiological detection of concealed information is only very briefly mentioned.

Although polygraphy has in general been practiced with a minimum of theoretical elaboration, there have been from time to time some notable exceptions to the rule. A number of scientists, some of them expert practicing polygraphers as well, have attempted to elaborate the emotional/physiological arousal paradigm for lie detection. Some have attempted also to bridge the gap between contemporary academic science and interrogative polygraphy as practiced.

In a classic paper on the subject, Davis (1961) outlined three specific theories for the psychophysiological response measured by conventional interrogative polygraphy. He called them the conditioned response theory, the conflict theory, and the threat-of-punishment theory. According to the conditioned response theory, "the critical questions play the role of conditioned stimuli, and evoke some 'emotional' response with which they have been associated in the past." One difficulty with the conditioning theory is that it is insufficient to explain psychophysiological responses to lying about rather trivial matters with which the subject has had no experience in the past, such as which number is on a card.

The conflict theory "would presume that a specially large physiologic disturbance would occur when two incompatible reaction tendencies are aroused at the same time." The assumption is that a subject has the habit of telling the truth, but in a situation necessitating deception to maintain his/her innocence the subject would simultaneously experience an opposite tendency.

The punishment or threat-of-punishment theory, which has more often been called the fear theory, is the working understanding on which conventional polygraphy is generally practiced (Reid & Inbau, 1977; Barland & Raskin, 1973). The fear theory holds that "a person will give a large physiologic response during lying because he anticipates serious consequences if he fails to deceive. In common language it might be that he fails to deceive the machine operator for the very reason that he fears he will fail. The 'fear' would be the very reaction detected." (Davis, 1961). To explain successful detection where the consequences are rather trivial, for example in the card test described above, one must interpret punishment rather broadly. Davis holds that perhaps the subject is psychologically "punished" by the detection of even trivial information.

Barland & Raskin (1973) describe another theory that they call the arousal theory. According to the arousal theory, "detection occurs because of the different arousal value of the various stimuli."

These elaborations of the basic theoretical foundation for interrogative polygraphy are not mutually exclusive. Moreover, it is likely that several different aspects of the psychophysiological phenomenon underlying conventional lie detection take place simultaneously (Davis, 1961; Barland & Raskin, 1973; Raskin, 1989).

Raskin (1979) hypothesizes that the response explained by the fear theory is primarily a defensive reflex, and the response explained by the arousal theory is primarily an orienting reflex. Which response is elicited depends on the interrogative situation in situations involving a relatively high level of emotion—particularly the response to relevant questions in a real-life application of the control question technique—the fear theory and the accompanying defensive response predominate. In situations involving a comparatively low level of emotion, the arousal theory and the accompanying orienting response predominate. Such low-emotion situations include mock interrogations, and especially mock interrogations using the guilty knowledge test. (Note that virtually all of the published results on the guilty knowledge test have been obtained in mock, laboratory situations.) The response to control questions has also been explained in terms of the arousal theory (Raskin, 1979).

The above hypothesis is in accord with research that has recorded somewhat different physiological responses in different lie detection situations. The electrodermal response is particularly effective in detecting the orienting reflex, and may be unstable in situations of very high emotion (Reid & Inbau, 1966). Cardiovascular and pulmonary responses, by contrast, are more marked in situations involving very high emotional levels. This may explain why Reid & Inbau (1966) found the cardiovascular and pulmonary measurements to be superior to the electrodermal measurement for field use, but not in the laboratory. (Note, however, that in the 1977 revision of their book, Reid and Inbau modified their conclusions to include a somewhat more favorable evaluation of the electrodermal response.) Other researchers (e.g., Podlesny & Raskin, 1977), on the basis of scientific studies many of which were laboratory studies involving mock crimes, concluded that the electrodermal response was superior. The predominance of the arousal theory in low emotion situations, combined with the fact that the guilty knowledge test has been studied almost exclusively in mock situations and is inherently less stressful than the control question test, may similarly explain the finding (Podlesny & Raskin, 1978; Balloun & Holmes, 1979; Bradley & Janisse, 1981; Iacono, Cerri, Patrick, & Fleming, 1987) that the electrodermal response is the most, and perhaps the only, effective measurement in the guilty knowledge test.

Different researchers have emphasized a different balance between the fear and arousal responses. Marston (1917; 1932) attempted to exclude the arousal response and focus on measurements that would emphasize the fear response. Ben-Shakar, Lieblich, and Kugelmass (1975), in a low emotion laboratory study on the guilty knowledge technique, attempted to minimize the fear response, and to obtain discrimination of knowledge on the basis of the arousal theory. They formulated the dichotomization hypothesis, which attempted to explain their results as differential habituation of the electrodermal response to different categories of stimuli (relevant and irrelevant).

There is no evidence in the scientific literature, however, that a guilty individual accused of a serious crime will fail to display a fear response when confronted during a guilty knowledge test with relevant details of the crime. On the contrary, anecdotal field experience (Keeler, 1930, p. 49) indicates a "violent emotional response." Nor is there convincing evidence that the arousal response can (or should) be entirely excluded in an actual interrogation situation (see Raskin, 1979, 1987). Fortunately, the proponents of the various points of view within the conventional paradigm agree that for practical purposes it does not matter. As long as the subjects' responses are different in magnitude to the different types of questions, the direction and specific details of the response are not crucial for distinguishing guilt from innocence. As Lykken (1959), a major proponent of the guilty knowledge test and severe critic of the control question test, noted in describing the guilty knowledge test, > A guilty subject would be expected to respond differently to the relevant than the irrelevant items. Usually, he would be expected to give larger responses to the relevant items, although it should be pointed out that any consistent difference in the responses to the two classes of stimuli is evidence of guilt.

Note that in this regard Lykken's view is very similar to that expressed by Ferguson & Miller (1973), supporters of the control question test, as quoted above in reference to that technique.

Conventional interrogative polygraphy, and in particular the control question test, have been criticized on a number of scientific, ethical, humanitarian, and legal grounds (Skolnick, 1961; OTA, 1983; Saxe, Dougherty, & Cross, 1985; Kleinmuntz & Szucko, 1982; Iacono, 1985;). There has been what might be termed a lively interchange of ideas between proponents of the different conventional polygraphy methods (see, for example, Lykken, 1978; Raskin, 1978; Barland, 1985; Horvath, 1985). Many of the harshest critics of the control question test are advocates of the guilty knowledge test (see, for example, Lykken, 1959, 1978, 1985, 1988; Furedy & Helsgrave, 1988; Ben-Shakhar, Bar-Hillel, & Lieblich, 1986), and the reverse is also true (Raskin, 1989). Criticisms range from a general statement that more research is needed to comparisons of control question polygraphy with the superstitious bone-pointing procedures used by Australian aborigines (Furedy, 1987). The evidence on the accuracy and validity of the conventional polygraphy is mixed, with estimates of accuracy ranging from chance to 100%. Both sides of the controversy (see, for example, Lykken, 1988; Raskin, 1988) conclude that the methodologically and theoretically sound studies support their point of view, whereas the studies purporting to support the opposite point of view are seriously flawed (Barland, 1985). There is general agreement that the quality and experience of the examiner have a significant effect on the outcome of a polygraph examination (Barland, 1988), although whether this is a strength or a weakness of the technique is a matter of debate. There also has been considerable controversy over who is qualified to speak with authority on interrogative polygraphy—experienced field polygraphers or academic scientists.

The current state of the emotional/physiological arousal paradigm for lie detection, then, is one of contradictions and controversy. Even the strongest proponents of the current paradigm acknowledge that it has both theoretical and practical weaknesses, while even its most vehement critics at least admit that conventional polygraphy has some degree of effectiveness in eliciting confessions from guilty subjects. In the next section I will compare the several applications of this paradigm that are currently in use, discuss their strengths and weaknesses, and contrast the current paradigm with the new paradigm reported herein.

Comparative Strengths and Weaknesses of the Conventional Techniques

The Relevant/Irrelevant Test

The fundamental weakness of the relevant/irrelevant technique is that the dimension of "relevant/irrelevant to this particular crime" is entirely confounded with the dimension of "having to do with any crime or undesirable activity (and consequently potentially upsetting)." This can result in either false positives or false negatives (Podlesny & Raskin, 1977). If a subject is particularly responsive to any mention of criminal or undesirable activity, then a false positive can result. If an individual is particularly unresponsive to such mention, then a false negative can result. Even many of the strongest supporters of conventional polygraphy now agree that the relevant/irrelevant test is seriously flawed (Raskin, 1979).

The control question test attempts to deal with this confound by introducing a class of questions, the control questions, which have to do with crimes or undesirable activities on the part of the subject, but are not relevant to the particular crime under investigation.

The Control Question Test

This aspect of control is the primary strength of the control question technique. In introducing an additional type of question, however, the control question test also inevitably introduces an additional source of variability. The control questions are never fully comparable to the relevant questions. Ordinarily, control questions are of a general nature and cover a long period of time. (For example, "Have you ever stolen anything from anyplace where you worked?") Relevant questions are often very specific. (For example, "Did you steal $200 from Smith's wallet last Tuesday?") A false negative may result if an individual responds excessively to questions of the type exemplified by the control questions. This can be a result of the examiner's choice of control questions, the psychological or physiological makeup of the subject, deliberate countermeasures, or any one of a number of other factors. If, for any of the above reasons, an individual tends to respond only slightly to the kind of questions of which the control questions are examples, then a false positive may result. Similarly, exceptionally large or small responses to specific crime-related questions can result in false positives or negatives respectively. These difficulties can be ameliorated by skillful interrogation and choice of control questions, but they are intrinsic to the design of the control question test and can never be eliminated entirely.

It is generally agreed by critics and supporters alike (OTA, 1983; Barland, 1985) that the control question test is more effective at discovering guilty subjects than at clearing innocent ones. This may be due, at least in part, to the fact that the relevant questions are recognized as such by both innocent and guilty subjects, and the relevant questions may tend to be inherently more upsetting than the control questions regardless of the guilt or innocence of the subject.

Another major difficulty of the control question test is that it can, and in fact in order to be successful it must, subject an innocent subject to considerable stress and negative emotional arousal. In the case of a guilty subject in an actual criminal interrogation, field experience indicates that the relevant questions are highly stressful in both the control question test (Gugas, 1979) and the guilty knowledge test (Keeler, 1930). It may be argued, however, that this stress is a result of the subject's criminal activity, rather than the test per se, and that a similar level of stress would inevitably be incurred in any interrogation of a guilty subject. For an innocent subject, however, there are two additional sources of stress in the control question test. The relevant questions, particularly if the crime is serious, may be experienced as highly stressful. Moreover, the control questions are designed to elicit a similar response in all subjects to the response to relevant questions in a guilty subject. Since the responses to the relevant and control questions are compared to make the determination of guilt or innocence, an innocent subject, in order to pass the test, must exhibit larger responses to the control questions than to the relevant questions. This means that the control questions must be designed to produce an even larger response than questions that falsely accuse a subject of a real crime.

Munsterberg (1908), one of the earliest modern advocates of the emotional/physiological arousal paradigm for lie detection, summarized its limitations perhaps as eloquently as anyone since.

... experiment gives us so far not sufficient hold for the discrimination of the guilty conscience and the emotional excitement of the innocent. The innocent man, especially the nervous man, may grow as much excited on the witness stand as the criminal when the victim and the means of the crime are mentioned; his fear that he may be condemned unjustly may influence his muscles, glands and blood vessels as strongly as if he were guilty. Experimental psychology cannot wish to imitate with its subtle methods the injustice of barbarous police methods. The real use of the emotion-method is therefore so far probably confined to those cases in which it is to be found out whether a suspected person knows anything about a certain place or man or thing.

The Guilty Knowledge Test

The greatest strength of the guilty knowledge test is that an innocent subject cannot distinguish between the relevant and irrelevant items. This avoids a major source of false positives that occur with the control question test: that an innocent subject is emotionally aroused by the inherently upsetting and clearly recognizable relevant questions. In a properly structured guilty knowledge test, only a guilty subject can recognize the relevant questions as such, and consequently an innocent subject is unlikely to respond differentially to the relevant items (Lykken, 1988). The fact that the innocent subject does not know which are the relevant questions, the absence of accusatory relevant questions, and the lack of intentionally disturbing control questions also make the guilty knowledge test less stressful for an innocent subject than the control question test.

The major weakness of the guilty knowledge test is its lack of control. If a subject does not respond to the relevant questions, there may be at least two different explanations: 1) the subject is innocent, and is not responding to the relevant stimuli because they are no different to him than the irrelevant stimuli, or 2) the subject is guilty, but for some physiological or psychological reason does not show a differential response to questions relevant to his guilt. The guilty knowledge test does not allow a distinction between these two possibilities. If the subject does not respond, there is no way of determining what it would have taken to make him respond. This feature makes the guilty knowledge test particularly susceptible to false negatives (Raskin, 1988). (Note that the ERP-based test reported here does not suffer from this weakness. The "target" stimuli provide a control response that is lacking in the conventional guilty knowledge test).

Another weakness of the guilty knowledge test is that it necessitates knowledge of the details of the crime on the part of the examiner. In practice, this means that considerably more time and effort must be invested by an interrogator in the investigation. In some cases the guilty knowledge test can not be applied at all. For example, the investigators may be unable to obtain sufficient information to structure a test based on guilty knowledge; or a subject may admit being present at the crime scene but maintain that he or she was a witness or that no crime occurred..Another difficulty is that special care must be taken not to provide the suspect with critical information during interrogation prior to the test.

Because of these difficulties, the conventional guilty knowledge test has not been widely implemented in actual investigations in the United States. In Japan and Israel, however, it is much more widely employed.

Both the strengths and the weaknesses of the peak of tension technique are similar to those of the guilty knowledge technique.

Of course, the skill of the examiner is an important factor in the effectiveness of all conventional interrogative polygraphy techniques. Only a highly skilled examiner can use any of these techniques effectively (Reid and Inbau, 1977; Raskin, 1988).Each of the conventional techniques, however, suffers from particular inherent difficulties. Moreover, all of them suffer from some common difficulties derived from their dependence on the interactions between emotions and the autonomic nervous system.

The Autonomic Nervous System in Interrogative Polygraphy

All previous approaches to interrogative polygraphy are based on the assumption that a deceptive action on the part of the subject will be accompanied by an affective reaction. (For reviews, see Furedy, 1986; OTA, 1983; Department of Defense, 1984; Kircher, Horowitz, & Raskin, 1988; Raskin, 1987, 1988, 1990; Lykken, 1988). This reaction, in turn, is associated with activity in the autonomic nervous system, an activity that is manifested by an ensemble of actions generated within a variety of effectors driven by the autonomic nervous system. Some of these actions can be detected by monitoring several biological systems whose activity is modulated by the autonomic nervous system.

The use of affective responses in the detection of deception suffers from a number of inherent difficulties. All conventional detection of deception techniques depend on 1) the examiner's ability to create a situation that will effectively elicit particular emotions in the subject—and in particular, different patterns or levels of emotional arousal in innocent and guilty subjects—in the course of an interrogation, 2) the subject's emotional responses, 3) the subject's physiological responses when these emotions are aroused, 4) accurate measurement of these physiological responses, and 5) the examiner's interpretation of these physiological measurements.

Difficulties with Autonomic Nervous System-Based Polygraphy

Even if it is assumed that autonomic nervous system responses can be accurately measured and that the examiner will bring to the interpretation of these measurements a high level of expertise, a number of difficulties inevitably arise in drawing inferences about the guilt or innocence of a subject based on the above sequence of events. A researcher or interrogator is never certain that even a carefully structured and effectively executed interrogation will differentially elicit the requisite level of emotional arousal at the appropriate times. Subjects may exhibit unpredictable, unusual, or unexpected emotional responses (or lack of responses), or may manipulate their emotions to avoid detection. Some types of individuals (e.g., psychopaths) may not exhibit the emotions usually found. Different individuals may exhibit similar emotions for different reasons. For example, two individuals may be equally fearful in response to a particular item, one because he committed a crime and is afraid of detection and another because he did not commit the crime and is afraid of being falsely convicted.

Even if the emotional responses are as predicted and desired, autonomic nervous system responses may not be. Subjects may control their physiological responses voluntarily or through drugs, may employ hidden techniques (e.g., biting the tongue) to bring about misleading responses, or may naturally have unusually large or small autonomic nervous system responses or idiosyncratic patterns of electrodermal response, breathing, or cardiovascular activity. The difficulty in inferring emotions from their autonomic nervous system "correlates" is well known.

As has been reported in many studies of interrogative polygraphy, false positives are often the consequence of an affective response to a question, or to the presentation of an item, for reasons that have little or nothing to do with deception (Lykken, 1974, 1978). Conversely, false negatives often result from the absence, or the low amplitude, of an autonomic nervous system manifestation of an affect.

It is also the case that only a portion of the variance in the autonomic nervous system activity is driven by affective processes. The autonomic nervous system is charged with the regulation of the most vital of the body's functions, and changes in heart rate, blood pressure, respiration and sweat gland activity reflect a variety of non-affective demands by the system. These include, for example, varying demands for blood supply, variations in the need for oxygen, and modulations of body temperature. From the point of view of interrogative polygraphy the autonomic nervous system is quite a noisy system. The "signal," that is, the autonomic nervous system activity driven by affect, may be swamped or masked by the "noise," the autonomic nervous system activity that is related to the vegetative and energetic functions of the system.

These factors are, in part, responsible for the ability of individuals to modify autonomic nervous system at will. The susceptibility of the autonomic nervous system for control using biofeedback makes it even more vulnerable, especially for specially trained individuals, to voluntary control by the subject. Countermeasures may range from the voluntary generation of affect by cognitive control to the activation of bodily parts so as to create energy needs that will be reflected in autonomic nervous system responses at critical points in the polygraph examination.

SUMMARY OF THE INVENTION

A method of detecting information stored in the brain of a subject includes presenting to the subject in oddball series Probe, Target, and Irrelevant stimuli. The Probe stimuli are relevant to a situation under investigation; the Irrelevant stimuli are not; and the Target stimuli are identified to the subject as being noteworthy, and in response to which the subject is instructed to perform a task. The Target stimuli like the Probe stimuli are relevant to the situation under investigation. The method also includes detecting electrical brain responses for each of the stimuli; analyzing the responses for uncovering an event related brain potential; and comparing the Probe responses with the Target responses to determine whether the subject recognizes the Probes, and comparing the Probe responses with the Irrelevant responses to determine whether the subject does not recognize the Probes. Three exemplary headbands are disclosed for positioning electrodes at preferred locations on the subject's scalp for obtaining electrical responses therefrom.

BRIEF DESCRIPTION OF THE DRAWINGS

FIG. 9 is a schematic showing the layout of the posterior side of the basic headband, that is, the side which contacts the subjects head. It indicates placement of each relevant electrode (Fz, Cz, Pz, EOG, left and right mastoids, and ground), Velcro loop pads, and connector on this side of the headband.

FIG. 10 is a schematic of the layout of the anterior side of the basic headband, that is, the side which faces out when the headband is worn. It indicates placement of Velcro hook pads.

FIG. 13 is a schematic of the posterior side of the "Velcro-sizing" headband, showing electrode and Velcro placement as in the basic headband.

FIG. 14 is a schematic of the anterior side of the "Velcro-sizing" headband, showing the concept and placement of the Velcro-sizing hook flaps and loop pads placed behind each electrode site, as well as the basic Velcro hook pads for overall headband fastening.

DESCRIPTION OF THE PREFERRED EMBODIMENTS

Figure 1:
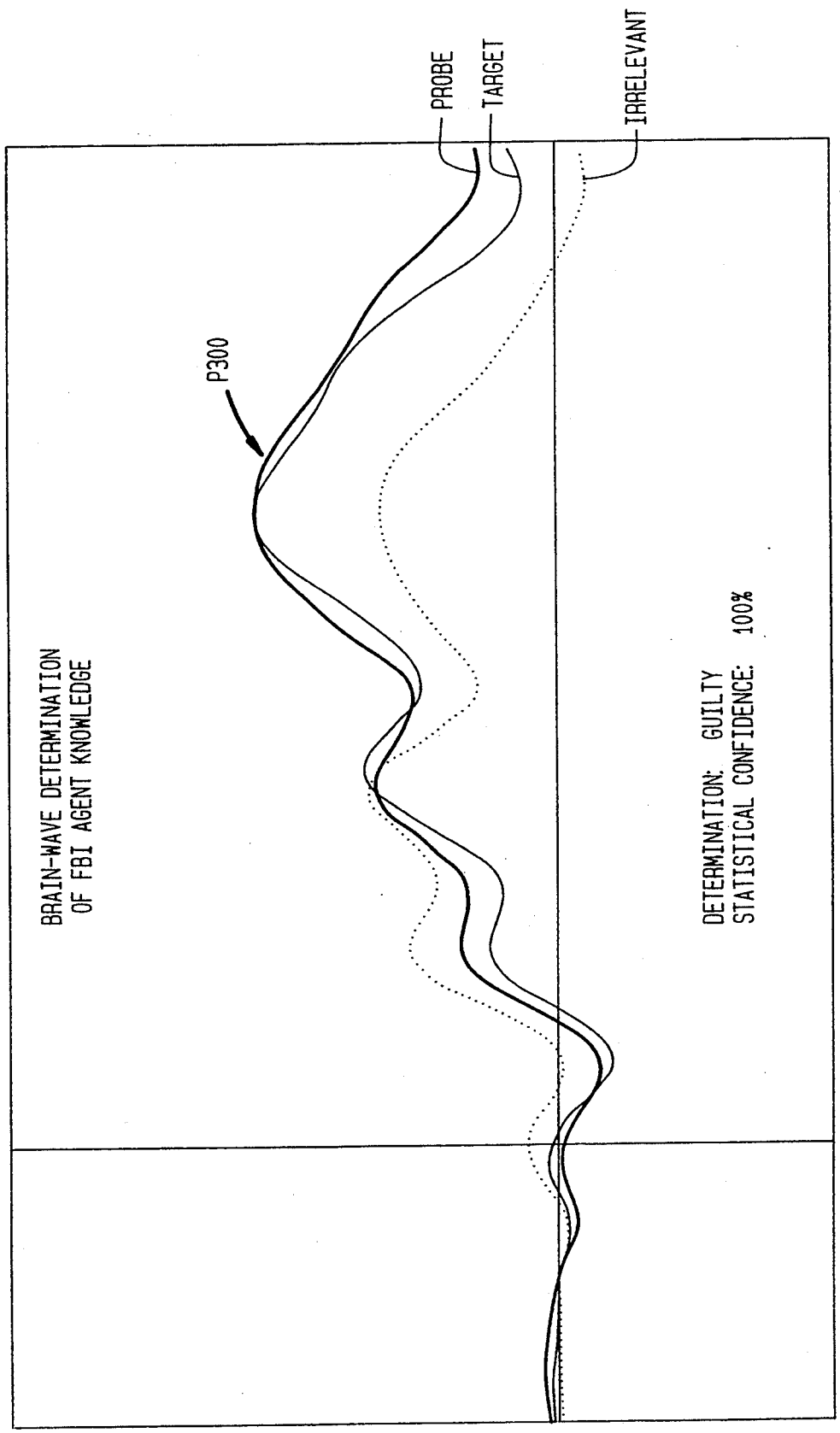
FIG. 1 is a graph of Brain-wave Determination of FBI Agent Knowledge which plots Probe, Target, and Irrelevant P300 brain responses.

The detection of concealed information stored in the brain of suspects, witnesses, intelligence sources, and others is of central concern to all phases of law enforcement and intelligence operations. The Farwell system for event-related brain potential psychophysiological detection of concealed information presents a new paradigm in the detection of concealed information. This new system detects information directly, on the basis of the electrophysiological manifestations of information-processing brain activity, measured non-invasively from the scalp. Since the Farwell system depends only on brain information processing, it does not depend on the emotional response of the subject.

The Farwell system utilizes the differential! elicitation of the P300 component of the event-related brain potential to detect information stored in the human;-brain. The P300 is elicited when an individual recognizes and processes an incoming stimulus that is significant or noteworthy. When an irrelevant stimulus is seen, the P300 is absent. This pattern occurs within less than a second after the stimulus presentation, and can be readily detected using EEG amplifiers and a computerized signal-detection algorithm.

The Farwell system incorporates the following procedure. A sequence of words, phrases, or pictures is presented on a video monitor under computer control. Each stimulus appears for a fraction of a second. Three types of stimuli are presented: "targets," "irrelevants," and "probes." The targets are made relevant and noteworthy to all subjects: the subject is given a list of the target stimuli and instructed to press a particular button in response to targets and another button in response to all other stimuli. Since the targets are noteworthy for the subject, they elicit a P300. Most of the non-target stimuli are irrelevant, having no relation to the situation under investigation. These irrelevants do not elicit a P300. Some of the non-target stimuli are relevant to the situation under investigation. These relevant stimuli are referred to as probes. For a guilty subject, the probes are noteworthy due to the subject's knowledge of that situation, and therefore probes elicit a P300 when the subject is guilty (or "knowledgeable"). Probes are indistinguishable from the irrelevants for an innocent subject, and thus probes do not elicit a P300 if the subject is innocent.

The entire Farwell system is under computer control, including presentation of the stimuli and recording of electrical brain activity, as well as a mathematical data analysis algorithm that compares the responses to the three types of stimuli and produces a determination of "innocent" or "guilty," and a statistical confidence level for this determination.

Dr. Lawrence A. Farwell, Director and Chief Scientist of the Human Brain Research Laboratory (HBRL), Potomac, Md. and his colleagues have tested this system on mock crimes and actual minor crimes over the last several years with support from the United States Government. The system produced a determination with a high level of statistical confidence in 87.5% of the cases studied. 100% of the determinations were correct. A pilot study conducted by DR. Farwell in collaboration with SSA Drew C. Richardson, PH.D., FSRTC, Laboratory Division, FBI applied the Farwell system in the detection of FBI new agent trainees using FBI-relevant probes. The system correctly classified 100% of the FBI new agents tested, as well as several subjects who were "innocent" of any knowledge regarding the FBI.

A more recent study still underway has shown the Farwell Truth Detector to be effective in detecting knowledge regarding a mock espionage scenario utilizing pictorial stimuli, rather than words.

The Farwell system has potential application in a wide range of law enforcement and intelligence operations, from detecting whether a suspect has knowledge that would identify him as the perpetrator of a crime to detecting whether an individual has knowledge that would indicate that he had undergone training by a foreign intelligence organization.

I. Introduction

This report describes new and potentially revolutionary technology for the detection of concealed information that revolves around the non-invasive recording of brain electrical activity. The electrical brain activity pattern recorded and of interest is a specific event related brain potential (ERP) response which occurs approximately three tenths of a second after an examinee is visually presented (via a computer screen) with words, short phrases, acronyms, or pictures that are recognized and cognitively processed by that subject. This phenomenon, coupled with its absence following the presentation of the same information to a subject for whom the material is unknown or irrelevant, is the basis for discriminating between subject guilt and innocence. This would potentially allow for the determination of a whole host of issues of interest to the law enforcement and intelligence communities, e.g., (1) does a suspect have guilty knowledge connecting him to specific investigated criminal activity, (2) does an intelligence source have knowledge of the internal workings of a hostile intelligence agency that would indicate that he was an intelligence officer of that agency and not who he claimed to be, (3) has an informant, a debriefed spy, or a suspected member of a criminal organization accurately described the entirety of his actions and knowledge, (4) did a convicted serial killer who claims to have killed 40 to 50 individuals, other than the one(s) he was convicted of, actually commit these acts, or are these claims merely the bravado of a condemned prisoner.

The potential benefit of this program extends to a broad range of law enforcement applications, including organized crime, violent crime, white-collar crime, drug-related crime, foreign counterintelligence, non-traditional targets, and other categories of casework as well. This new technology promises to be of tremendous benefit both at the national level and for state and local law enforcement agencies.

This document proposes testing and implementation of a revolutionary technology that is capable of detecting concealed information stored in the brain through the electrophysiological manifestations of information-processing brain activity. Previous research conducted by Dr. Lawrence Farwell and his colleagues, and sponsored by the Central Intelligence Agency (CIA), has shown this technique to be highly accurate in distinguishing guilty and innocent individuals in mock crimes and actual minor crimes. Research conducted by Dr. Farwell in collaboration with SSA Drew C. Richardson, PH.D., FSRTC, Laboratory Division, FBI indicates that the system is also effective in distinguishing between members of a particular organization (in this case, the FBI) and others who are not knowledgeable regarding that organization.

When a crime is committed, traces of the event are left at the scene of the crime and elsewhere. The task of the investigators is to reconstruct what has happened and who has been involved, based on the collection of such evidence.

In addition to the physical and circumstantial evidence that can be obtained, there is one place where an extensive record of the crime is stored: in the brain of the perpetrator. If this record could be tapped, criminal investigation and counterintelligence could be revolutionized.

Until recently, the only method of attempting to discern what information regarding a crime or other situation of interest was stored in the brain of a suspect or witness has been 1) to interrogate the subject, and 2) to attempt to determine whether or not the subject is lying.

Conventional control question (CQT) polygraphy has been used as an aid in the attempt to detect deception in such reports. The fundamental theory of conventional polygraphy is that a deceptive individual will be more concerned with and experience more emotional arousal in response to relevant questions than control questions, and this emotional arousal will be accompanied by corresponding physiological arousal which can be measured. Traditional interrogative polygraph ("lie detection") methods rely upon using questioning formats in conjunction with the recording of physiological parameters that reflect autonomic nervous system (ANS) activity (e.g. blood pressure, heart rate, sweating, etc.). This information is peripheral to the cognitive aspects of deception or of concealing guilty information.

Event-related brain potential (ERP) technology presents the possibility of focusing on the origins (at the level of subject recognition of guilty knowledge) of concealed information rather than the peripheral physiological manifestations of that knowledge. In addition to being a more direct physiological approach (central nervous system vs. peripheral) to the question at hand, the Farwell system may well overcome certain difficulties inherent with standard polygraphy: (1) Innocent as well as guilty individuals may respond emotionally and physiologically to crime-relevant questions, (2) guilty individuals may fail to respond in the expected way either emotionally or physiologically, (3) certain mental and physical countermeasures can be practiced successfully with standard technology, and (4) the setting of control question material is an unpleasant task for the examiner and a highly unpleasant experience for the innocent examinee. This latter shortcoming is generally justified by the correct end result of finding an innocent subject non-deceptive to the relevant questions, but could be avoided altogether with event-related brain potential technology which depends entirely on cognition (i.e., recognition and processing of significant information) rather than an artful and unpleasant manipulation designed to produce emotional and physiological responses to control question material. In fact, the pretest interview for an event-related brain potential based exam is a very clinical, emotionally neutral experience for both guilty and innocent subjects. The in-test portion of the event-related brain potential based exam does not involve the asking of any questions, only the non-invasive recording of brain electrical activity as a subject views verbal or pictorial information on a computer screen.

Dr. Farwell, the Director and Chief Scientist of the Human Brain Research Laboratory in Potomac, Md., and his colleagues have been conducting research on this new technique for several years with funding from the Central Intelligence Agency. This research has been reviewed in a technical report prepared by Dr. Farwell for the Central Intelligence Agency, in U.S. Pat. No. 4,941,477, and in reports published in refereed scientific journals. Laboratory results have shown the Farwell technique to be capable of producing an "innocent" or "guilty" determination, with a strong statistical confidence, in approximately 90% of the cases studied. All of the determinations were accurate: there were no false positives and no false negatives. The cases studied included actual minor crimes and other real-life events as well as mock crimes.

Initial pilot studies conducted by Dr. Farwell in collaboration with SSA Drew C. Richardson, Ph.D., FSRTC, FBI Laboratory, have also shown promise for detecting whether or not an individual has participated in FBI new agent training at the Academy. New FBI agents in training at the FBI Academy at Quantico were correctly identified as such, and individuals unfamiliar with the FBI were also correctly classified. The application of this technique in foreign counterintelligence is obvious: if this technology can be utilized to detect an FBI agent, it can also be used to detect agents of other organizations, including both intelligence organizations and international criminal organizations.

The detection of information stored in the brain is central to the investigation of all types of crimes—e.g, organized crime, violent crime, white-collar crime, drug-related crime, industrial espionage, non-traditional targets—as well as foreign counterintelligence operations. The far reaching implications of possessing technology to accomplish this end are obvious. With the potential availability of such technology, it is felt imperative that this methodology be further tested as soon as possible, that the research and development necessary to make this a practical technique for field use be undertaken immediately, and that the technique be implemented as soon as possible by law enforcement agencies, if and when found valid and feasible. This proposal is the first step in making this new technique and technology available not only to the FBI and other national agencies, but also potentially to state and local law enforcement agencies.

II. Overview of the Farwell System:

Instrumental Requirements and Event-related Brain Potentials

The experimental design for the studies in this report is based on original research described in a technical report produced by DR. Farwell for the CIA and in a scientific journal publication (Farwell, 1991; Farwell and Donchin, 1991). Fundamental to this design is the "oddball" experimental procedure. In this procedure, a series of stimulus events is presented to a subject. Some of the events (the "oddballs") are relatively rare, and in response to these events the subject is required to perform a task (e.g., push a button). Extensive research has shown that these rare, task-relevant stimuli elicit an event-related brain potential characterized by a P300 component. The P300 is an electrically positive component, maximal at the midline parietal scalp, with a latency in excess of 300 msec. It can be readily recognized through signal averaging procedures.

The equipment required for the Farwell system consists of a personal computer (e.g., 486 - 50 MHz Gateway 2000), a data acquisition board (e.g., Scientific Solutions Lab Master AD), a graphics card for driving two monitors from one PC (e.g., Colorgraphics Super Dual VGA), a four-channel EEG amplifier system (e.g., Neuroscience), and the software developed by the Human Brain Research Laboratory (HBRL) for data acquisition and analysis. The electrodes used to measure electrical brain activity are held in place by a special headband designed and constructed by the Human Brain Research Laboratory for this purpose. (This new method for attaching electrodes is more convenient and comfortable for the subject as well as quicker and easier for the operator than previously available methods.)

In most of the past and planned experiments using the Farwell system, visual stimuli consisting of short phrases are presented on a video screen under computer control. (Pictures have also been employed.) Three categories of stimuli are presented: "probes," "targets," and "irrelevants."

Probes are stimuli relevant to the crime under investigation. Irrelevants are, as the name implies, irrelevant. For each probe stimulus, there are approximately four irrelevant stimuli. The stimuli are structured such that the probes and irrelevants are indistinguishable for an innocent subject. That is, if a given probe is an article of clothing relevant to the crime, four articles of clothing irrelevant to the crime are also presented; if a particular probe stimulus is a name, there are four irrelevant stimuli that are also names, and so on.

In addition to the probes and the irrelevants, a third type of stimuli, designated as targets, is presented. About one-sixth of the stimuli are targets, one for each probe. The subject is given a list of the targets, and is required to press a particular button whenever a target is presented. (For all other stimuli, the subject is instructed to press another button.) Thus, the targets constitute a rare (probability of 1/6) and task-relevant (button press) stimulus, and therefore will elicit a P300 component in the brain response. Each target is the same type of item as one of the probes and the several corresponding irrelevants.

For an innocent subject, then, this is simply an ordinary oddball task. He recognizes only two types of stimuli: rare, relevant targets and frequent, irrelevant stimuli (consisting in fact of true irrelevants, plus probes—which he does not distinguish as being different from the irrelevants). The targets elicit a P300, and the irrelevants and (unrecognized) probes do not.

A guilty subject, however, recognizes a second rare, relevant type of stimuli, namely the probes, which are relevant to a crime or other situation in which he has participated. Thus, for a guilty subject, the probes, too, elicit a P300.

What this experimental design accomplishes, essentially, is to create one oddball series for an innocent individual, and two oddball series (with the same stimuli) for a guilty individual. The targets provide a template for a response to stimuli known to be rare and relevant—P300-producing stimuli. The irrelevants provide a template for a response to stimuli that are frequent and irrelevant—non-P300-producing stimuli.

The determination of guilt or innocence consists of comparing the probe responses to the target responses, which contain a P300, and to the irrelevant responses, which do not. If the probe responses are similar to the target responses, one can conclude that the subject recognizes the probes—which only someone knowledgeable about the crime would do—and therefore is "guilty" (or, more correctly, "knowledgeable"). If the brain responses to the probes are like those to the irrelevants—i.e., lacking a P300—then the subject can be determined to be "innocent." (Note that what is detected is not actually guilt or innocence, but knowledge or lack of knowledge regarding the situation under investigation. In order for this to be an effective indicator of guilt or innocence, stimuli must be structured such that only a guilty person would recognize the probe stimuli.) The statistical technique of bootstrapping is employed to compare the brain responses to the different types of stimuli, to make a determination of "innocent" or "guilty," and to provide a statistical confidence for this determination.

Table 1 summarizes the three types of stimuli presented and the predicted brain responses to each type of stimulus.

III. Results of Recent Research

The following pages present abstracts of recent presentations and publications of research on the Farwell system. The results are presented in the same format as they were published or presented in scientific meetings.

Professional Profiles: Event-related Potential Detection of Concealed Occupational Information in FBI Agents Lawrence A. Farwell Abstract of an address presented at the Annual Meeting of the American Polygraph Association, Orlando, Fla., August, 1992.

Previous research used a brain-wave-based "Truth Detector" system (Farwell, 1991; see also Farwell, 1992; Farwell & Donchin, 1986, 1991) to detect guilty knowledge regarding real and mock crimes. Three types of stimuli were used: crime relevant "probes," "irrelevant" stimuli, and "targets," a subset of non-crime-relevant stimuli in response to which a particular button press was required. P300s were elicited by the rare, relevant stimuli: targets for all subjects, and both targets and probes for guilty subjects. Comparison of the brain-wave responses using a mathematical bootstrapping algorithm produced a guilty or innocent determination and a statistical confidence for the same. The present study introduces two innovations: 1) what is detected is not guilty knowledge regarding a specific incident, but rather a more generalized class of information that would be possessed only by individuals with particular occupational knowledge or professional expertise; and 2) the targets are a subset of the relevant stimuli. Targets, as before, have been identified to the subject, and a unique task is required in response to them. The potential application is to identify individuals who possess a specific type of background information (e.g., military or intelligence expertise).

In a pilot study, seven FBI agents and four control subjects were presented with short phrases and acronyms on a video screen. ⅓ of the stimuli were relevant to the FBI; ⅔ were irrelevant. Half of the relevant stimuli were identified to the subjects as targets. Subjects were instructed to push one button to targets, and another button to all others. The non-target relevant stimuli served as probes. All FBI agent subjects exhibited large P300s both to targets and probes, and not to irrelevants, indicating that they possessed the profession-specific knowledge sought. Bootstrapping yielded a correct ("guilty") determination with at least a 90% confidence in every case. "Innocent" (non-FBI knowledgeable) subjects exhibited a large P300 only to the targets. Bootstrapping yielded a correct "innocent" determination (bootstrap index $>0.70$) in every case.

Illustrated in FIG. 1 are average ERP brain responses recorded from an FBI new agent in response to three types of stimuli: 1) Targets are phrases which are made relevant to the subject by requiring him/her to push a particular button when they appear. Note the large P300, which indicates that these stimuli are relevant to the subject. 2) Irrelevants are phrases that are not relevant. The P300 response is lacking. 3) Probes are FBI-relevant phrases that the subject gives no overt indication of recognizing. Note the large P300, indicating that these FBI-relevant stimuli are relevant to this subject. A subject unfamiliar with FBI training would not recognize these stimuli as significant, and would not display a P300 response to them. Thus, it can be determined that this subject is an FBI agent (defined in this study as a "Guilty" determination).

Two New Twists on the Truth Detector: Event-related Brain Potential Detection of Occupational Information Lawrence A. Farwell Abstract of an address presented at the Annual Meeting of the Society for Psychophysiological Research, October, 1992, San Diego, Calif.

Previous research introduced a new paradigm in psychophysiological detection of concealed information: a brain-wave-based "Truth Detector" system (Farwell, 1991; see also Farwell, 1992; Farwell & Donchin, 1986, 1991) to detect guilty knowledge regarding real and mock crimes. Stimuli consisted of short phrases presented visually. Three types of stimuli were presented: "probes," "targets," and "irrelevants." Probes were relevant to the crime in question. Irrelevant stimuli were, of course, irrelevant to the crime. Targets were also irrelevant to the crime; however, the occurrence of a target required performance of a unique task. Subjects were given a list of the targets, and instructed to push a button under one thumb in response to targets and another button in response to all other stimuli. P300s were elicited by the rare, relevant stimuli: targets for all subjects, and both targets and probes for guilty subjects. Comparison of the brain-wave responses using a mathematical bootstrapping algorithm produced a "guilty" (knowledgeable regarding the crime in question) or "innocent" determination and a statistical confidence for each individual case.

The present study introduces two innovations to this new paradigm: 1) what is detected is not guilty knowledge regarding a specific incident, but rather a more generalized class of information that would be possessed only by individuals with a particular occupation; and 2) the targets are a subset of the relevant stimuli. (As before, targets have been identified to the subject, and subjects are required to perform a unique task—a particular button press—in response to the targets.)

The potential application is to identify individuals with a specific type of background information (e.g., military or intelligence expertise).

Seven FBI agents and four employees of the Human Brain Research Laboratory were presented with short phrases on a video screen. Stimulus duration was 300 msec; stimulus onset asynchrony was 1550 msec. ⅓ of the stimuli were relevant to the occupation of the subjects; ⅔ were irrelevant. Half of the relevant stimuli were identified to the subjects as targets. Subjects were instructed to push one button in response to targets, and another button in response to all other stimuli. The non-target, relevant stimuli (p=1/6) served as probes. All subjects exhibited large P300s in response to both targets and probes, and not to irrelevants, indicating that they possessed the occupation-specific knowledge that the test was designed to reveal. The bootstrapping statistical algorithm yielded a correct ("guilty") determination with at least a 90% confidence in every case. Four subjects "innocent" of occupation-specific knowledge relevant to the FBI were also correctly classified.

Two New Twists on the Truth Detector

Lawrence A. Farwell

Published in: Psychophysiology, 29,4A:S3

Previous research used a brain-wave-based "Truth Detector" system (Farwell, 1991; see also Farwell, 1992; Farwell & Donchin, 1986, 1991) to detect guilty knowledge regarding real and mock crimes. Three types of stimuli were used: crime relevant "probes," "irrelevant" stimuli, and "targets," a subset of non-crime-relevant stimuli in response to which a particular button press was required. P300s were elicited by the rare, relevant stimuli: targets for all subjects, and both targets and probes for guilty subjects. Comparison of the brain-wave responses using a mathematical bootstrapping algorithm produced a guilty or innocent determination and a statistical confidence for same.

The present study introduces two innovations: 1) what is detected is not guilty knowledge regarding a specific incident, but rather a more generalized class of information that would be possessed only by individuals with a particular occupation; and 2) the targets are a subset of the relevant stimuli that have been identified to the subject and in response to which a unique task is required.

The potential application is to identify individuals with a specific type of background information (e.g., military or intelligence expertise).

Four employees of the Human Brain Research Laboratory, were presented with short phrases on a video screen. ⅓ of the stimuli were relevant to the occupation of the subjects; ⅔ were irrelevant. Half of the relevant stimuli were identified to the subjects as targets. Subjects were instructed to push one button to targets, and another button to all others. The non-target relevant stimuli served as probes. All subjects exhibited large P300s both to targets and probes, and not to irrelevants, indicating that they possessed the occupation-specific knowledge sought. Bootstrapping yielded a correct ("guilty") determination with at least a 90% confidence in every case.

Farwell (1992) proposed a new paradigm for the psychophysiological detection of concealed information. The conventional "lie detector" has traditionally relied upon measurements of the physiological concomitants of emotional arousal. The new paradigm introduces a "Truth Detector"13 or, more precisely, "Information Detector"—system that measures the event-related brain potential manifestations of information-processing brain activity. Much of the material presented here is also included in Farwell (1992; see also Farwell & Donchin, 1986; 1991).

This report describes the original studies that founded the new paradigm, as well as an ongoing series of experiments currently underway at the Human Brain Research Laboratory. The report will be updated periodically as results are obtained in the ongoing research program.

In the original three experiments, the new Farwell Truth Detector was tested in 56 cases. In 100% of the cases where a determination was made, determinations were correct; 14% were indeterminate.

This research is based on the P300 component of the event-related brain potential, which is elicited by events that are relatively rare and relevant or noteworthy.

In each experiment, three types of short phrases were presented on a video screen for 300 msec at an interstimulus interval of 1550 msec. 17% of the stimuli were "target" stimuli, identified as such to the subject. Subjects were instructed to press one button in response to targets, and another button for all others. 66% were "irrelevant" stimuli, which had no particular significance for the subject. Interspersed with the irrelevant stimuli, and not identified in instructions to the subject, were "probe" stimuli which were relevant to a real or mock crime that had been in some cases committed by the subject. 17% were probes. For innocent subjects, probes were indistinguishable from irrelevants.

P300s were predicted in response to only the rare, relevant stimuli: targets for "innocent" subjects, and targets and probes for "guilty" (knowledgeable) subjects.

One experiment tested subjects on mock crimes, one on minor crimes confessed to by subjects, and one on real-life activities of subjects that had not been discussed with them. Results were as predicted. "Guilty" or "innocent" determinations were made through a mathematical algorithm comparing brain-wave responses.

The history and scientific foundations of psychophysiological detection of concealed information are reviewed and evaluated. The theory and practice of the new and conventional paradigms are compared. The implications of this research for theories of the functional significance of event-related brain potentials are discussed.

METHOD

Short phrases or pictures are presented to a subject on a video monitor under computer control. Stimulus duration is relatively brief, e.g., 300 msec, and interstimulus interval is about 1 or 2 seconds from the onset of one stimulus to the next stimulus onset.

Brain electrical activity is recorded from three midline electrode sites on the head: frontal (Fz), central (Cz) and parietal (Pz), referenced to linked mastoids (behind the ear). Eye movement generated electrical activity is recorded by electrodes above and below one eye.

Brain electrical activity is amplified, analog filtered (e.g., low-pass 30 Hz, high pass 0.02 Hz) digitized at 100 Hz, analyzed on-line, and stored on tape or disk. Each trial consists of the brain activity recorded in conjunction with one stimulus presentation, about 1 to 2 seconds of data.

Three types of stimuli are presented:

1) Probe stimuli consisting of information relevant to a crime or situation under investigation.

2) Irrelevant stimuli that are not relevant to the situation. About 4 irrelevant stimuli are presented for each probe. These are designed to be indistinguishable from the probe for an innocent person. (For example, if the probe stimulus were a name, the irrelevant stimuli would also be names; if the probe were an item of clothing, the irrelevants would also be items of clothing.)

3) Target stimuli, one for each probe. These are not relevant to the situation under investigation, but are made relevant to the subject by experimental instructions. Like the irrelevants, each target is designed to be of the same category as a particular probe. The subject is given a list of the target stimuli, and instructed to push a button under one thumb whenever a target appears, and to push a button under the other thumb when any other stimulus appears.

Without the "guilty knowledge" regarding the event in question, the probes are indistinguishable from the irrelevants. Without the experimental instructions, the targets are indistinguishable from the irrelevants.

The full set of stimuli, consisting of all three stimulus types, is randomized, and the stimuli are presented to the subject one at a time on the video monitor. Typically, there are about 6 probes, 6 targets, and 24 irrelevants. Once all of the stimuli have been presented, they are randomized again and presented again. This is repeated until a specified number of trials have been presented, or until a sufficient number of artifact-free trials have accumulated. The required number of artifact-free trials may be for the total and/or for the number of trials of one or more of the 3 types.

The P300 component of the event-related brain potential is a positive-going electrical potential with a latency of at least 300 msec, generally maximal at the Pz site, that is elicited by events that are relatively rare and are noteworthy or relevant to the subject. For all subjects, the targets are both rare (comprising about 1/6 of the stimuli) and task relevant. Therefore targets can be expected to elicit a P300 for all subjects. For all subjects, the irrelevants are frequent and irrelevant, and therefore are not expected to elicit a large P300. For an innocent subject, the probes are indistinguishable from the irrelevants, and are not expected to elicit a large P300. For a guilty subject, however, the probes form a second rare and relevant category in addition to the targets—namely, stimuli that are relevant to a known event—and so they, too, elicit a P300.

The task in data analysis is to compare the probe, target, and irrelevant responses. If the probe responses are similar to the irrelevants (no P300), then the subject does not distinguish the crime-relevant items, and is determined to be innocent. If the probe responses are similar to the target responses (large P300), then the subject is distinguishing the crime-relevant stimuli as such, which only a guilty (or rather, knowledgeable regarding the crime) person could do. Therefore such a subject is determined to be guilty.

Before the responses are compared, several techniques of signal-to-noise enhancement may be applied.

Eye movements create electrical potentials that interfere with brain-generated electrical patterns measured at the scalp. These are eliminated in one of two ways. 1) A threshold is set either for the absolute value of the eye channel data or for range of the eye channel during a trial. If the eye channel data exceed the threshold for a given trial, then the trial is rejected. 2) A regression algorithm is applied (this is a standard method in electrophysiology and I did not invent it) that estimates the contribution of the eye movements to activity at each of the other channels and subtracts it out.

Muscle artifacts produce either high frequency activity, or large, slow shifts in electrical potential, or both. To eliminate muscle activity, trials are rejected that have any of the following in any EEG channel: a large voltage shift in any channel (range or absolute value threshold); excess high frequency activity (as determined by an FFT); a change with too great a slope (e.g., change between 2 consecutive digitized points exceeds a criterion); excessive standard deviation or variance in the data; excessive mean absolute deviation.

A baseline of about 100 to 300 msec prior to stimulus onset is subtracted from each waveform before analysis, to correct for baseline differencecaused by DC drift or other factors.

Individual trials may also be displayed off-line, inspected, and rejected if visual inspection reveals artifacts not detected by the artifact-rejection algorithms.

Data may also be digitally filtered to eliminate high frequency noise. Typically I use an optimal, equal-ripple, linear phase, finite impulse response (FIR) filter with a passband cutoff frequency of 6 Hz and a stopband cutoff frequency of 8 Hz. (Note: these filters are well known in electrical engineering, but I am the first one I know of to apply them to event-related brain potential data. I am the first author of a definitive paper on this subject that will be submitted for publication shortly.)

During data collection, the stimuli are displayed to the subject on one video monitor, and the experimenter views another monitor (or, in some cases, two or three monitors). Operator displays include 1) the same thing the subject sees, 2) summary textual information, and 3) waveform displays.

The operator's monitor presents some or all of the following waveform displays: ongoing EEG for up to 3 channels, plus one channel of eye movement data; continually updated target, probe, and irrelevant average waveforms, overplotted, for any channel; averages of each trial type in a separate frame with up to 4 channels overplotted. On-line averages only include the artifact-free trials, although all trials are recorded.

The operator's monitor also includes the following textual information: counts of total trials and total trials of each trial type (i.e., target, probe, and irrelevant); counts of artifact-free trials and artifact-free trials of each trial type; status of the current trial—artifact-free, or artifact detected, and which artifacts are detected on this trial; continually updated reaction times by trial type; percentage of correct button press responses by trial type; trial type of the current trial; stimulus presented on the current trial.

When one or more blocks of trials, typically about 150 trials per block, have been presented, then the data are analyzed. The first level of analysis is a visual comparison of the waveforms to determine if the probe response is more similar to the irrelevant response (innocent) or the target response (guilty). Then an iterative sampling bootstrapping algorithm is applied to arrive at a determination and a statistical confidence for the determination. (Recall that eye movement rejection or correction, artifact rejection, and/or digital filtering may precede the data analysis.)

The algorithm is as follows.

A) Iterative sampling

1) T target trials, P probe trials, and I irrelevant trials, with T, P, and I are equal to the total number of trials of the respective types, are sampled with replacement.

2) These trials are averaged by trial type, yielding three average waveforms. The average waveforms are compared according to an algorithm to determine if the probe average is more similar to the targets or to the irrelevants (or if the probes are different from the irrelevant trials in the direction of the targets).

3) The above procedure is repeated multiple times (usually 100 iterations). Each iteration yields a new set of 3 averages containing probe, target, and irrelevant trials respectively. A tally is kept of the number of times the probe average is more like the irrelevant average than like the target average.

4) The tally is a single index which is compared to a decision criterion. A typical criterion is, if the probes are more similar to the irrelevants than to the targets in less than 10% of the iterations, the subject is determined to be guilty. If the probes are more similar to the irrelevants in more than 70% of the cases, the subject is determined to be innocent.

B) Comparison algorithms

A number of different algorithms have been used as measures of similarity of waveforms for determining how the tallies will be incremented.

1) The preferred algorithm is as follows: a) subtract the grand mean of all trials, or grand average waveform, from each of the 3 averages, yielding 3 adjusted averages; b) compute the correlation between the adjusted probe average and the adjusted irrelevant average; c) compute the correlation between the adjusted probe average and the adjusted target average; d) compare the probe-irrelevant correlation with the probe-target correlation: if the probe-irrelevant Correlation is greater, then increment the "innocent" tally by one; otherwise, increment the "guilty" tally by one.

2) Alternative comparison algorithms, for determining whether the probe waveforms are more similar to the irrelevants than to the Targets for each iteration, include the following: a) compare the area under the curves in a given range (area defined as the sum of the points in the time range of the P300), i.e., 300–900 msec; b) compare the peak amplitudes (maximum value—recall that the P300 is a positive peak) of the waveforms in a range as in (a), (base to peak defined as the most positive point in the time range of the P300 minus the average of the points in the baseline prior to the stimulus onset), c) compare the peak-to-peak amplitudes, that is, the peak amplitude it, a range as in (a) and (b) minus the minimum in an earlier range (i.e., 0 to 300 msec), (peak to peak defined as the most positive point in the time range of the P300 minus the most negative point post-stimulus and prior to the time range of the P300); d) use step-wise discriminant analysis to develop a discriminant function to discriminate between target and irrelevant waveforms, and apply this function to the probe waveforms to determine whether the probes are more similar to the targets or the irrelevants; e) do not subtract the grand mean before computing the correlations; f) use covariances instead of correlations; g) use the Cz channel instead of Pz if the P300 is larger at Cz; h) use both Pz and Cz channels; i) use all three channels, Fz, Cz, and Pz; j) average sets of irrelevant trials (e.g., each 4 trials) together to reduce the total number of irrelevants to equal the number of targets and probes.

In addition to displaying the results of the analysis on the screen, the system may also print out on a printer the statistical results, the summary textual information, and the waveform displays, all of which are described above.

In a preferred embodiment, the method of detecting concealed information regarding an event, stored in a human brain, includes: a) Presenting stimuli consisting of information relevant and irrelevent to the event; b) Recording electrical brain activity subsequent to the presentation of each stimulus; c) Comparing the responses to the stimuli, preferably on the basis of event-related brain potentials such as P300 components.

In the method the subject is preferably informed by the researcher regarding some, but not all, of the relevant stimuli, i.e., the Targets are a subset of the relevant stimuli as described above.

The comparison step then compares the brain responses to the informed relevant stimuli (or Probes), the uninformed relevant stimuli (or Targets), and the irrelevant stimuli (or Irrelevants).

ADDITIONS AND MODIFICATIONS

Numerous modifications may be made in the basic design specified above.

The comparisons in the method of the electrical brain responses for the Probe, Target, and Irrelevant Stimuli may be computed on the basis of a single average of each type, without iterative sampling; and the results of the comparisons of single averages may be compared with criteria for determining whether the subject does or does not recognize the Probe stimuli.

The differences and ratios of each of the measures or methods comparing each of the trial types may also be computed. And, the results of the different measures may be combined using multiple regression.

Digitizing rate, stimulus duration, inter-stimulus interval, and other timing parameters may be varied.

Electro-oculographic (EOG) activity may be collected not only by electrodes above and below one eye, but also by lateral EOG electrodes. Alternatively, one electrode above the eye, (referred to the mastoids, to a non-cephalic reference, or to another reference on the head) may be used to replace the electrodes above and below the eye.

Instead of visually presented words, pictures that are digitized and displayed on a video monitor may be used. Also, moving video pictures may be used, with particular critical events time stamped and the EEG activity time-locked to those events analyzed. Stimuli may also be presented through the auditory modality, through use of digitized speech or other sounds presented through a D to A converter, amplifier/attenuator, and speaker system. Auditory stimuli may be entire sentences instead of short phrases. Here again, certain critical words or auditory events are time stamped so that the corresponding EEG activity can be analyzed. In the case of moving video pictures or digitized auditory activity, a stimulus may last for a number of seconds or longer, rather than for only a fraction of a second.

A NEW, RELATED EMBODIMENT

The embodiment described above referred to the use of this system to investigate whether or not an individual had information stored in the brain regarding a particular event, e.g., a crime, when the investigator knows what the information is and can therefore construct appropriate stimulus sets. The same system can be used for a different kind of information detection, when the investigator does not know certain information, but knows or suspects that the subject possesses the information. If the information in question can be reduced to a multiple choice presentation, then the correct information can be detected on the basis of the P300.

Say, for example, that an investigator suspected that a captured spy knew of a plot to assassinate a particular American political leader, but the investigator did not know where, when, or the identity of the intended victim; or, it was suspected that an individual knew of a plot to blow up a particular airliner at a particular time, but investigators had been unable to determine which specific plane would be hit.

A stimulus set could be constructed consisting of 1) rare, target stimuli to which the subject was instructed to respond in some way (e.g., push a particular button), and 2) frequent, non-target stimuli. The non-target stimuli could contain a number of different possible relevant stimuli (in effect, "probes"), but the examiner would not know which stimuli were relevant. If the subject did have particular knowledge regarding certain stimuli—e.g., if the name of the intended assassination victim, known to the subject but not to the examiner, were presented—this would constitute a rare, relevant event, and could be expected to elicit a P300. The other non-target stimuli, having no major significance in this context, would be expected not to elicit a P300 (like the irrelevants in the original embodiment).

Instead of comparing a known probe with targets and irrelevants, data analysis in this case would compare each of the non-targets—all possible "probes"—with the other non-targets (presumably mostly irrelevant) and with the targets (known to be rare and relevant as a result of experimental instructions). The relevant item, if any, would be detected as the non-target item that elicited a large P300, similar to the target response and in contrast to the response to the other non-targets.

In such a case, one could detect information that was not known to the examiner in advance, provided that the examiner knew enough about the kind of information that might be relevant to construct an appropriate multiple-choice test. Given that many modern college students graduate from college on the basis of an accumulated data base virtually all of which has been reduced to a multiple-choice format for presentation on computer-scored tests, such a technology shows some promise of being capable of detecting large amounts of concealed information.

Another method of detecting whether or not someone is telling the truth includes:
a) asking questions of the individual;
b) noting the individual's answers;
c) asking the individual, in addition to the answers to the questions, to report continuously in a stream-of-consciousness fashion, on their ongoing thought processes;
d) measuring electrical brain activity during this process; and
e) comparing the electrical brain activity to standards for activity when a subject is known to be accurately reporting on his/her spontaneous mental activity and for activity when an individual is known to be speaking something that is at variance with his ongoing mental activity.

Alternatively phrased, the method of detecting whether a subject is telling the truth includes:
(a) asking questions of the subject and asking the subject to report continuously in a stream-of-consciousness fashion on his/her spontaneous mental thoughts,
(b) recording electrical brain activity during step (a), and
(c) comparing the electrical brain activity to standards for activity when a subject is known to be accurately reporting his/her spontaneous mental thoughts and for activity when a subject is known not to be reporting his/her spontaneous mental thoughts.

Advantages of the Farwell Truth Detector over Conventional Techniques

The Farwell Truth Detector that is the subject of the present research works on a fundamentally different principle than that employed by conventional lie detection devices. This new principle allows the Farwell Truth Detector to combine the strengths of each of the conventional techniques and overcome both their respective comparative weaknesses and the major problems common to all three.

The Farwell Truth Detector deals with the difficulties common to all conventional polygraphy techniques as follows.

The Farwell Truth Detector does not depend on creating any particular set of emotions in the subject. It works solely on the basis of physiological manifestations of information processing carried out by the brain. This reduces two sources of variability: 1) individual differences in emotional responsivity (which could be the result of inherent individual differences in psychological makeup, intentional manipulation, drugs, or other factors), and 2) differences in the skill and ability of the examiner to structure questions to elicit these specific emotions. According to the theory on which it is based, the Farwell Truth Detector measures the physiological manifestation of a specific information-processing process implemented by the brain. According to the theory, this process, context updating, is undertaken by individuals in every psychological and emotional state, and by individuals with every combination of psychological traits.

Unlike breathing, electrodermal response, and cardiovascular activity, there is no evidence that the P300 can be voluntarily suppressed, or substantially modified by drugs, as long as the information-processing brain processes of which it is a manifestation are taking place. Nor is there any evidence that it can be voluntarily elicited in the absence of these information-processing brain activities. Moreover, individual differences in the time course and morphology of the P300 are controlled for in the signal detection algorithm employed in the Farwell Truth Detector: the response to target stimuli provides a control, to which the probe responses can be mathematically compared.

Rather than providing a complex series of measurements demanding interpretation based on the skill and subjective tendencies of the examiner, the Farwell Truth Detector computes a result through a set mathematical algorithm. It presents not only a binary result, or single index, but also a statistical confidence level for that result.

The Farwell Truth Detector also addresses the shortcomings that are peculiar to each of the different conventional detection of deception techniques. The unique independence of the Farwell Truth Detector from the emotional states or traits of the subject, its method of operation based on measuring the physiological manifestations of information-processing processes carried out by the brain, and the mathematical signal-recognition algorithm it employs allow the Farwell Truth Detector to combine the unidimensionality characteristic of the guilty knowledge test with the control characteristic of the control question test.

As described above, the primary weaknesses of the control question test, when compared to the other conventional techniques, are that the relevant questions are relevant and emotionally arousing for innocent as well as guilty subjects, and that the control, relevant, and irrelevant questions differ on other dimensions in addition to the dimension of interest. They are three different types of questions, covering three different types of subject matter. This introduces an additional source of variability, and limits the effectiveness of the control questions in providing effective control.

Differences between responses to control and relevant questions may result from differences between the types of questions, rather than from the truthfulness or deceptiveness of the subject. Either an innocent or a guilty individual may respond differently to "Have you ever stolen anything from any business establishment?" (control) than to "Did you rob First National Bank on July 1?" (relevant). Similarly, the differences between these two responses and the subject's response to "Is your name Bill Smith?" (irrelevant) may also be due to a number of different factors, some of which may be have nothing to do with the subjects veracity in the present situation.

This problem is eliminated in the Farwell Truth Detector in a similar way to the way it is eliminated in the guilty knowledge test. The stimuli presented in the Farwell, like the questions of the guilty knowledge test, are unidimensional: they are the same on the dimension of "relevance to criminal activity of any kind." All of them are equally relevant to criminal activity, yet some of them (the probe stimuli) contain factual information regarding this particular crime, and the rest do not.

To an innocent individual, the probe and irrelevant stimuli, like relevant and irrelevant questions in the guilty knowledge test, are indistinguishable. For a guilty individual, the probe stimuli also form a rare subset that the guilty individual cannot help but notice, provided, of course, that he remembers the crime. This, in turn, provides the antecedent condition for the elicitation of a P300, again regardless of the emotional state of the subject. The P300 is further enhanced by the fact that the probe stimuli are also noteworthy to the subject. In this way, the Farwell Truth Detector elicits differential responses without introducing fundamentally different types of stimuli, and without dependence on the emotional state of the subject.

The primary shortcoming of the guilty knowledge test, as described above, is lack of control for individual differences, of whatever origin, in responses to relevant questions. If a subject does not respond differentially to the relevant questions, there is no indication of what it would have taken to make that subject respond differentially to a question, or indeed if such a response could ever be elicited from this particular subject. This may make the guilty knowledge test particularly prone to false negatives. In the Farwell Truth Detector, for either a guilty or an innocent individual, the target stimuli provide a control. They are no different from the irrelevant stimuli in content, but the subject is instructed to engage in a different information-processing task when they appear. Specifically, he is instructed to press a special button when they appear. Thus the target stimuli, though not inherently different, constitute an arbitrarily designated subset of relatively rare stimuli, which provide the antecedent condition for the elicitation of a P300. Again, the P300 amplitude is enhanced by the fact that the individual takes note of the stimuli in order to perform the button press task. The P300 elicited by the target stimuli can be compared with his response to the probe stimuli in order to determine if the probes, too, constitute a subset of rare stimuli (which would indicate knowledge of the crime).

The target stimuli, then, provide for a control condition without introducing a major additional source of variability. Because what is being measured is the physiological manifestation of an information-processing function, it is not necessary to introduce a different type of stimuli (like the control questions of the control question test) designed to evoke a particular set of emotions. Thus, the inevitable additional source of variability that weakens the control question test is avoided, while the control that is lacking in the guilty knowledge test is nevertheless accomplished.

The Farwell Truth Detector does have one weakness when compared with the control question test, a weakness that is shared by the conventional guilty knowledge test. This is that the test involves more work for the investigator in gleaning sufficient details about the crime that a knowledge-based test can be structured. There are some cases, also, where a Farwell Truth Detector test can not be used: where such knowledge is entirely unavailable, where the suspect has been contaminated by too much crime-specific information mistakenly provided during previous interrogations, and in some cases where the suspect admits being present but denies having committed the crime. As mentioned previously, the extensive use of the conventional guilty knowledge test in the field in Japan and Israel attests to the fact that these problems are not insurmountable. Again, the fundamental shortcoming of the conventional guilty knowledge test—lack of a control stimulus—is not shared by the Farwell Truth Detector.

The fundamental differences enumerated above that distinguish the Farwell Truth Detector from conventional methods of interrogative polygraphy may be responsible, at least in part, for the high levels of accuracy achieved in the present study. These differences are fundamental to our hypothesis that the P300 can be accurately and effectively used as an indicator of guilty knowledge that has major advantages over conventional techniques. In the next section I will consider the nature of this event-related brain potential component and the theoretical and practical considerations that make possible its application in the psychophysiological detection of concealed information.

THE P300 COMPONENT

Introduction

This section will describe the P300 component of the event-related brain potential, which forms the basis of the brain-wave-based system for the psychophysiological detection of concealed information that has been developed, implemented, and tested in the program of research described in subsequent sections. The physical characteristics of the component and what is known of its neural origin will be described, the antecedent conditions and consequences of its elicitation will be enumerated, and several alternative theoretical accounts of its functional significance will be discussed.

The theoretical discussion will focus particularly on the context updating model of the functional significance of the P300 (Donchin, 1981), since it is this model that gives rise to the hypotheses regarding the response of the P300 to experimental manipulations that form the basis for its predicted applicability to the psychophysiological detection of concealed information. The context updating model will be compared and contrasted with other models of the functional significance of the P300. The differing predictions that arise from these different models as to the results of the research program outlined herein will be discussed.

The Context Updating Model and the Farwell Truth Detector

The context updating model of the functional significance of the P300 (Donchin, 1981; Donchin, McCarthy, Kutas, & Ritter, 1983; Donchin, Karis, Bashore, Coles, & Gratton, 1986; Donchin and Coles, 1988a; 1988b) is based on the following knowledge and understanding.

A number of different theories or models have been advanced to explain the process through which an individual maintains a working knowledge of his operating environment that allows him to function in that environment. These different theories or models, however, all have one common feature: it is universally recognized that the individual must maintain some kind of internal representation of his environment. This representation or schema has variously been described as working memory, a "neuronal map", or a "scratch pad" containing information relevant to the current activity in the current environment (Sokolov, 1969; Baddeley & Hitch, 1974; Baddeley, 1981). Obviously, if this internal representation, however conceived, is to continue to be useful to the individual in functioning in his environment, there must be a way of updating this model as the environment and the individual's activities within it change. Mismatches between the expectations generated by the schema and the realities encountered in the environment must be registered, and repeated or substantial mismatches must be capable of forcing a revision of the schema. Otherwise, it would cease to be a viable representation in a changing environment. Context updating, then, is a necessary information-processing function that must be continually undertaken by any individual who is capable of functioning coherently in a complex, changing environment (Donchin, 1981).

According to the context updating model, the P300 is a manifestation at the scalp of the information processing brain activity that is involved in context updating. (See, for example, Donchin, Karis, Bashore, Coles, & Gratton, 1986.) This information processing "subroutine" is implemented when a subject is presented with information that is rare, surprising, or unusual, and/or is noteworthy, useful, task-relevant, or meaningful to the individual. The rationale and experimental evidence for this theory is presented in the section below entitled "Hypotheses of the Functional Significance of the P300."

The brain-wave-based system for the psychophysiological detection of concealed information described herein presents three kinds of information: information that does not meet these prerequisites for the elicitation of the subroutine of which the P300 is a manifestation (the irrelevant stimuli), information that meets these prerequisites for either a truthful/innocent or a deceptive/guilty individual (the target stimuli), and information that meets these prerequisites only for a deceptive/guilty individual (the probe stimuli). By comparing the brain responses to these three classes of information, a determination can be made as to the status of the individual—truthful or deceptive, guilty or innocent, or, more correctly, knowledgeable of the details of the crime or lacking in such knowledge.

The interrogative polygraphy system described herein is founded on the context updating model of the P300, and, as will be described in detail below, its predicted success depends on an elaboration and extension of that model. Thus, the research program presented here will serve not only as a test of a new theory in the field of psychophysiological detection of concealed information, but also a test of predictions derived from the context updating model and the elaboration of that model described below.

The following discussion of the nature of the P300 will focus on the context updating model and the predictions it makes regarding experimental results. The alternative models that have been proposed will also be discussed.

Characteristics and Antecedent Conditions of the P300

Physical Characteristics

The P300 is a positive-going electrical potential that takes the form of a rise in voltage to a peak followed by a return to baseline (Sutton, Braren, Zubin, & John, 1965; Sutton, Tueting, Zubin, & John, 1967). The peak occurs 300 msec or more after the eliciting event. The P300 is maximal at the midline parietal scalp, or, less frequently, at the midline central area (Pz and Cz scalp locations respectively in the International 10–20 system, Jasper 1958). The scalp distribution is independent of the modality of the eliciting stimulus (Simson, Vaughan, & Ritter, 1976. For reviews see Donchin, Karis, Bashore, Coles, & Gratton, 1986; Pritchard, 1981; Donchin & Coles, 1988a; 1988b).

Putative Neural Generators of the P300

There has been considerable controversy over the neural generator or generators of the P300 component. Here "neural generator" means that structure or area of the brain where the voltage potential that is recorded at the scalp as a P300 originates. This problem has been approached from a number of different angles, each with a unique set of strengths and weaknesses. The scalp distribution is readily measurable and provides some clues, but, since currents in a volume conductor sum linearly by Helmholz's principle of superposition, surface recordings can not provide sufficient information to identify a unique intra-cranial source (Allison, Wood, & McCarthy, 1986; Vaughan & Arezzo, 1988). Magnetic recordings can also be of use, but they suffer from a low signal-to-noise ratio, and the inferences made regarding intra-cranial sources generally involve simplified assumptions regarding the nature of these sources and other structures in the head. Intra-cranial recordings provide precise information about the electrical activity in certain brain areas, but in humans must of course be restricted to those recording locations fortuitously available when electrodes are inserted for medical purposes. Similarly, neuropsychological studies in humans are limited to the situations available fortuitously. Lesion and intra-cranial studies in animals lend themselves to precise experimental manipulation, but present uncertainties due to the neurological and psychological differences between animals and humans.

A number of studies have provided evidence that the P300 may be generated, at least in part, in the hippocampus and related limbic structures. Halgren, Squires, Wilson, Rohrbaugh, Babb, & Randall (1980) used simultaneous scalp and depth electrode recordings in a standard P300-producing task, the "oddball" design (see "The Oddball Experimental Design" below), wherein the subject is required to respond to a subset of relatively rare ("oddball") stimuli. They found large voltage potentials, steep voltage gradients, and polarity reversals—indicators of an electrical source—in the hippocampus, amygdala, and parahippocampal gyrus. Like the P300s that were simultaneously recorded from scalp electrodes, the limbic potentials were larger to the rare stimuli, were substantially attenuated if the subject was instructed to ignore the stimuli, and were independent of stimulus modality. In some cases, changes in the firing rates of local neurons corresponded to the field potentials. Similar results were found by Wood et al., 1980. Halgren et al. point out, however, that the observed correlation between scalp and limbic potentials does not necessarily indicate that the scalp potentials are in fact the result of volume conduction to the surface of the limbic potentials.

Okada, Kaufman, & Williamson (1983) used magnetic recordings in a visual oddball task. Their computations led to the conclusion that "the sources of N2 and P3 lay deep within the brain in the hippocampal formation."

Buchwald & Squires (1982) used depth electrodes in the cat to observe intra-cranial potentials that responded in somewhat similar ways to experimental manipulations as the P300 in humans, although they did not provide definitive evidence of the intra-cranial location of the generator.

Smith, Stapleton, & Halgren (1986) used depth electrodes in the hippocampus, amygdala, and parahippocampal gyrus in a series of verbal tasks involving recent memory. As in previous studies, they found a large potential in the medial temporal lobe that responded to experimental manipulations in a manner similar to the P300. Like the scalp-recorded potential to verbal stimuli, this potential had a longer latency than the P300 elicited by simple tones.

More recent research has demonstrated that medial temporal lobe potentials respond similarly to the P300 in a number of more sophisticated experimental designs. McCarthy, Wood, Williamson, & Spencer (1989) observed a potential characterized by sharp spatial voltage gradients that was positive anterior and posterior to the hippocampus and negative within the hippocampus. The potential was elicited by low-probability auditory, visual, and somatosensory stimuli in categorization tasks. Like the P300 (see below discussion) this potential could be elicited by exemplars of verbal categories and by omitted stimuli, and responded to variations in the sequence of preceding stimuli. Also like the P300, this medial temporal lobe potential was observed only when the subjects were instructed to perform the categorization task, and not when the same stimuli were presented with instructions to attend elsewhere.

Knight, Scabini, Woods, & Clayworth (1989) reported lesion results compatible with a temporal lobe generator for the P300. They found that the scalp-recorded P300 was eliminated in patients with unilateral lesions of the temporal-parietal junction. They observed no decrement in P300 in patients with unilateral lesions of the lateral parietal cortex, even when the lesion was directly under the recording site.

Some converging evidence, then, points to the hippocampus and associated limbic structures as the neural generator, or at least one of several generators, of the P300 that is recorded at the scalp. Other researchers, however, have found contradictory evidence. Johnson & Fedio (1984) found normal P300s recorded at the scalp in unilateral temporal lobectomy patients. Johnson & Fedio (1986) found some differences in P300 between temporal lobectomy patients and normal controls, but nevertheless found substantial P300s in the patients and did not find consistent asymmetries that distinguished right- from left-temporal lobectomy patients or either group from normals. They concluded that there probably is more than one generator of the P300, and that the limbic potential recorded by depth electrodes probably contributes little or nothing to the scalp-recorded P300.

Some animal studies have pointed to the same conclusion. Paller, Zola-Morgan, Squire, & Hillyard (1988) recorded a "P3-like" potential from the scalp in monkeys that was similar to the human P300 in morphology, polarity, latency, scalp distribution, and response to experimental manipulations. This potential was observed in monkeys both before and after bilateral temporal lobectomy.

It is possible that the P300 is generated in part in posterior portions of the hippocampus that were spared in lesion studies (McCarthy, 1987). Also, the animal models may or may not accurately represent the human phenomenon.

In summary, the role of the hippocampus and related limbic structures in the generation of the P300 remains an open question. The complicated pattern of results has led a number of researchers to surmise that the P300 has multiple and diversely located generators, perhaps including frontal cortex as well as medial temporal lobe and other areas (McCarthy, 1987).

The Original Sutton et al. Studies

The P300 was first reported by Sutton and his colleagues in 1965 (Sutton, Braren, Zubin, & John, 1965). Sutton et al. used a dual-stimulus experimental design in which a warning stimulus consisting of either an auditory click or a visual flash was followed after an interval of several seconds by another flash or click. The predictive value of the warning stimulus was manipulated in order to manipulate the degree of certainty/uncertainty of the subjects' knowledge of the nature of the second stimulus. In different blocks of trials, the warning stimulus predicted the subsequent stimulus with either 100% accuracy or with a lower probability. They found that the P300 to the second stimulus was larger when there was uncertainty preceding the arrival of that stimulus.

They then introduced a guessing manipulation, and further varied the predictive value of the warning stimulus. In the interval between the two stimuli the subject reported a guess as to whether the second stimulus would be a sound or a flash. In some cases the warning stimulus predicted a light 33% of the time and a sound 67% of the time, and in some cases the probabilities were reversed. Regardless of the sensory modality of the stimuli, subjects exhibited larger P300s in response to improbable than probable stimuli.

The guessing design was employed to investigate the effect of subjects' expectations on the P300 independent of actual stimulus probability. Subjects were required to guess the modality of the second stimulus when the warning stimulus had no predictive value. P300s in response to the second stimulus were larger when the guess was disconfirmed than when the guess was confirmed.

These results led Sutton et al. to conclude that the P300 was an "endogenous" component, that is, that it related to the "reaction, or attitude, of the subject toward the stimulus" and not to the sensory character or modality of the stimulus. They summarized their findings in the statement that the component was affected by the subjects' "degree of uncertainty" regarding the stimulus and by whether the sensory modality of the stimulus was "anticipated correctly."

Sutton and his colleagues extended their findings and their theoretical account in a second seminal paper entitled "Information delivery and the sensory evoked potential," which was published in 1967 (Sutton, Tueting, Zubin, & John, 1967). In summarizing their 1965 work they noted that the late positive component was related to the "effective information content of the stimuli," with a larger positive deflection occurring when "the amount of information is greater," that is, when the stimulus is "unanticipated" or of "low probability."

This second series of studies further investigated the relationship between the P300 and the delivery of information. The first experiment in this series used single and double clicks to deliver the relevant information. In different blocks, two click stimuli were separated by 180 or 580 msec. Subjects were instructed to guess verbally whether each click would be single or double. In blocks where the clicks were separated by 180 msec, the information as to whether or not the guess had been correct was delivered 180 msec after the first click, either by the occurrence or the non-occurrence of a second click. When the interval was 580 msec, this information was not delivered until after 580 msec. P300s occurred at the point in time when the information was delivered in every case, whether the information was delivered by the presence or absence of a second click. The P300 was delayed in the 580-msec interval blocks until after the time when the second click either occurred or was known not to have occurred. When the subject was informed in advance whether the stimulus would be single or double, no task-relevant information was delivered by the clicks and no P300 occurred.

Another experiment manipulated which aspect of the information delivered by the stimulus was task-relevant, and when that information was delivered. Four types of click pairs were presented: soft single clicks, soft double clicks, loud single clicks, and loud double clicks. In some blocks subjects were required to guess whether each stimulus would be loud or soft; in alternate blocks, they guessed whether each stimulus would be single or double. Thus, in the loud/soft guessing task, the information was delivered by the first click, whereas in the single/double guessing task, the information was delivered by the presence or absence of the second click. Again, the P300 occurred at the point in time when the information was delivered and uncertainty was resolved.

Sutton et al. then went on to demonstrate the relationship between information delivery and P300 in a more complex experimental design. Three types of double clicks were presented in random sequence, separated by 180, 580, and 980 msec. Subjects guessed "short," "medium," or "long" before each pair. Once again, the late positive complex occurred at the point in time when the information relevant to the experimentally assigned task was delivered. For example, if they guessed "long" and the interval was short, they would find out that they had guessed incorrectly after 180 msec, and the P300 occurred at that time. If they guessed "long" and the interval was long, all of the information was delivered by the time of the non-occurrence of the medium stimulus: since the short and medium stimuli had not occurred, the subject knew at that point that he or she had guessed correctly, and the P300 occurred at that point.

Sutton et al. concluded that the P300 is elicited when "ambiguity" or "uncertainty" is "reduced," "whether it is the presence or absence of an external event that delivers the information." With the "loud" and "soft" manipulation, they also showed that the delivery of such information elicits the P300 only when it is relevant to the task assigned by the experimenter.

This relationship between the delivery of explicitly task-relevant information and the P300 was a major factor in the formulation of the context updating model.

The Oddball Experimental Design

Since the original Sutton et al. papers, most of the research on the P300 has been conducted using the "oddball" experimental design. In this design, a series of stimulus events is presented to a subject. Stimuli may be auditory, visual, or somatosensory. Stimuli are defined in experimental instructions to be comprised of two categories, with one category (the "oddballs") occurring relatively rarely. Stimuli are presented in random order, and an experimental task is assigned that requires the subject to categorize the stimuli according to categories specified in the instructions to the subject, and to respond in some way to the rare stimuli (e.g., press a button or count occurrences). The rare, task-relevant stimuli (the oddballs) elicit a P300.

In the oddball experimental design, then, probability and explicit task relevance are critical controlling variables for the P300.

The categorization rule may be either concrete or abstract. Categories have included high and low tones, sets of letters or groups of letters, male and female names (Kutas, McCarthy & Donchin, 1977), and pictures of politicians interspersed with pictures of other people (Towle, Huer, & Donchin, 1980). The eliciting event need not be the presence of a particular stimulus or category of stimuli: the absence of a stimulus at a particular point in time, when this absence delivers information to the subject, can elicit a P300 (Sutton, Tueting, Zubin, & John, 1967).

Probability

The many basic studies conducted on P300 amplitude and probability have found an inverse relationship between the probability of task-relevant events and the amplitude of the P300 they elicit. This relationship was explicitly tested by Duncan-Johnson & Donchin (1977). They presented different series of counted and uncounted (high and low) tones, with the probability of counted tones varied from 0.10 to 0.90 in different blocks. They reported a monotonic inverse relationship between P300 amplitude and the probability of the eliciting event.

Additional research has modified the concept of probability. "Subjective probability," the expectation of the subject, rather than a priori, or objective, probability, appears to be the controlling factor for P300 amplitude. The first investigations of subjective probability actually were reported by Sutton et al. in 1965, although they did not use that term. As discussed previously, Sutton et al. found larger P300s when the arrival of a stimulus did not match the subjects' expectations as indicated by a prior guess as to the modality of the stimulus. Squires, Wickens, Squires, & Donchin (1976) investigated subjective probability by examining the P300s elicited in response to stimuli preceded by different sequences. The task was to count occurrences of one of two tones of different frequencies, each of which occurred on 50% of the trials overall. The P300 to a tone was larger when the preceding stimulus was of the other type. The longer a string of stimuli of the other type that preceded a given tone, the larger the P300 to the tone. The longer a string of stimuli of the same type preceded a tone, the smaller the P300 to the tone. In other words, even though the global probability was 50% for each type of tone, the subject's expectation or subjective probability of the tone was apparently influenced by the stimulus sequence preceding the tone. The authors interpreted this in terms of decaying memory traces.

Another situation in which the subjective probability of an event affected P300 amplitude was reported by Horst, Johnson, & Donchin (1980). Subjects memorized pairs of nonsense syllables. On each trial, the computer provided one member of a pair, and the subject attempted to type in the correct associated syllable, along with an indication of the level of confidence they had in their response. Then the computer presented the correct syllable. The largest P300 to these feedback stimuli occurred when they resulted in the greatest violation of the subjects' reported expectancy: when they were informed that they were incorrect when they were sure they had been correct and vice versa. According to the context updating hypothesis this result comes about because these surprising feedback stimuli resulted in the largest modifications in the schema.

If it is going to be possible to use the P300 in the psychophysiological detection of deception, it must be possible to dissociate the P300 from overt behavior. This was achieved to some degree by Karis, Chesney, & Donchin (1983), in an experiment that examined the relationship between subjective probability, P300 amplitude, and overt behavior. Subjects were paid on the basis of their accuracy in predicting which of three digits (1, 2, or 3) would appear next in a series. The actual probability of the digits was held constant at 0.45 for 1 and 3 and 0.10 for 2. By varying the schedule of rewards for correct and incorrect guesses, subjects' overt behavior could be changed such that the number of 2's chosen would increase or decrease; but the 2's continued to elicit the largest P300s regardless of the changes in reward structure and overt behavior.

Heffley (1985; Heffley, Wickens, & Donchin, 1978) found that the effects of probability on P300 amplitude interact with the inter-stimulus interval. At long inter-stimulus intervals (greater than 3 seconds), P300s were elicited by both rare and frequent stimuli. According to the context updating model, this may be because the probability effect depends on stimulus representations in memory (Donchin, Karis, Bashore, Coles, & Gratton, 1986). The longer intervals make it necessary to refresh stimulus representations even of the frequent stimuli, thus bringing about an updating of the schema in response to frequent as well as rare stimuli.

Task Relevance

Probability alone is not a sufficient condition for the elicitation of a P300. The stimulus must also be task-relevant (Donchin & Cohen, 1967). As a rule, P300s only appear when the subject is required to extract information from the stimulus in order to perform an experimentally assigned task. (The research program presented here, however, predicts an important exception to this rule. See "Hypotheses and Theoretical Significance of This Research" below.)

Manipulations of task relevance were reported in the original Sutton et al. (1967) studies. As discussed previously, they showed that the appearance of the P300 could be manipulated by differential instructions as to which aspects of the stimuli (loud/soft or single/double clicks) were relevant to the experimentally assigned task.

Duncan-Johnson & Donchin (1977) showed that when a series of tones is presented and a subject is instructed to count the high tones, the high tones elicit a P300. When the same series was presented and subjects were instructed to ignore the tones and solve a word puzzle instead, no P300s were elicited despite the fact that the tones were heard.

Moreover, the amplitude of the P300 varies directly with the information value of the eliciting stimulus for the assigned task. Johnson & Donchin (1982) presented subjects with a series of tones of two different frequencies at probabilities of 0.77 and 0.33. Periodically, the probabilities of the two types of tones were reversed. The subjects' experimentally assigned task was to detect this shift. After each shift, the P300 amplitude became progressively larger as the subject attempted to extract the necessary information from the stimulus sequence to detect the change. The largest P300s occurred immediately prior to the subjects' announcement that they had detected the shift.

Another demonstration of the relationship between information provided by the stimulus and P300 amplitude is provided by Gratton et al., 1990. They presented warning stimuli that predicted a stimulus to which the subject was instructed to respond. The warning stimuli predicted that an identical stimulus would follow with a probability of 0.8, 0.5, or 0.2. P300s to the 0.8 and 0.2 prediction level warning stimuli, which provided information useful for performing the assigned task, were larger than to warning stimuli with a non-informative 0.5 (i.e., chance) prediction level.

Processing Resources

The amplitude of the P300 is modulated not only by the task relevance of a single task, but also by the processing resources devoted to a given task when multiple tasks are performed simultaneously (Donchin, Karis, & Witkens, 1986). In research on engineering psychology, the oddball task (using, for example, a count-high-tones task) has been inserted as a non-intrusive secondary task in order to assess the resources demanded by a primary task (Wickens, Isreal, & Donchin, 1977; Sirevaag, Kramer, Coles, & Donchin, 1989).

As the resource demands of the primary task are increased, P300 amplitude in response to primary task events increases and P300 amplitude in response to secondary task amplitude decreases. This has been interpreted as indicating that the process manifested by P300 has a limited capacity (Donchin, Kramer, & Wickens, 1986). Results also indicate that the resources that are critical in controlling P300 amplitude are perceptual and cognitive, as opposed to motor, resources (Isreal, Chesney, Wickens, & Donchin, 1980; Isreal, Wickens, Chesney, & Donchin, 1980).

The Latency of the P300 Component

The experimental hypotheses set forth herein involve the amplitude of the P300. Previous findings regarding latency are relevant, however, in that they have contributed to the context updating theory that is fundamental to the experimental predictions made here.

The latency of the P300 component has been used as a means of exploring mental chronometry. Obviously, any process that is required for the elicitation of the P300 must take place by the time the component itself appears. Given that probability of a stimulus category is a major determining factor in P300 elicitation and amplitude, the necessary categorization must take place prior to the appearance of the P300. Donchin (1979) proposed that P300 latency is an index of stimulus evaluation time. (Note that this does not necessarily imply that P300 is a manifestation of the process of stimulus evaluation per se; only that stimulus evaluation and categorization must take place prior the appearance of the P300.)

In support of this contention Kutas, McCarthy, & Donchin (1977) showed that an increase in the difficulty of the categorization task results in longer P300 latency. Correlation between P300 latency and response time is greater when subjects are instructed to respond accurately than when they are instructed to respond quickly. The authors propose that this higher correlation may be a result of the phenomenon that when subjects are instructed to respond accurately, they wait for the categorization process (which must take place by the time of the P300) to be completed before they respond. Also, errors are disproportionately represented in trials in which response time is relatively short and P300 latency is relatively long. That is, when the subjects fail to wait for the categorization process—and the accompanying P300—before responding, they are less accurate. Moreover, accuracy of responses has been shown to be greater for shorter P300 latencies, within a given range of reaction times. When the categorization takes place quickly—resulting in short P300 latency—manual responses of a given latency are more accurate.

Another series of studies (McCarthy & Donchin, 1981; Magliero, Bashore, Coles, and Donchin, 1984) dissociated the effects of stimulus evaluation and response execution on reaction time and P300 latency. Manipulation of the discriminability of a stimulus had approximately equal effects on P300 latency and reaction time, indicating that the relevant processing was completed prior to the P300. Manipulations of the compatibility of the stimulus and the response (respond with the right hand to the word "right" and the left hand to the word "left" or vice versa) affected response latency, but did not affect P300 latency. This indicates that, although the reaction may precede the P300, the process manifested in P300 is independent of the response execution process.

Hypotheses of the Functional Significance of P300

A specification of the antecedent conditions for a P300, even if comprehensive, does not begin to tell us what information-processing process, if any, is manifested in the P300. It describes only what environmental events are necessary and sufficient to elicit a P300, not what actual information-processing activities undertaken by the brain are producing the component (Donchin, 1981).

The same data regarding antecedent conditions has been interpreted by different theorists to support widely divergent theoretical accounts of the functional significance (or, in some accounts, non-significance) of the P300. The following section will describe the major hypotheses that have been advanced, with particular reference to the context updating hypothesis that forms the basis of the predictions made in the proposed research program.

Context Updating

The context updating model was formulated by Donchin and his colleagues (Donchin, 1981; Donchin, Karis, Bashore, Coles, & Gratton, 1986; Donchin & Coles, 1988a; 1988b). According to context updating, the P300 is a manifestation of the process of updating one's internal representation of the current operating environment. The "neuronal map" (Sokolov, 1969) or schema must be continually revised in order to continue to be an accurate representation of the current operating environment. This process has also been described in terms of the updating of representations in working memory (Donchin, Karis, Bashore, Coles, & Gratton, 1986).

The context updating model explains a wide range of experimental results that have been obtained in different experiments in which P300s were observed.

First of all, experimental results make it clear that there are some things a P300 is definitely not. It is not a manifestation of the sensory processing of a stimulus, since the same component can be elicited through different sensory modalities (auditory, visual, or somatosensory), it will or will not be elicited by the same stimulus depending on instructions given to the subject regarding processing of the stimulus, and it can in fact be elicited by the absence of a stimulus. In this sense it is an endogenous, and not an exogenous, component: it must be the manifestation of a process that depends not on the physical nature of the eliciting event but on how that stimulus event is processed (Sutton, Braren, Zubin, & John, 1965; Sutton, Tueting, Zubin, & John, 1967).

The P300 is not a manifestation of any process that must be completed prior to responding to a stimulus, since the latency of the P300 can in some circumstances be longer than reaction time (McCarthy & Donchin, 1981). (Note, however, that this does not imply that the process manifested in P300 does not take place largely before a response is initiated, or that some of the antecedent conditions for a P300 are not also antecedent conditions for a correct response—only that the P300 process can not be one that must be entirely over for the response to be accomplished.)

The context updating hypothesis was formulated to take into account these results, and to explain the appearance of the P300 in response to the two major antecedent conditions for the P300 discussed in the previous section: namely, subjective probability and task relevance. What information processing activity takes place in the brain when and to the degree that information is provided that is relevant to a task the individual is performing and subjectively improbable? According to context updating, the most viable candidate process is that of updating one's internal representation of the current operating environment. If a stimulus arrives that is task-relevant, this new information must be incorporated in the schema for it to continue to be an accurate representation of the current environment. If the same sensory event takes place but is irrelevant and/or unattended, no such updating must take place. The lower the subjective probability of this information—that is, the more unexpected it is—the more one must revise one's internal representation, and the larger the amplitude of the P300 that manifests this process.

The context updating model also explains the previously described experimental results indicating that P300 latency varies with stimulus evaluation processes and not with response selection and execution processes (McCarthy & Donchin, 1981). One can not update the internal representation until one knows what the new event is that is to be incorporated—that is, until the process of stimulus evaluation has taken place. The motor processes involved in carrying out the response, on the other hand, do not form the basis for updating the internal representation. (In some cases, however, as will be discussed below, there is evidence that recognition and evaluation of the response, made, and in particular of errors, may be a part of the event evaluation process that generates the information that is incorporated into the schema by the P300 process.)

In addition to explaining the observed results regarding the antecedent conditions for the P300, the context updating model makes predictions about the consequences of the P300 based on its hypothesized functional significance. These predictions, and experiments designed to test them, will be discussed below in the section entitled "Consequences of the P300."

Resolution of the Contingent Negative Variation

The contingent negative variation (CNV) is a component characterized by a slow increase in negativity, maximal in the midline central scalp location (Cz in the International 10–20 system), that occurs prior to an event ("imperative stimulus") demanding a perceptual judgment, cognitive decision, and/or motor response, when the subject has been warned by a prior stimulus of this impending event (Walter, Cooper, Aldridge, McCallum, & Winter, 1964). Naatanen (1969; 1970) proposed that the apparent positive peak that constitutes a P300 is actually a transient return to baseline following a CNV. According to this hypothesis, the P300 does not reflect any particular information processing activity, but simply results from the cessation of the generalized preparatory processes that give rise to the CNV. Evidence for this hypothesis is provided by the fact that the P300 amplitude following an imperative stimulus often covaries with CNV amplitude preceding the imperative stimulus.

Further experiments, however, have shown a dissociation between P300 amplitude and CNV amplitude, and have demonstrated that the scalp distribution of the P300 is different from that of the CNV. Donchin, Tueting, Ritter, Kutas, & Heffley (1975) orthogonally manipulated stimulus predictability and presence of a warning stimulus. They found that the CNV amplitude was controlled by the warning stimulus, whereas P300 amplitude was controlled by the predictability of the stimulus.

Cortical Deactivation/Context Closure

Desmedt (1980; 1981; Desmedt & Debecker, 1979a,b) proposed a theory of P300 similar to the CNV resolution theory, but without the requirement that a transient CNV precede the P300. The negativity that is being resolved, according to, is a more general one than that induced by the CNV, and is present throughout the experimental session except for momentary returns to baseline that appear as apparently positive P300s. "P300 occurs in the absence of any preceding CNV, but of course against a background of steady cortical negativity." (Desmedt, 1980). Desmedt speculated extensively on the neuronal mechanisms that might bring about such an ongoing negativity and its transient reduction.

According to this theory, the cortex is activated by the attentive state assumed by the subject in the course of an experiment, and an ongoing widespread cortical negativity results. (There has been no experimental confirmation of this.) After the relevant, rare stimulus has been processed, this attentive state is momentarily relaxed, and then resumed in order to continue dealing with the subsequent stimuli. This results in a transient return to baseline which appears, upon the background of ongoing negativity, to be a positive peak—the P300.

In this view, the P300 is not an index of information processing at all. It is merely a result of a transient modulation in the level of generalized activation of the cortex. "P300 does not index actual processing activities, but is interpreted as a post-decision closure mechanism." (Desmedt, 1980).

The evidence cited to support the contention that P300 does not index information processing largely involves the lack of specificity in the antecedent conditions and appearance of the component: it can be elicited through different sensory modalities; it can occur after the motor response or without a motor response; its scalp distribution is relatively widespread.

This theory is diametrically opposed to the context updating theory, which holds that the P300 is a manifestation of a specific, active process, rather than a reduction in the level of subjective and cortical activation.

A theory very similar to Desmedt's, with a somewhat different physiological description, was advanced by Verleger (1988).

> It is assumed that ERPs do not reflect psychological processes, but indicate the interplay of activation and deactivation.
>
> ... the present approach assumes that P3 is generated in the parietal cortex in those areas that function as general control and integration systems of perception ... P3 indicates a phasic physiological deactivation of those tertiary areas. Deactivation means the release of excess activation that has been previously accumulated in these areas ... this deactivation is not a psychological process ... it does not play a direct role in information processing ... However this deactivation ... closely follows an act of information processing ... the cognitive process preceding P3 is described as an act of closure.

A major determinant of P300 amplitude, in Verleger's view, is the amount of processing required by the stimulus," which he holds to be negatively correlated with P300 amplitude. "P300s become smaller the more additional processing the stimulus requires... this interpretation of the evidence ... conflicts with the view that P3 reflects a cognitive operation required for processing the stimulus."

A large P300, according to the brain deactivation/closure theory, is associated with the opposite of activation. "With regard to the subjective psychological consequences of the deactivation indicated by P3, it might well be that this deactivation plays its part to form the basis of feelings of relaxation ," (Verleger, 1988). As will be explained in detail in subsequent sections, this model makes predictions opposite to those of context updating for the experiments described herein.

The cortical deactivation/closure hypothesis, in denying any information-processing function to P300, also does not predict the findings of specific consequences of P300 discussed in the subsequent section. (For a detailed criticism of Verleger's hypothesis, see.Donchin & Coles, 1988a; 1988b).

Controlled Processing

Rosler (1983) proposed a theory of the functional significance of the P300 based on the distinction between automatic and controlled processing (Schneider & Schiffrin, 1977). Controlled processes are intentional, require attention, are capacity-limited, and interfere with other controlled processes. Rosler (1983) hypothesized that "P300 is always evoked with considerable amplitude when the situation calls for controlled information processing, and is absent or only picked up with negligible amplitude when the situation can be handled in a more automatic way."

This hypothesis is at odds with more recent data on P300 and automaticity. For example, Kramer, Schneider, Fisk, & Donchin (1986) showed that P300 amplitude increases when a task becomes automated with practice.

Rosler's more recent writings (Rosler, Borgstedt, & Sojka, 1985; Rosler, 1988) set forth a view similar to context updating.

A Triarchic Model of P300 Amplitude

Johnson's (1986) triarchic model of P300 amplitude is really more of a summary and categorization of the antecedent conditions for P300 than a theory of the functional significance of the component. Johnson outlines a mathematical function in which subjective probability and stimulus meaning have additive effects on P300 amplitude, and information transmission has a multiplicative effect. Although Johnson does not directly address the question of the functional significance of the P300, his model is compatible with context updating.

The Consequences of the P300

One means of testing theories of the functional significance of P300 is to make predictions regarding the consequences that can be expected to accrue from variations in the putative P300-producing information-processing process, and then to test whether or not the presence, amplitude, or latency of the P300 is correlated with the predicted consequences.

The context updating model has been used to make predictions regarding two kinds of future behavior: strategic choices in performing an experimental task, and ability to remember events or items associated with the processing that produced the P300.

Strategic Information Processing

A key contention of context updating is that the P300 manifests a process that is concerned with strategic information processing (Donchin, Karis, Bashore, Coles, & Gratton, 1986; Donchin, Gratton, Dupree, &

Coles, 1988). That is, the process indexed by P300 involves changes in the strategy for dealing with future events, not the present trial.

One indication that this is the case is the fact that the P300 may occur after the response to the current stimulus (McCarthy & Donchin, 1981).

Donchin, Gratton, Dupree, & Coles (1988) found that in trials in a choice reaction time task in which the subject made a fast, incorrect response ("fast guesses"), the P300 occurred later than in other trials. Based on the context updating model, they hypothesized that the event evaluation process that gave rise to the P300 included some level of realization by the subject that an error had been committed. They predicted, therefore, that the amplitude of the P300 would be positively related to the degree of recognition of the error, and therefore would be predictive of future strategy changes. Results indicated that larger P300s on fast-guess trials were indeed associated with a shift to a slower and more accurate strategy on subsequent trials.

Memory and "Perfect Pitch"

On the basis of the context updating hypothesis, Klein, Coles, & Donchin (1984) predicted that individuals who had "perfect pitch" would not exhibit the usual large P300 in response to rare, target tones in an auditory oddball experiment. This prediction was supported by the data. Subjects with perfect pitch C1 and control subjects were required to count rare tones of a particular frequency. Control subjects, who needed to maintain (and, presumably, to refresh) a representation in working memory of the tones, exhibited the usual large P300s to rare targets. Individuals with perfect pitch, who could identify a musical tone from some permanent internal standard without reference to any recent stimulus trace carried in working memory, did not exhibit a P300 in response to target tones. Both groups of subjects showed normal P300s in a visual oddball task.

P300 Amplitude and Memorability of Events

If the P300 is a manifestation of the process of incorporating information into the schema, then a larger P300 may indicate more thorough incorporation of a particular item of information. If this is the case, then one could predict that items that evoke larger P300s upon initial presentation will be later recalled better than other items.

Karis, Fabiani, and Donchin (1984; Fabiani, Karis, & Donchin, 1986, 1990) investigated the relationship between P300 amplitude and subsequent recall in a series of experiments using a von Restorff design (von Restorff, 1933), in which subjects are presented with a series of items. A minority of the items presented are "isolates" that differ from other items in some critical feature (e.g., different type size for words). They found that isolated items later recalled elicited a larger P300 upon initial presentation than items later not recalled. This effect was found only when subjects used a rote strategy for remembering the items. They invoked the context updating hypothesis to explain the result in the following way: on trials when the process of context updating was undertaken to a greater degree, this was manifested in a larger P300 and also resulted in increased memorability for the eliciting item. When subjects used elaborate strategies for remembering the items, however, this effect was apparently swamped by the variability across items in the effectiveness of the strategies.

These researchers attempted to use homogeneous word lists, and variations in P300 amplitude may have had no relationship with the subjects' prior experience with particular stimuli. However, it may be the case that words that elicited larger P300s did so because they were more significant to the particular subjects due to some past experience— which would also make their occurrence a more memorable event and thus result in better memory performance for these particular stimuli. The possible relationship between remembered words (which elicited large P300s) and past experiences of the subjects was not investigated. One of the purposes of the research program proposed here is to determine whether or not stimuli that have particular significance to a subject that is not due to their relevance to the assigned experimental task but rather to their relevance to the subject's past experiences will result in a larger modification of the schema and an accompanying larger P300. This will be further discussed in subsequent sections.

THEORY AND PRACTICE IN THE NEW PARADIGM

Factors in Stimulus Set Design

The rationale for the hypothesis that probe stimuli relevant to significant life events will elicit a P300 even when the probes are explicitly task-irrelevant is discussed in detail below. Briefly, the predicted phenomenon is as follows. Research in the field of autobiographical memory has shown that certain kinds of cues are effective in evoking recall of memories of past events, and certain kinds of autobiographical events are most readily recalled. Some of the major factors that affect such recall are the recency, uniqueness, consequentiality, emotional involvement, and self-referral nature of the event. Events that are sufficiently salient are recalled when an appropriate relevant cue is presented. This phenomenon makes the occurrence of the cue (along with the subject's response to it) a significant event capable of invoking context updating and the concomitant P300. Probes relevant to such salient life experiences are predicted to elicit large P300s even if they are explicitly task irrelevant. This is what is meant by "implicit" task relevance.

In conventional polygraphy, relevant stimuli (i.e., questions) have been selected to be relevant to the event in question, maximally emotion-eliciting, and unambiguous (Reid and Inbau, 1977). Although polygraphers have developed considerable expertise in selecting relevant questions and structuring an interrogation, there has been little previous research on what types of information can best be detected through conventional polygraphy or what qualities an event must have to lend itself to such a procedure.

The Farwell Truth Detector, as pointed out previously, is not a lie detection system but rather an information detection system. In order to be detected, the information must be remembered. In this regard, previous research in the field of autobiographical memory can give us some guidance as to what types of events lend themselves to detection through this procedure and what types of stimuli will be most effective in detecting these events. This is discussed in the subsequent section.

What Makes the Probes Effective?

In the absence of relevant knowledge, and consequently of any special significance for the probe stimuli, the experimental design described here amounts to nothing more than an ordinary two-category oddball experiment of the kind that has been shown to produce P300s in numerous experiments over the last couple of decades. According to the context updating theory, the targets are particularly noteworthy due to the fact that they occur relatively rarely, the subject has memorized them, and he/she is required to push a special button when they occur. When these rare and relevant events occur, the subject takes note of them and updates the schema to include this new event and its significance. The manifestation of this process at the scalp is the P300.

What is it about the probe stimuli that makes subjects emit a P300 in response to them even when they are not explicitly task relevant? It is not enough that he/she should recognize them: trivially, every subject recognizes every meaningful stimulus to some extent (e.g., even if one's espionage contact was not wearing a green scarf, one recognizes what a green scarf is.) The prerequisite, according to context updating, is that the stimuli should be of a nature that they inspire the subject to take particular note of them, to revise his internal representation of the current operating environment when they occur. What must a stimulus do or be in order to produce this effect? Rarity is one condition that helps, but it is insufficient in the absence of some kind of relevance.

What kind of events will inspire a subject to update his/her schema? The events must be noteworthy for some reason. They must either be significant in and of themselves (i.e., play a role in the performance of an experimentally defined task, as do the targets), or, alternatively, they may take on significance because they trigger memories of a significant event. If one visits one's mother after a long absence, this tends to be a significant and memorable event. If one sees one's mother's picture after a long absence, looking at a picture may not in itself be a significant event, but the experience may take on significance in that it brings to mind other significant, memorable events that have taken place in the past.

What is it about past events that makes them significant or memorable? Previous research in the field of autobiographical memory can provide some insight in this regard. Autobiographical memory refers to memory of a person's life experiences (Rubin, 1986). Systematic study of the use of verbal cues to elicit autobiographical memories dates back to Galton's work of over a century ago (Galton, 1883), which is indeed not entirely dissimilar to the experimental design employed in the present series of experiments. Galton presented subjects with a verbal cue and asked the subject to describe a memory associated with the word. He recorded the reaction times to the cues. He described various types of recollections, and attempted to classify the words used to elicit them in terms of their relative efficacy. He also classified the events remembered according to the period of life in which they occurred. Galton's technique, and the taxonomic orientation it implies, have become popular among autobiographical memory researchers in recent years.

Autobiographical memory for specific events as experienced (as opposed to biographical facts such as one's birth date) is also referred to as personal memory. Flashbulb memory (Brown and Kulik, 1977) refers to a similar phenomenon. A substantial data base has accumulated regarding the variables that influence personal memory (Brewer, 1986). Events that result in personal memories that are well recalled (and hence would lend themselves to investigation with the technique described herein) tend to be 1) unique (Linton, 1979; White, 1982); 2) consequential (Rubin & Kozin, 1984); 3) unexpected (Linton, 1979; Rubin and Kozin, 1984); and/or 4) emotion-provoking (Rubin & Kozin, 1984; Smith, 1952; White, 1982). Events that tend not to be recalled are 1) repeated (Linton, 1975; Smith, 1952); and 2) trivial (Linton, 1975; Smith, 1952).

The qualities that tend to result in memorability often tend to co-occur (Brewer, 1986). Different writers have categorized and labeled them somewhat differently, but the kind of experiences referred to are similar. In a recent extensive investigation of one man's autobiographical memory Wagenaar (1986) used the term salience to refer to essentially the same qualities as uniqueness, consequentiality, and unexpectedness. Wagenaar tested his recall of thousands of incidents over a span of six years based on cues providing partial information as to who, what, where, and when the incident occurred. Who, what, and where were equally effective as cues. As has been found repeatedly by others, the time when an event occurred was not ordinarily effective as a cue to recall. In addition to salience, Wagenaar found emotional involvement in the original event to be a good predictor of memorability, and also found that pleasantness of an event was predictive of memorability.

Another factor that has been shown to influence autobiographical memory for events is the frequency with which the event has been rehearsed by subsequent recollection (Baddeley, 1990). (Baddeley, like Wagenaar, also noted the importance of salience and emotional involvement.) Moreover, events more distant in time tend to be remembered less well than more recent events (e.g., Rubin, 1982; Hudson & Fivush, 1987).

Autobiographical memories, of course, are not literal, accurate representations of the events remembered (Neisser, 1982; Bunuel, 1985). They contain the individual's interpretation of the event and concomitant thoughts, emotions, and motivations as well as sensory and perceptual features (Johnson, 1983; 1985). Although often inaccurate in details, they are often correct in expressing the meaning of the event for the individual. The factual information that is preserved in autobiographical memory tends to involve actors, actions, locations, and, to a lesser degree, temporal information (Conway, 1990). Autobiographical memories tend to be self-referential, and thus cues that involve the actor himself are particularly effective in eliciting them (Brewer, 1986). Autobiographical memories tend to be multi-faceted, that is, to contain sensory, perceptual, and reflective information (in fairly equal proportions), and to be related to other memories (Johnson, 1985).

What, then, does the literature on autobiographical memory reveal about what qualities a stimulus must have to function effectively as a probe? In other words, what qualities must an explicitly task-irrelevant stimulus have in order to elicit a P300?

First of all, let us review what takes place, according to our theory, when a probe stimulus elicits a P300 in a "guilty" subject. He/she has been given a task involving categorizing stimulus events as relevant (target—push the special button; these occur rarely) and irrelevant (everything else). Among the explicitly task-irrelevant stimuli are a few probes relevant to a past event. In the absence of relevant knowledge, a subject can follow a simple strategy: push the special button in the rare cases when a stimulus he/she recognizes (i.e., a target) comes up, and otherwise (in the frequent cases)

ignore the stimulus and simply press the other button. When the subject has the relevant knowledge of a significant event, something else takes place upon the arrival of a probe stimulus. Because of the memorability of the past event and the appropriateness of the cue, the arrival of the probe produces an effect that the irrelevant stimuli do not: it invokes the memory of the past event. Now there is another, separate, rare category of relevant events. Moreover, this phenomenon forces the subject to adopt a different strategy in responding to the stimuli if he is to conceal his knowledge (or even just follow instructions). Unlike an innocent subject, he can not simply press the target button for everything he recognizes as being out of the ordinary. When a noteworthy stimulus comes up, he must carefully and quickly distinguish whether it is noteworthy because it was on the list of targets (in which case he hits the target button) or because it has significance due to past experience (in which case he hits the irrelevant button). This serves to increase the relevance and noteworthiness of the! probe stimuli.

What qualities must the original life event and the probe that triggers memory of it have in order to produce such a memorable event and inspire an updating of the schema and the concomitant P300? In other words, what makes an effective probe? As we have seen in the above discussion of autobiographical memory, the ideal probe will have a number of qualities, although a subset of these qualities will in some cases be sufficient.

In general, the probes should refer to salient aspects of salient events. Attempting to detect trivial, ordinary, repeated everyday events does not promise much success.

The probes should, insofar as possible, refer to unique aspects of the situation being investigated, and the situation should itself be a unique one. If, for example, a subject has committed a hundred burglaries, "burglarized a house" is unlikely to be effective even if some of the burglaries are well remembered. Specific features that were unique to the particular situation investigated, for example, particular rare items taken, will tend to be more effective. The probes and the events they refer to should be consequential. For example, a bank robber may have passed by a laundromat on the way to the bank, and may have seen it clearly at the time. He also may have escaped in a blue ford truck with bullet-proof glass in the back window that protected him from the shots of the police. The latter would obviously be more memorable and consequently make for a better probe.

When possible, it would be a positive factor to include probes that referred to happenings within the situation under investigation that were unexpected by the subject at the time, although in practice this may often not be possible.

Probes that refer to aspects of the event that are likely to have been rehearsed frequently by subsequent recollection (e.g., items in an espionage case that would have been likely to have been reported to others) would have increased efficacy.

When possible, it would be more effective to use probes that refer to more recent events rather than events in the distant past.

Probes representing who was involved, what happened, and where it took place will be more effective, in general, than cues based on when the situation happened.

Probes that involve action and actors should be particularly effective, especially those involving actions undertaken by the subject himself.

The Role of Emotion

There are two contexts in which emotion could play a role in the phenomenon investigated in the present research: at the time of the initial event that was stored in memory, and at the time of the probe stimulus event that elicits the P300.

Certainly, emotions similar to those experienced in the initial event may be present at the time of the probe stimulus, and there is some evidence that emotional intensity in response to the stimulus may enhance P300 amplitude (see discussion below). However, it is equally clear that the experience of strong emotions at this time is not a prerequisite for the elicitation of the P300. There is no reason to suppose that the subjects in the present mock crime experiment—who consistently displayed P300s when they were "guilty"[13] would have experienced strong emotions in response to the probe stimuli, and none of them exhibited or reported emotional responses in debriefing.

In some cases, emotion-eliciting probes may be effective in eliciting P300s. Yee and Miller (1987; see also Yee and Miller, 1988) investigated the role of emotion in the elicitation of the P300 using a fixed-foreperiod, warned reaction time design on high- and low-fear subjects (as measured by a mutilation fear questionnaire). Six-second warning tones informed the subject whether an upcoming slide would be pleasant (landscapes, young animals, food) or unpleasant (blood injury or medical procedures). Fast reaction times (less than 250 msec) to tone offset/slide onset affected the duration of the subsequent slide presentation. Unpleasant slides were terminated immediately following a fast reaction time, and pleasant slide presentations were prolonged following a fast reaction time. A slow reaction time resulted in termination of a pleasant slide or prolonging of an unpleasant one. P300s were measured to tone onset and tone offset/slide onset.

Yee and Miller found larger P300s to tone onset in high-fear subjects than in low-fear subjects. Negative slides resulted in both larger P300s and faster reaction times to slide onset than positive slides. They pointed out that these results are consistent with the interpretation that P300 amplitude was affected by emotional intensity, rather than emotional valence. (In view of the nature of the slides and the reaction time difference, the valence difference in P300 to slide onset probably corresponded with an intensity difference, with the negative slides being more intense or motivating.) Thus, probe stimuli that are of an emotional nature, perhaps particularly of a negative emotional nature, may be in some cases more effective in eliciting P300s. As discussed above, however, this emotional factor is not a prerequisite for probe stimuli to be effective.

Another instance of P300s that were elicited in an unusual experimental design may have involved emotional, as well as cognitive and sensory, factors. Putnam and Roth (1985) reported P300s in response to auditory stimuli of sufficient intensity that they also elicited startle eye blinks. P300 amplitude increased with increased stimulus duration but not with decreased rise time. P300 amplitude habituated with repeated presentation of the same stimulus. It is unknown what emotions or cognitive activity would have been elicited by such high-intensity stimuli in the absence of an experimenter-assigned task. According to the context updating model, the occurrence of the stimuli became a sufficiently noteworthy event that it demanded revision of the schema, perhaps due to the unpleasant nature of the stimulation. To what degree this phenomenon involved emotional as opposed to purely cognitive factors can not be determined at this point. It is important to note that the fact that the subjects were not instructed to perform a task does not necessarily mean that the stimuli were treated as irrelevant by the subjects. For example, the subjects may have been performing a time estimation task for which the stimuli were very relevant (Donchin & Coles, 1988b), and the intensity (and resulting unpleasantness) may have affected the relevance of the stimuli for the subject. As Donchin and Coles (1988b) point out, without overt response measures or debriefing of the subjects it is impossible to know what the subjects were indeed doing in the experimental situation.

The evidence on the effect of emotions at the time of the original event on the formation and later recall of autobiographical memories is contradictory. On the one hand, several researchers mentioned above (Rubin & Kozin, 1984; Smith, 1952; White, 1982; Wagenaar, 1986) found that emotional involvement at the time of the original event had a salutary effect on the formation and later recall of autobiographical memories. Kleinsmith and Kaplan (1963) found that negative emotional words were poorly recalled after a short interval (a few minutes) but were better recalled than neutral words after a period of a week. Leippe, Wells, and Ostram (1978) found that the higher levels of arousal accompanying the witnessing of a more serious simulated crime resulted in better recognition of the perpetrator. Although emotional involvement has often been found to increase memorability, it has not been found to be a prerequisite for memorability, but only one of several factors that may be present in the production of a memorable event (Baddeley, 1990).

Others, beginning with Freud, have held that negative emotions cause memories to be suppressed. If the recall of an incident that a probe is designed to trigger is inhibited, then the phenomenon described above in which the recall produces an updating of the schema may take place to a lesser degree, and the probe may be less effective in eliciting a P300.

There is some evidence for the contention that negative emotions make the associated events less memorable. Loftus and Burns (1982) showed subjects different versions of a film of a simulated robbery, one version containing graphic violence. Subjects who viewed the violent film exhibited poorer retention of details. Peters (1988) asked subjects to recognize a nurse who had subjected them to a painful inoculation and an individual with whom they had had a neutral interaction; recognition of the nurse was consistently poorer.

There are a number of documented cases in which perpetrators of violent crimes exhibit extremely poor recall—and in some cases total amnesia—regarding the event (Bower, 1981; Taylor & Kopelman, 1984).

In general, the studies finding increased memorability with emotional involvement are those that involved a relatively low level of arousal, whereas the cases where memory was impaired, particularly cases of substantial impairment, often involved very high levels of stress (Baddeley, 1990).

From the preceding discussion it is clear that there is no obvious formula for the ideal emotional content for probe stimuli. The evidence (and our experience with Experiment 1 in particular) point to the conclusion that strong emotions need not be present either at the time of the initial event or at the time of the presentation of the probe in order for the probes to elicit a P300. However, in some cases emotional involvement in the initial event may increase its memorability and hence the P300-eliciting effect of the probes. In other cases, particularly when extremely strong negative emotions are involved, the effect of emotions at the time of the original event is much more unpredictable, and may result in either increased or, in some cases, dramatically decreased memorability. (The implications of this for future research are discussed in the General Discussion.)

Hypotheses and Theoretical Significance of This Research

In conventional psychophysiological detection of concealed information, the task at hand for a guilty subject is to appear innocent by responding the same to the relevant and irrelevant stimuli. The information stored in the brain regarding the crime-relevant stimuli is not task-relevant for this endeavor: it is not necessary or useful in performing the task effectively. Nevertheless, this stored information reveals itself by increasing the level of emotional arousal of the system in the presence of the relevant stimuli, thus increasing the physiological activation of the system (Reid & Inbau, 1977) and calling forth "Sappho's famous symptoms" (Plutarch, first century A.D./1952).

In previous research on the P300 and other event-related brain potential components, any signs of information of whatever nature stored in the brain that is not explicitly task-relevant have been absent (Sutton, Tueting, Zubin, & John, 1967; Duncan-Johnson & Donchin, 1977). When information that is relevant to the experimental task (and relatively rare) is delivered, a P300 is elicited. When the same information is delivered to the same subject but is not task-relevant, generally no P300 appears.

If the P300 is a manifestation of the process of revising one's internal representation of the current operating environment, then it may be possible to create a situation such that the presence of concealed information stored in the brain will reveal itself by invoking this information-processing process.

The hypothesis advanced here is that the presence of concealed information stored in the brain that is sufficiently significant to the subject will result in the subject taking particular note of stimuli relevant to that information, thus invoking context updating and the concomitant manifestation of a P300. The concealed information will reveal itself in this manner due to the activation of a specific information-processing function, and not through modulation of the level of emotional and physiological arousal (Donchin, Karis, Bashore, Coles, & Gratton, 1986).

The predicted result of a larger P300 to probe than to irrelevant stimuli in the research program outlined here would be a significant new finding in several ways. It would constitute the first psychophysiological detection of concealed information through central nervous system measures; the first realistic detection through cognitive, as opposed to emotional, means; and the first detection through a specific information-processing function as opposed to a general state of activation of the organism. (After the research reported here was completed, Norman Ansley, the editor of Polygraph, brought to the author's attention a feasibility study published in that journal in 1975 in which Pinneo, Johnson, & Mahoney (1975) recorded ongoing EEG activity in conjunction with a conventional interrogative polygraph test. The authors characterized their results as "inconclusive." They did not report the percentage of correct classifications, but indicated that it varied widely with different subjects. Some of the results reported here (Experiment 2) were first reported by Farwell & Donchin (1986).) It would also constitute an observation of a P300 in response to explicitly task-irrelevant stimuli, and therefore would provide support for models of the functional significance of the P300, such as context updating, which could explain such a phenomenon. (As is described in detail in subsequent sections, the results were as predicted here.)

Such a finding would provide evidence that clearly distinguishes between different models of the functional significance of the P300. According to brain deactivation/closure theories (Desmedt, 1980; Verleger, 1988), the P300 is not a manifestation of an active, information-processing process, but rather a modulation of the level or cortical activation, specifically a widespread cortical deactivation on the background of a state of activation that has accompanied anticipation of the stimulus. "P300 does not index actual processing activities." (Desmedt, 1980). "this deactivation is not a psychological process . . . it does not play a direct role in information processing . . . Just as the blood flow is physiological, the deactivation is physiological." (Verleger, 1988). According to the context updating model, by contrast, the P300 is a manifestation of a specific, active, information-processing function, namely that of updating one's internal model of the current operating environment (Donchin, 1981; Donchin, Karis, Bashore, Coles, & Gratton, 1986; Donchin & Coles, 1988a; 1988b).

In the proposed research program, the arrival of a probe stimulus, if the subject is guilty, will result in a sudden increase in task difficulty. An irrelevant stimulus (or a probe for an innocent subject) can be easily dismissed as irrelevant since it has no particular significance to the subject. When a probe is seen and noted by a guilty subject, however, he must then determine whether he recognizes it because of its experimental task relevance (in the case of a target, which has been explicitly identified and made task-relevant by experimental instructions) or because of its relevance to other past information (in the case of a probe). These two different noteworthy kinds of stimuli demand opposite responses, which must be performed quickly. One hypothesis of this study is that the increase in task difficulty that this brings about will affect button press latencies. It is predicted that for guilty (but not innocent) subjects button press latencies will be longer and accuracy less for probes than for irrelevants, reflecting the increased task difficulty involved in dealing with the explicitly irrelevant but implicitly relevant probes.

This sudden increase in task difficulty upon the arrival of a probe is certainly not an impetus for brain deactivation. Quite the contrary. If cortical voltage is simply an inverse indicator of the level of activation, then one would predict, if anything, increased negativity following the probes. As Verleger (1988) put it, "P3s become smaller the more additional processing is required." As subjects are "more activated by" a stimulus, the resulting negativity reduces P300 amplitude. According to the brain deactivation/closure hypothesis, then, P300s amplitude should be reduced, rather than increased, following probe stimuli.

Another clear indication that the brain deactivation/closure hypothesis is incompatible with a finding of increased P300 amplitude following probe stimuli is Verleger's (1988) description of the "subtle psychological consequences of the deactivation indicated by P3." " . . . this deactivation plays its part to form the basis of feelings of relaxation." Clearly, relaxation is quite the opposite of what a guilty subject will experience upon being confronted with a stimulus relevant to his crime. Deactivation/closure, then, clearly predicts a reduction in P300 amplitude, or an increase in negativity, following probe stimuli.

Context updating makes the opposite prediction. If the P300 is a manifestation of the specific, active process of context updating, then the probes, being particularly noteworthy and thus necessitating a relatively large revision of the current schema, should result in a large P300, i.e., a large positivity, and not a smaller positivity or a negative deflection. This is the hypothesis advanced in this research program.

If the P300 is the manifestation of an active, information-processing function, what is the nature of that function? Previous research has indicated that it is of a nature that it can be turned on and off at will depending on whether or not the subject has been instructed to engage in a task that makes particular stimuli task-relevant. The finding of a large P300 in response to the explicitly task-irrelevant probes would lend support to the contention that P300 manifests an automatic housekeeping function, one that cannot be suppressed so long as an individual becomes aware of any information sufficiently salient that it demands a revision of the schema.

This predicted result is in some ways reminiscent of the von Restorff study results reported by Karis, Fabiani and Donchin (1984; Fabiani, Karis, & Donchin, 1986, 1990). In those studies items that were later recalled elicited a larger P300 on initial presentation than items later not recalled. Fabiani et al. hypothesized that the process of context updating took place, for some unknown reason, to a larger degree for these later-recalled items, resulting in a larger manifestation of this process in the form of a P300. The later-recalled items may have in fact been particularly noteworthy for individual subjects upon initial presentation due to some relationship to information already stored in the subject's brain. Alternatively, the differences in the degree of implementation of the context updating process may not have been stimulus driven. The Fabiani et al. studies do not tell us what, if anything, characterized the particular stimuli within a category—or the significance of these stimuli for particular subjects—that evoked particularly large P300s. Whatever the cause, the result was greater memorability.

In the present research program we begin with a set of probe stimuli that are not differentiated from others by experimental instructions, but are expected to be particularly noteworthy or memorable to certain subjects due to their related past life experiences. The prediction here is that stimuli that are more noteworthy or memorable for a known reason will—like the stimuli in the von Restorff experiments that either were or became upon initial presentation more memorable for an unknown reason—elicit larger P300s. Again, this result is, according to context updating, due to the fact that these stimuli elicit a more substantial revision of the schema than other stimuli.

In summary, then, the proposed program of research is designed 1) to provide a new paradigm in the psychophysiological detection of concealed information; 2) to distinguish between different major theories of the functional significance of the P300; 3) to substantiate and expand the context updating model; 4) to extend the realm of the antecedent conditions for the P300 and explain this in terms of an extension of the context updating model; and 5) to extend the findings of previous memory-related research on the P300.

Possible Experimental Outcomes and Theoretical Significance

The following is an account of the possible experimental outcomes, and the theoretical significance of each.

In the alternative outcomes discussed below, I have not considered the finite but very remote possibility that the targets would fail to elicit larger P300s than the irrelevants. Such a finding would constitute a failure to replicate a highly robust result that has been found in many experiments under widely varying conditions. Such a finding would be very difficult to interpret. The most likely explanation would be that an error was made by the experimenter in some phase of data acquisition or analysis. In this discussion I proceed on the assumption that targets do elicit larger P300s than irrelevants. The critical question is, what is the response to the probe stimuli? The possible alternatives are as follows.

1) P300s in response to probes are larger than P300s to irrelevants.

This would indicate that the presence of information stored in the brain relevant to a particular stimulus, in the absence of an explicit task demanding the utilization of the information, can be a sufficient condition for the stimulus to evoke the information-processing activity manifested in P300. Explicit task relevance would not be a viable necessary condition for the P300. Implicit task relevance would take its place as a sufficient condition, in the task relevance dimension, for the elicitation of P300. This would support the hypothesis that the P300 is a manifestation of a specific, active, information-processing process such as context updating.

Such a result would be incompatible with the brain deactivation hypothesis of the functional significance of P300, particularly if this result were combined with a finding of increased manual response latency and/or decreased accuracy. These behavioral results would indicate increased task demands, necessitating increased brain activation rather than deactivation.

This result, and its theoretical implications, would form the basis for a new paradigm in the psychophysiological detection of concealed information, based on fundamentally different principles and practice than conventional interrogative polygraphy. Having demonstrated that implicit task relevance can indeed call forth a specific information-processing activity manifested in a psychophysiologically measurable event, we could proceed to refine the theoretical understanding and practical applications of this phenomenon, and further develop it as a means of psychophysiological detection of concealed information.

2) The probes fail to elicit a P300 response that is distinguishable from that of the irrelevants.

This would indicate that implicit task relevance may not be a sufficient condition for the elicitation of a P300, and explicit task relevance may be necessary. This result would not clearly distinguish between information-processing (context updating) and activation (brain deactivation) theories of P300.

However, such a finding would be difficult to explain within the context updating theory. Certainly, one's internal representation of the current operating environment must be able to be revised upon the arrival of information that is not explicitly relevant to an experimentally assigned task. If the P300 does indeed manifest the revision of the schema, then it should be possible to elicit a P300 with implicitly task-relevant, explicitly task-irrelevant stimuli. A negative result would not, however, be conclusive here: possibly the chosen stimuli were simply not sufficiently salient for the subjects.

Such a finding would be somewhat less problematical for the brain deactivation theory of the P300. Verleger (1988) states that the P300 is elicited by stimuli in a series that are "awaited" and "expected." One could explain the lack of a P300 in response to probe stimuli by stating that the subjects, for whatever reason, were not actively "awaiting" the probe stimuli.

3) The probes elicit an increased negativity.

It is possible that the probes, as compared with irrelevants, will elicit an increased negativity (indicating deactivation), perhaps followed by a large apparent positivity (constituting return to baseline). This would support the hypothesis that slow ERPs are manifestations of the modulation of the level of activation of areas of the cortex. It would further indicate that implicit task relevance was a sufficient condition to elicit such cortical activation.

Such a result would strongly argue against the context updating model of the P300, which would make the opposite prediction, as explained in (1) above.

This is the result predicted by the brain deactivation hypothesis of the functional significance of the P300. If the positive-going P300 is a manifestation of deactivation of the cortex, and negative scalp potentials are manifestations of brain activation, then the highly activating probe stimuli should produce the opposite of a P300, i.e., a negative-going component.

THE EXPERIMENTAL PROGRAM

Experiment 1

Subjects

Twenty subjects (12 female), whose ages ranged from 19 to 27 years, participated in the study. All subjects were undergraduate or graduate students who were paid for their participation.

Procedure

Subjects were trained by an interactive computer program to perform one of two different mock espionage scenarios, which they then proceeded to carry out. Each subject learned one scenario and was unaware of the other scenario. Thus, each subject could be tested on the knowledge of the scenario which he or she experienced (this was that subject's "guilty" scenario) as well as on the scenario of which he was innocent. Each of the scenarios required the subjects to go to a specific location and meet a person with whom a password was exchanged. The subject then asked that person for a file which had a particular designation and which pertained to a specific operation. Six critical details were associated with each of the two scenarios. Knowledge of these details could be used as indication that the subject participated in the scenario. (The Appendix presents the information associated with each of the scenarios, as well as all the other stimuli used in the study.)

The interactive training program consisted of a series of instructions as to the critical items which the subjects were instructed to memorize and actions they were to follow. The instructions were repeated several times, and subjects were repeatedly tested on the instructions until they had responded correctly at least five times to questions regarding each of six key items. Following the training session, when the computer had established that the subjects had learned the scenario to criterion, they were instructed to undertake the mission. In each case, the appropriate file folders were handed to the subject and he/she proceeded to the assignation and exchanged information and files with his/her contact.

One day after executing the scenario each subject underwent a brain-wave-based examination designed to test if the subject possessed "guilty" knowledge.. Subjects were tested for knowledge of each of the two scenarios, the one in which they had actually participated and the other scenario of which they knew nothing. Subjects were tested in three blocks for each of the two scenarios. Blocks of scenario 1 alternated with blocks of scenario 2. Note that scenario 1, of which half the subjects were guilty, was tested first for all subjects. Thus, the order of testing for guilty/innocent scenarios was counter-balanced across subjects. Two guilty knowledge tests were administered, one based on ERPs and one on skin conductance as measured by a conventional polygraph used in detection of deception. (After the completion of the Farwell Truth Detector test, we conducted a conventional guilty knowledge test of the type described by Lykken (1981). We recorded electrodermal response only. This measure did not consistently discriminate between the guilty and innocent subjects. However, the circumstances of testing were substantially different than those used in actual conventional polygraph examinations, and for this reason it would be inappropriate to draw any conclusions from these data. This phase of the study will not be further discussed in this paper.)

The Testing Session

Stimuli were presented visually on a video screen under computer control, and the ERPs elicited by each stimulus were recorded and stored on tape for off-line analysis. Each stimulus consisted of two one-syllable words. Stimulus duration was 300 msec. The inter-stimulus interval was 1550 msec.

The subjects were told that the stimuli would be two-word phrases. Some of these phrases were arbitrarily designated as "targets." The subjects' assigned task was to press one of two microswitches whenever they saw a target and to press another microswitch when they saw any other item. There were in fact three categories of stimuli. Among the non-target stimuli we included the "probes," which were phrases referring to the six critical items associated with each scenario. The remaining non-target stimuli were true "irrelevants."

For each of the two scenarios subjects were tested in three blocks of 144 trials per block. On each trial we presented the subject with a two-word phrase on the screen, either a targets, an irrelevant, or a probes. The three categories were presented in a random order. The set of targets contained six phrases. Each of the six target items was repeated four times in each sequence, so that the total number of target trials was 24, or 17% of the trials. The remaining 120 trials could be derived from one of two stimulus sets. The true irrelevants included the items which bore no relationship to either of the scenarios. For each target there were four similar irrelevants, for a total of 24 unique irrelevants. Each of these irrelevant stimuli was repeated four times in a block for a total of 96 irrelevant trials. The third set of stimuli constituted the probes. These were six phrases directly relevant to the scenario tested by the sequence. Each probe was repeated four times, so that there were 24 probe trials. Note that as far as the innocent can determine the series consists of targets and irrelevants, with 17% of the former and 83% of the latter. For the guilty, 17% of the trials are targets, 17% are probes and 66% are irrelevants.

The design of the test is summarized in Table 1. The phrases used as targets, probes, and irrelevants for each scenario are listed in the Appendix.

Note that the subject pressed a switch in response to every stimulus. One hand was used to respond to the targets and the other hand responded to the probes and the irrelevant stimuli. Like probes, targets were relatively rare, appearing one out of every six stimuli.

Prior to each block, a list of the target stimuli for that block appeared on the screen. The experimenter read the list aloud, then the subject read the list aloud, and then the subject was asked to recall the list and was corrected if any errors or omissions occurred. The subject was then instructed to press one microswitch following the presentation of a target stimulus, and another microswitch following any other stimulus. Subjects were instructed to press the switch as quickly and accurately as possible. The list of target stimuli was erased from the screen before the stimuli were presented.

Every 36 trials (that is, following one presentation of each stimulus) the stimuli were randomized again, and the next 36 trials were presented. This was repeated four times each block, for a total of 144 trials per block.

Data Acquisition

The electroencephalogram (EEG) was recorded from Ag-AgCl Beckman Biopotential electrodes placed at the Fz (frontal), Cz (central), and Pz (parietal) sites (10–20 International System), and from the right mastoid. All sites were referred to the left mastoid. In off-line analysis, half of the right mastoid/left mastoid signal was subtracted from each channel, so that the reference was in effect the average of the mastoids. Electrooculogram (EOG) was recorded from sub- and supraorbital electrodes (above and below the right eye). The subjects were grounded at the forehead. Electrode impedance did not exceed five kilohm. Brain electrical activity was amplified by Van Gogh amplifiers with low- and high-pass filters set at half-amplitude frequencies of 35 and 0.02 Hz, respectively. These signals were digitized at a rate of 100 samples per second. ERPs and button press latencies were recorded on tape for off-line analysis.

Prior to data analysis, all data were digitally filtered using a 49-point, equal-ripple, zero-phase-shift, optimal, finite impulse response, low-pass filter with a passband cutoff frequency of 6 Hz and a stopband cutoff frequency of 8 Hz. (For a discussion of digital filtering of ERPs, see Farwell, Martinerie, Bashore, Rapp, & Goddard, 1991.)

All trials, including those with the EOG artifact, were recorded, and data from all trials were included in the average response time results. However, only those trials with a range of EOG activity of less than 98 microvolts were included in the ERP analysis and in the trial counts that determined the number of trials presented.

Results

Event-Related Brain Potentials

Figure 2:
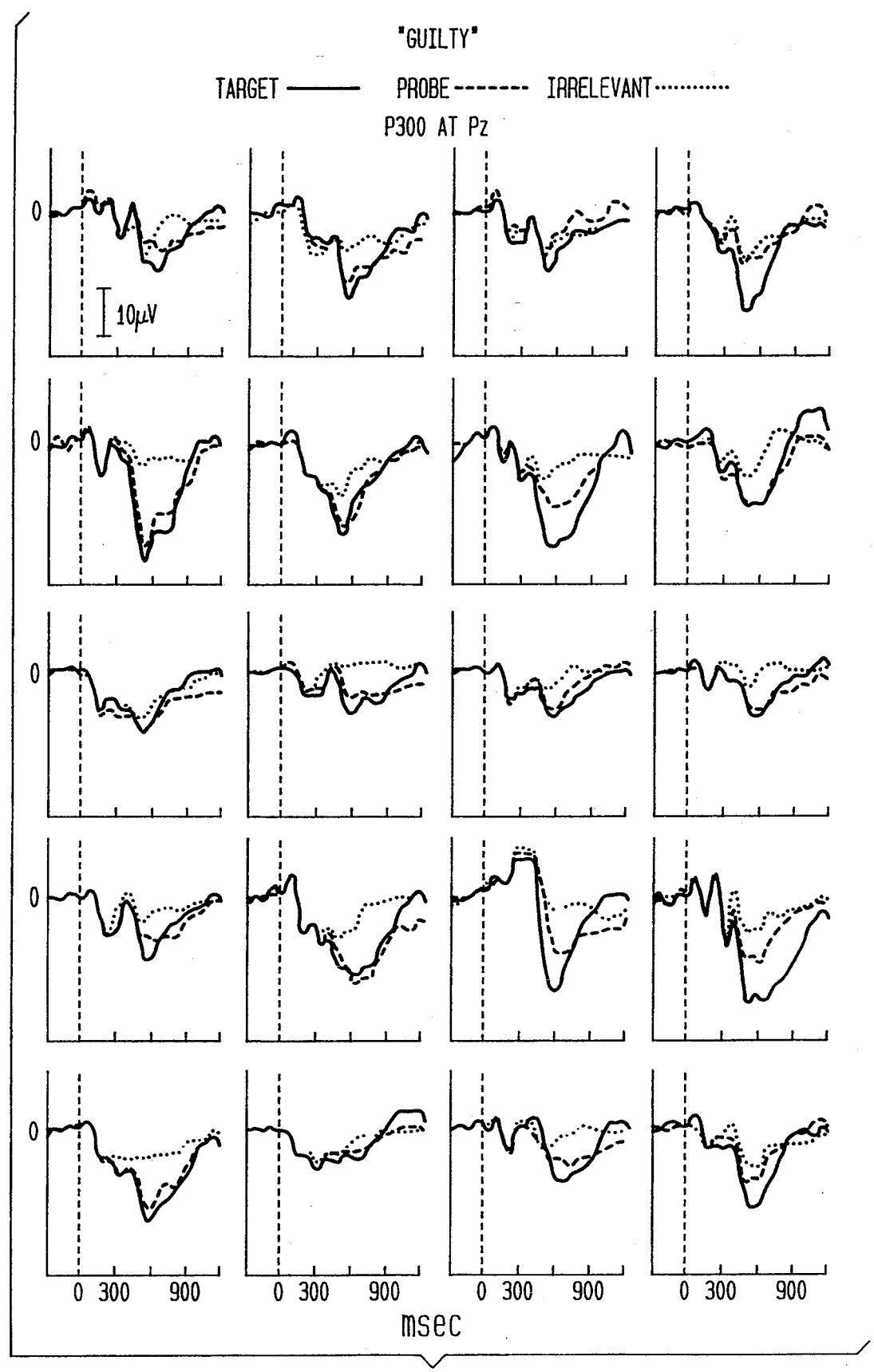
FIG. 2 illustrates ERPs (graphs) for each of 20 subjects in the "guilty" condition (Experiment 1). Note the Probe wave-form is clearly distinguishable from the Irrelevant, and similar to the Target.

The average ERP responses for artifact-free trials of each trial type at the Pz electrode site for each of the 20 subjects in the guilty condition are displayed in FIG. 2. ERPs for the same subjects in the innocent condition are displayed in FIG. 3.

The responses were as predicted. As can be seen in the figure, a large P300 was elicited by the target stimuli, but not by the irrelevant stimuli. The probes elicited a P300 when they were relevant to the subject's "crime." A very small P300, if any, was elicited by the probes when the subject was "innocent."

Data Analysis

The data analysis task in this study was to assess the similarity, for each subject, between the probe ERP and the ERP elicited by the other two stimuli. Furthermore, it was necessary to employ a method of analysis that would give a statistical confidence for each individual determination of "guilt" or "innocence." However, in order to increase the signal-to-noise ratio to a workable level, it was necessary to collapse all of the trials of each type for an individual case to one average-and thus to eliminate any information on the distribution of ERP responses within an individual case. Moreover, any parametric estimate of the moments or distribution of correlations would not be valid, since the distribution of correlations violates the assumption of normality.

The statistical technique of bootstrapping (Efron, 1979; Wasserman & Bockenholt, 1989) provides one solution to this problem. To evaluate the significance of the apparent differences in FIGS. 2 and 3, the three trial types were compared using an iterative sampling bootstrapping procedure. Bootstrapping provides an estimate of the sampling distribution of a parameter when only a limited number of samples are available by obtaining many random sub-samples from the available data and computing the parameter anew for each of these sub-samples. The distribution of these values approximates the actual distribution.

We used bootstrapping to estimate the sampling distribution of two correlations: the correlation between the average of the probe trials and the average of the irrelevant trials, and the correlation between the probe average and the target average. In our computations we used "double-centered" correlations (i.e., the grand average waveform, or the grand mean for all trials of all types was subtracted from the probe, target, and irrelevant average wave-forms prior to the correlation computations). If the correlation between the probe and target trials is significantly greater than the correlation between the probe and irrelevant trials, then we can conclude that the probe ERP responses are more similar to the targets (where a P300 is present) than to the irrelevants (where there is no P300). If this is the case, then we can conclude that the subject recognizes the probes as a separate, rare category—that is, of crime-relevant events-and therefore that the subject is "guilty." Similarly, if the correlation between the probe and irrelevant trials is greater than the correlation between the probe and target trials, then we can conclude that the subject is "innocent."

The procedure was as follows. First, we averaged each four irrelevant trials, so we had an equal number of probe, target, and irrelevant trials, approximately 72 of each (24 from each of three blocks). We created 100 random samples. The samples were taken with replacement. In each of 100 iterations we selected 72 of each of the three types of trials, yielding for each iteration three average ERPs. Each average was based on the 72 epochs selected for that iteration from one of the three trial types. We computed the probe-target and probe-irrelevant correlations for each iteration. Thus, the process yielded two groups of 100 correlations each. The distribution of these 100 correlations served as an estimate of the sampling distributions of the correlations. We then compared the distributions of the probe-irrelevant and probe-target correlations.

Figure 4:
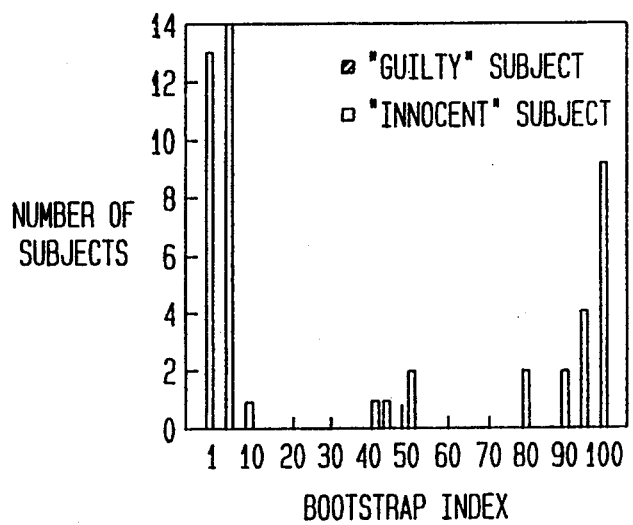
FIG. 4 is a graph of Bootstrap Index for "Guilty" and "Innocent" Conditions for a number of subjects.

For each subject we counted the number of iterations on which the probe/target correlation exceeded the probe/irrelevant correlation. This value is called the "bootstrap index" in the following discussion. In FIG. 4 we show the distribution of the bootstrap index for the 40 tests we conducted. FIG. 4 illustrates the distribution of the bootstrap statistic for all 40 tests conducted in Experiment 1. Dark bars indicate the number of subjects who were "guilty" and were assigned a given bootstrap value. Light bars show the same data for the "innocent" subjects. (Note the non-linear scale on the X-axis: the highest and lowest 1% and 5% are separate divisions, whereas all intermediate divisions are in increments of 10%. Although it provides more information, this scaling method reduces the visual impact of the correctly classified subjects' data.

The number of tests, labeled for guilt and innocence, corresponding to each index is plotted in the figure. It is evident that most guilty tests are associated with the lower values of the bootstrap index; the higher values of the index are associated with tests in which the subjects did not possess the concealed knowledge. Five tests, two of the guilty and three of the innocent, fall in the middle of the range.

Figure 5A:
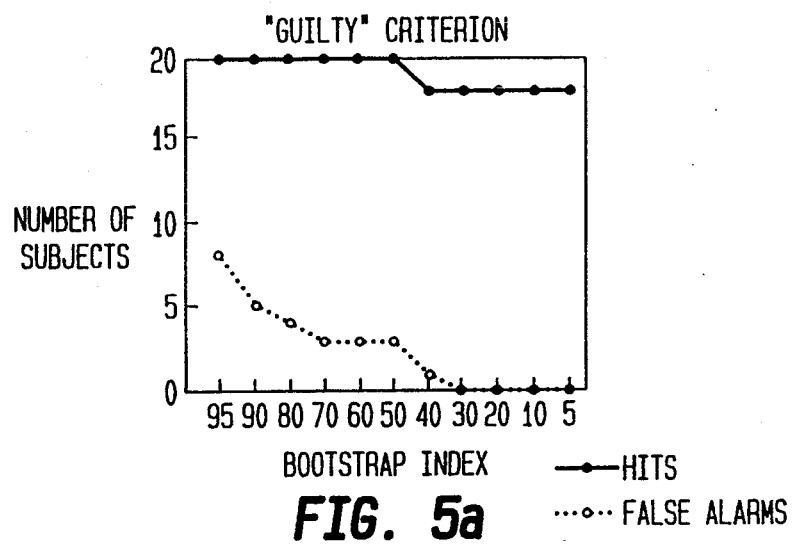
FIGS. 5a and 5b are two graphs plotting Bootstrap Index and Number of Subjects for "Guilty" and "Innocent" criteria, respectively, to represent Classification Accuracy as a function of Criteria.
Figure 5B:
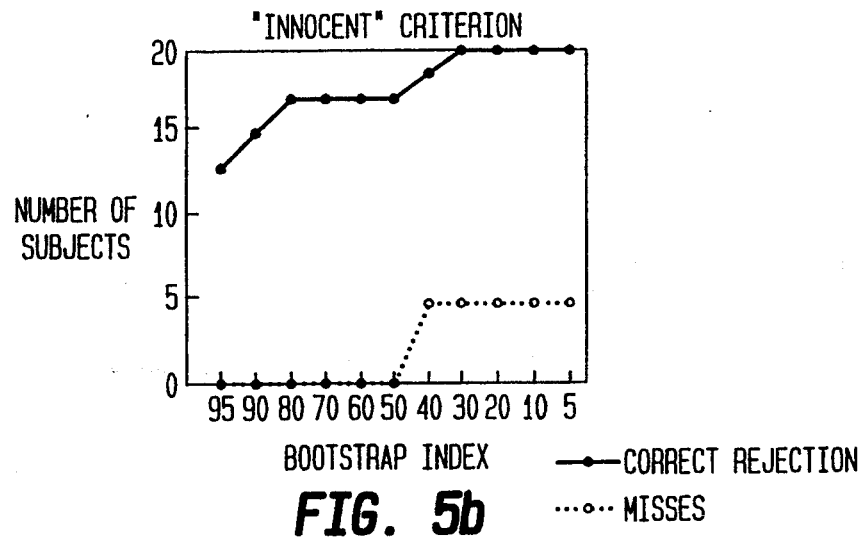

A decision regarding the guilt or innocence of a given subject depends on comparing his bootstrap index with criterion levels for guilt and innocence. For example, we can decide to require that at least 80% of the iterations will declare the subject as innocent before innocence is accepted (bootstrap index of 0.80 or more). A corresponding low limit on the index can be set, which if passed, the subject will be declared guilty. The data in FIG. 4 suggest that we have considerable leeway in setting the criteria. This point is made also in FIGS. 5a, 5b, which plot the outcomes of all possible decision rules for all the tests. FIGS. 5a,5b illustrate accuracy of the guilty/innocent classification as a function of the bootstrap statistic used for determining guilt or innocence. A "hit" is a guilty subject classified as guilty; a "correct rejection" is an innocent subject classified as innocent; a "false alarm" is an innocent subject classified as guilty; and a "miss" is a guilty subject classified as innocent.

The results of the bootstrapping analysis for one set of criteria are tabulated in Table 2. Table A summarizes the accuracy of determinations.

Table 2A: Accuracy of determinations, Experiment 1. In the 87.5% of the cases where a determination was made, 100% of the determinations were accurate. Positive and negative predictive values reflect the probability that guilty and innocent subjects, respectively, will be correctly deter-mined, when a determination is made (i.e., excluding indeterminates). Validity reflects the overall probability of correctly determining a subject's state.

Decision rule:

Bootstrap statistic<0.10→Guilty
Bootstrap statistic>0.70→Innocent
Bootstrap statistic>=0.10 and <0.70→Indeterminate Again, we have considerable leeway in setting the criteria while maintaining high accuracy of classification. Except for five subjects, whose results are neither strongly innocent nor strongly guilty, all of the guilty subjects have scores of 0.06 or less and all of the innocent subjects have scores of 0.80 or more. Tables 2B and 2C list the determinations for each of the guilty and innocent cases respectively.

Tables 2B & 2C. Determinations and statistical confidence, Experiment 1. Bootstrap statistic is the proportion of iterations (out of 100) where the correlation between the probe and irrelevant wave-forms at Pz was greater than the correlation between the probe and target wave-forms. Note that a higher value indicates "innocence" and a lower value indicates "guilt."

These tables also tabulate the bootstrap index, the proportion of iterations of the bootstrap procedure in which the probe-target correlation was greater than the probe-irrelevant correlation (i.e., the statistical confidence for each determination). Note that a high bootstrap index is an indication of innocence and a low bootstrap index is an indication of guilt.

It is clear that any guilty criterion that is 0.06 or greater will correctly identify at least 18 of the 20 subjects as guilty. Similarly, any innocent criterion 0.80 or less will correctly classify at least 17 of the innocent subjects. Any guilty criterion of less than 0.36 will not misclassify any innocents as guilty; any innocent criterion greater than 0.45 will not misclassify any guilty subjects as innocent. If the guilty criterion is set anywhere between 0.06 and 0.35 (inclusive) and the innocent criterion is set anywhere between 0.48 and 0.80 (inclusive), the result will be the same: 35 correct classifications, and no incorrect classifications. If the cases lying between these innocent and guilty criteria are classified as indeterminate, five indeterminate classifications will result. In no case, given the indeterminate class, do we have either a false positive or a false negative.

It is clear that wherever the decision criteria are set within quite a large range, there are 18 clearly guilty and 17 clearly innocent subjects, with five subjects close neither to the clearly guilty group nor to the clearly innocent group.

Scalp Distribution

Figure 3:
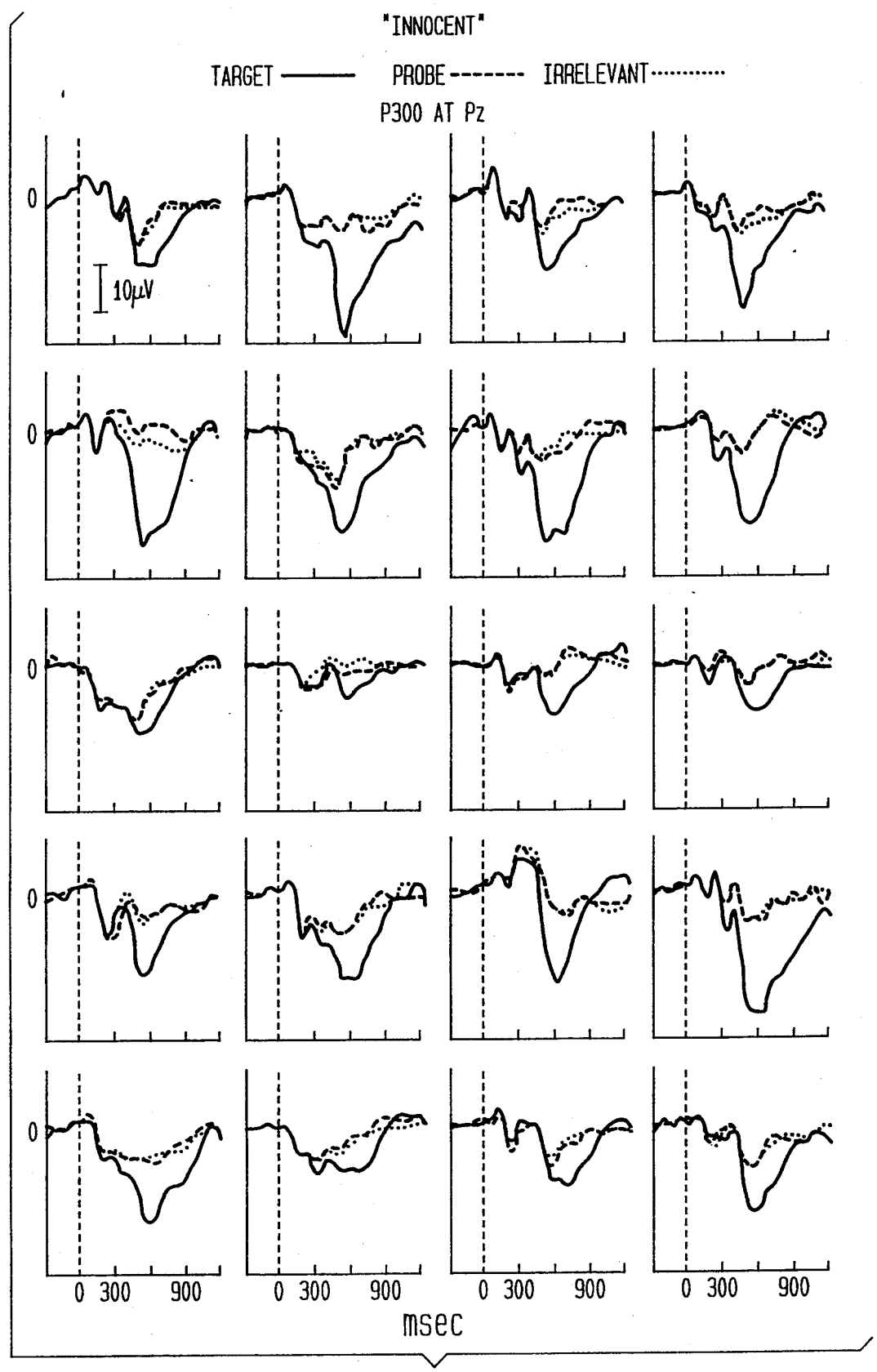
FIG. 3 illustrates ERPs (graphs) for each of 20 subjects in the "innocent" condition (Experiment 1). (Subjects are the same as in FIG. 2). Note that the Probe wave-form is similar to the Irrelevant.

In addition to the data for the parietal (Pz) electrode site illustrated in FIGS. 2 and 3, we recorded data from the midline frontal (Fz) and central (Cz) sites. Subjects exhibited the usual parieto-central scalp distribution for the P300 in those conditions where a P300 was present (i.e., in response to target stimuli in both the "innocent" and "guilty" conditions and to probe stimuli in the "guilty" condition). In most subjects, P300s showed maximum amplitude at Pz, with a simultaneous smaller positive deflection at Cz and a still smaller one at Fz. Three out of 20 subjects exhibited a Cz-maximal P300, with a slightly smaller positive deflection at Pz than at Cz. Such a distribution across subjects of P300 scalp distributions is typical (Fabiani, Gratton, Karis, & Donchin, 1987).

We performed the bootstrapping procedure using data from all three electrode sites in order to see whether or not the additional information provided by scalp distribution could contribute to increased accuracy of determinations of "innocence" or "guilt." We found that, due to greater variability in P300 amplitude and shape at Fz and Cz than at Pz, including these additional channels in our bootstrapping analysis did not improve our ability to make accurate determinations. Collecting and visually inspecting the Fz and Cz data, however, did serve a useful purpose: finding a scalp distribution typical of P300 made it more clear that the component we quantified at Pz was indeed the P300. Although it is clear that the P300 was the major contributor, it is possible that some of the discriminating power was contributed by components other than the P300. From the practical viewpoint this is not an issue. As long as the system yields a correct decision regarding the subject's standing, the percent of the discriminating power contributed by different components is not a major issue with respect to the effectiveness of the technique.

Overt Response Measures

Mean button-press response times for all trials (including EOG-contaminated trials) for each subject in each condition are presented in Table 3.

Table 3. Manual response times, Experiment 1. Mean response times to the probe, irrelevant, and target stimuli for each subject in each condition. Probe response times tend to be slower than irrelevant response times in the guilty condition, and not in the innocent condition. Also, when a given subject is guilty, the button presses in response to target stimuli tend to be slower than when the same subject is innocent. However, as mentioned above, since the timing of manual responses may be easily manipulated, it may not be suitable as a measure of the presence of concealed information (this is discussed in detail in the Discussion section of Experiment 3).

Discussion

The results confirm our prediction that the P300 can be used to identify those subjects who were familiar with the tested scenario. Inspection of the averages obtained from each subject indicates that the predicted pattern was obtained from virtually all subjects. Yet, it is important to avoid reliance on the gross wave-forms when decisions are made with regard to individuals, decisions that may have serious consequences for the individual. To be defensible, such decisions should take into account the inherent variability of the data. The decision rules established here adopt a conservative approach. It is encouraging to note that in no case did the bootstrapping analysis lead to an erroneous decision. That is, the analysis resulted in neither false positives nor false negatives. The analysis recognized that it did not have adequate information to make a determination in 12.5% of the cases.

For a discussion of the theoretical significance of these results, see the General Discussion below.

This proposed new paradigm in the psychophysiological detection of concealed information must, of course, be tested in real-life situations as well as mock laboratory scenarios. Experiment 2 is the first step in this direction. Experiment 2 offers a test conducted in an admittedly non-stressful setting, which did, nevertheless, detect information about real-life transgressions of which subjects were definitely guilty. This data set is also of interest because it examines the efficacy of the brain-wave information detection system in circumstances in which the concealed knowledge derives from incidents that occurred at intervals ranging from weeks to months before the P300 test was conducted. While it is true that the subjects' memory of the incidents was refreshed by the discussion of the incidents in the course of recruitment and structuring of the stimulus sets, the results do extend the scope of this research.

Experiment 2

Introduction

The results of Experiment 1 clearly show the effectiveness of this new paradigm in detecting guilty knowledge regarding a mock crime. The purpose of Experiment 2 was to examine the feasibility of the system in detecting knowledge regarding actual crimes, which were not committed as a part of a laboratory study and which may have taken place a considerable time prior to the testing situation. (Experiment 2 was, in fact, our initial attempt to validate the brain-wave information detection method described in this paper. It was the success of our procedure in the context of Experiment 2 that led to our undertaking the large scale validation project described here as Experiment 1.) We tested four undergraduates who admitted having participated in minor crimes or socially undesirable activities (e.g., being arrested for underage drinking).

Subjects

Four undergraduate students served as subjects. The students were recruited by our advertising (through word of mouth) for subjects who had committed minor crimes or transgressions. The subjects between them were responsible for four transgressions, each being admittedly guilty of one and innocent of the other three.

Procedure

The experimental design was essentially the same as for Experiment 1, except for the modifications described below. The stimuli were presented visually. Each stimulus was a two-word phrase ranging from two to six syllables total. The probe stimuli were items relevant to the crime in question (e.g., the place where the crime took place or the name of another person involved). For each of the six probe stimuli there were one target and four irrelevant stimuli, as in Experiment 1. The target and irrelevant stimuli corresponding to each of the probe stimuli were items of the same type (e.g., a location where the crime did not take place, a fictitious name). Thus, the probe and irrelevant items were indistinguishable except to the guilty person. There was, of course, no training session or mock crime, since the test focused on an actual crime that had already taken place. Instead of pressing a button in response to target items as in Experiment 1, subjects were instructed to count the target items and to ignore the probe and irrelevant items. (Note that this counting task may not be as effective as the button-press task used in Experiment 1 and Experiment 3 for assuring that subjects actually attend to and classify each stimulus. The button press was an innovation that was introduced after these data had been collected see Farwell & Donchin, 1986, 1988, 1989, 1991) Subjects were asked for their tally at the end of each block of trials. The target items were displayed at the bottom of the video screen throughout each block of the testing session as a memory aid.

Each subject was tested on his or her own crime ("guilty" condition), and also on another crime about which he or she knew nothing ("innocent" condition). The stimuli for the "innocent" condition for each subject consisted of the stimuli relevant to another subject's crime.

Results

Figure 6:
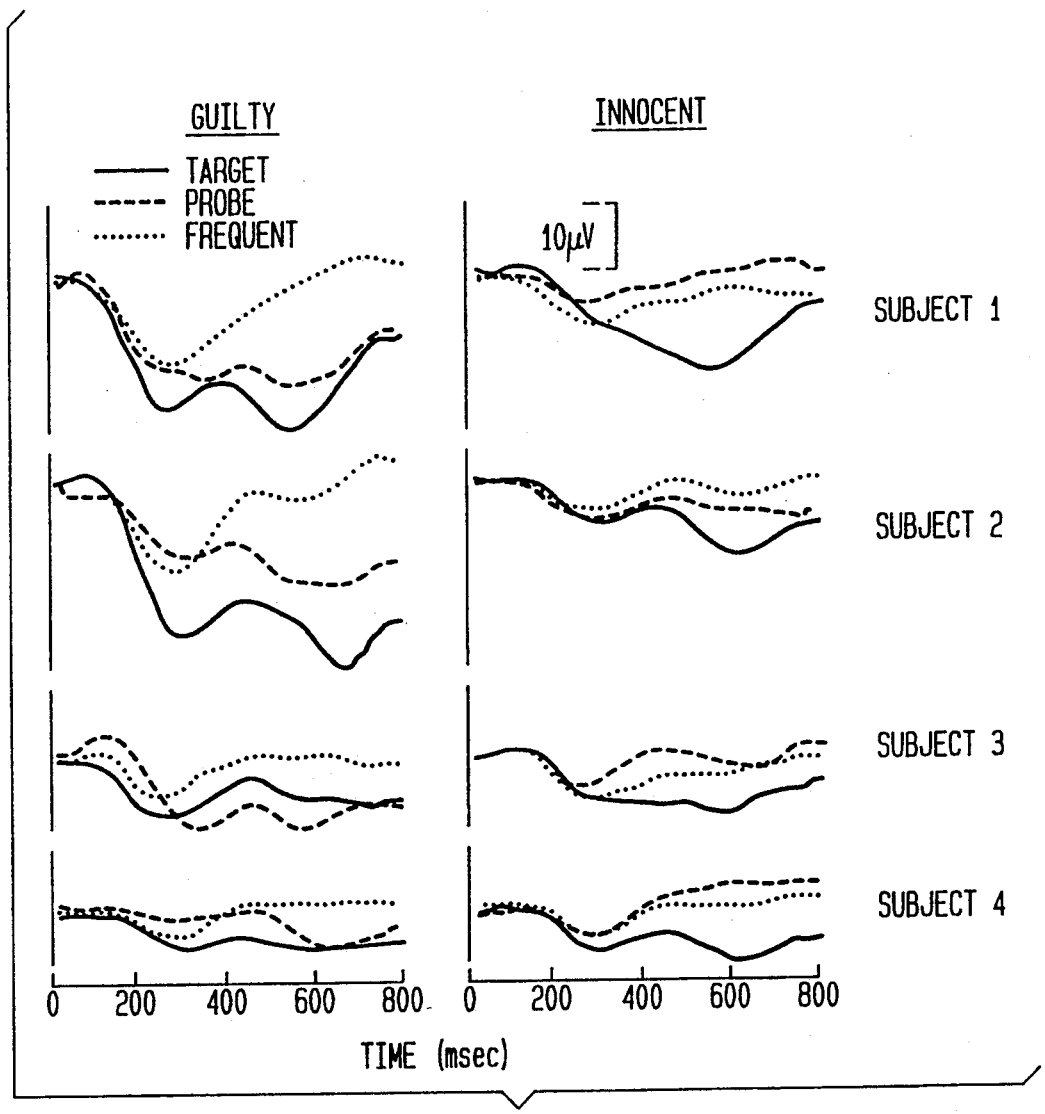
FIG. 6 illustrates ERP waveforms for 4 subjects in the "innocent" and "guilty" conditions (Experiment 2).

The ERP wave-forms for each of the four (4) subjects in the "innocent" and "guilty" conditions are presented in FIG. 6 (Experiment 2). Results are as predicted. It can be seen from the figure that there is a large P300 in response to the targets for all subjects in both conditions, and a very small P300, if any, in response to the irrelevants. In the "guilty" condition, all subjects show a P300 to the probe stimuli similar to their P300 to the targets. In the "innocent" condition the probe responses are similar to the irrelevants, and do not contain a large P300.

As in Experiment 1, we employed bootstrapping to quantify the differences that can be seen in FIG. 6. The results are displayed in Table 4.

Table 4A: Accuracy of determinations, Experiment 2. In the 87.5% of the cases where a determination was made, 100% of the determinations were accurate. Positive and negative predictive values reflect the probability that guilty and innocent subjects, respectively, will be correctly deter-mined, when a determination is made (i.e., excluding indeterminates). Validity reflects the overall probability of correctly determining a subject's state.

Decision rule:
Bootstrap statistic $< 0.10 \rightarrow$ Guilty
Bootstrap statistic $> 0.70 \rightarrow$ Innocent
Bootstrap statistic $> = 0.10$ and $= < 0.70 \rightarrow$ Indeterminate Tables 4B & 4C. Determinations :and statistical confidence, Experiment 2. Bootstrap statistic is the proportion of iterations (out of 100) where the correlation between the probe and irrelevant wave-forms at Pz was greater than the correlation between the probe and target wave-forms. Note that a higher value indicates "innocence" and a lower value indicates "guilt."

As in Experiment 1, the brain-wave information detection system proved highly reliable in distinguishing between the presence and the absence of guilty knowledge. The accuracy of determinations was the same in Experiment 2 as in Experiment 1: 100% correct in the cases in which a determination was made, with 12.5% indeterminate. All of the determinations, both "innocent" and "guilty," were made with a very high statistical confidence.

Discussion

The results of Experiment 2 demonstrate that the phenomenon of a P300 in response to implicitly task-relevant but explicitly task-irrelevant information is not restricted to brief time intervals or precisely defined and closely controlled concealed information. These results show that relevance to actual crimes or similar events, at least when these events have been discussed in the context of the experimental situation, is sufficient for the elicitation of a P300 in this experimental design. This finding is further extended in Experiment 3. (For a more detailed discussion and an account of the theoretical significance of these results, see the General Discussion below.)

Experiment 3

In Experiment 1, subjects were exposed to the probe stimuli one day prior to the ERP testing session in order to learn the mock crime. In Experiment 2, subjects were exposed to the probe stimuli during the interview in which the crime in which they had participated was revealed to the experimenter. Here again, they were exposed to the probes within the context of the experiment and within a short time before the test. The purpose of Experiment 3 was to determine if the Farwell Truth Detector would be effective in the absence of such temporally proximal and experiment-related exposure to the probe stimuli. The subjects in Experiment 3, unlike the subjects in the other two experiments, had no more exposure, during the entire experimental procedure, to the probes and the information they contained than they did to the targets and irrelevants.

Experimental Design and Procedure

The experimental design of Experiment 3 was the same as for the other two experiments, except for the following. The experimenter interviewed friends of the subjects, rather than the subjects themselves, to determine the individual events on which each subject would be tested and the related probe items. Thus, the subjects had no prior exposure to the probes. Data were collected on eight cases. Four subjects (one male) were tested in a "guilty" condition regarding actual events in their own lives, and the same four subjects were tested in an "innocent" condition regarding events with which they were not familiar. As before, subjects were university students. Their ages ranged from 19 to 21 years.

Results

Figure 7:
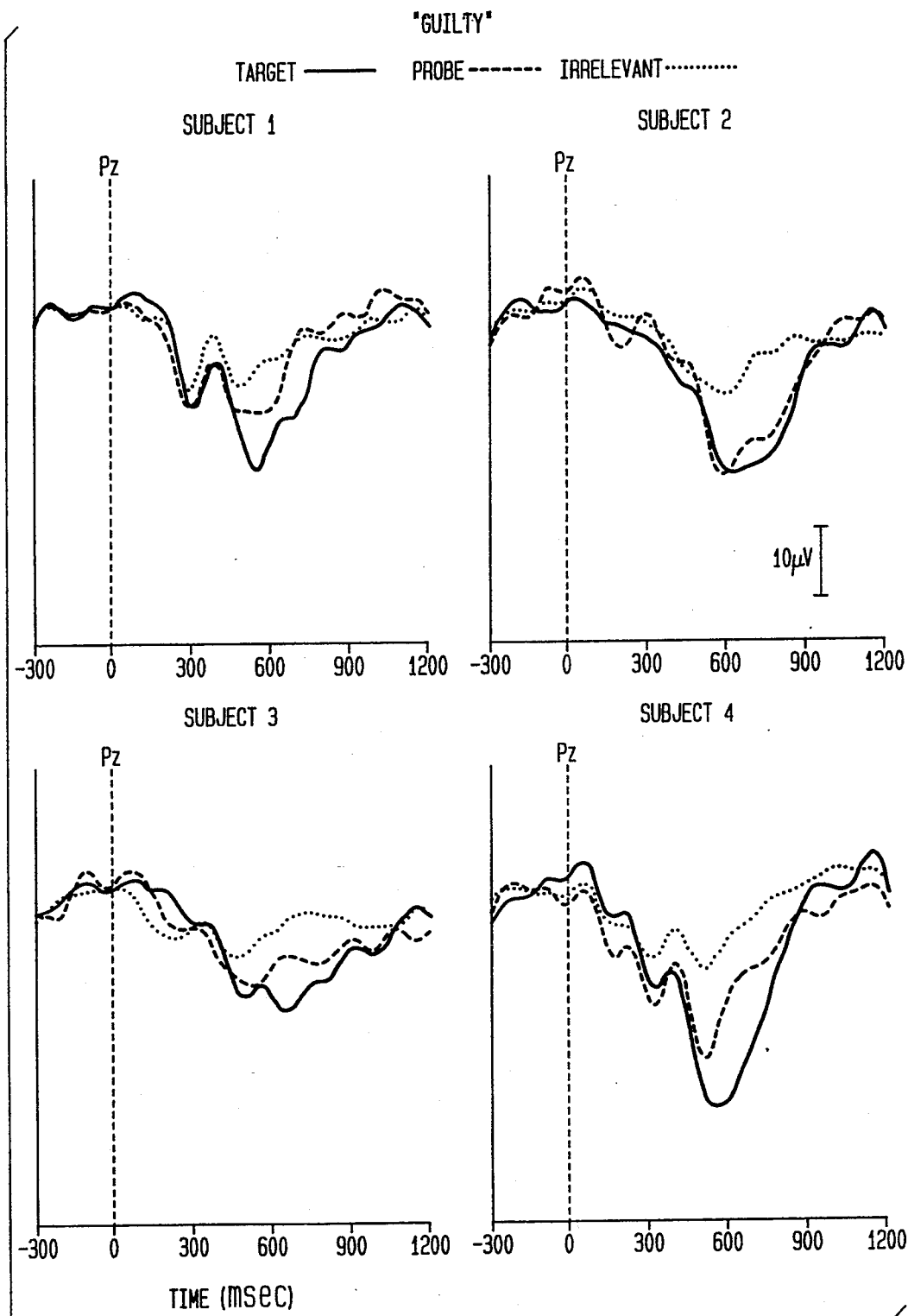
FIG. 7 illustrates ERP waveforms for 4 subjects in the "Guilty" condition (Experiment 3).
Figure 8:
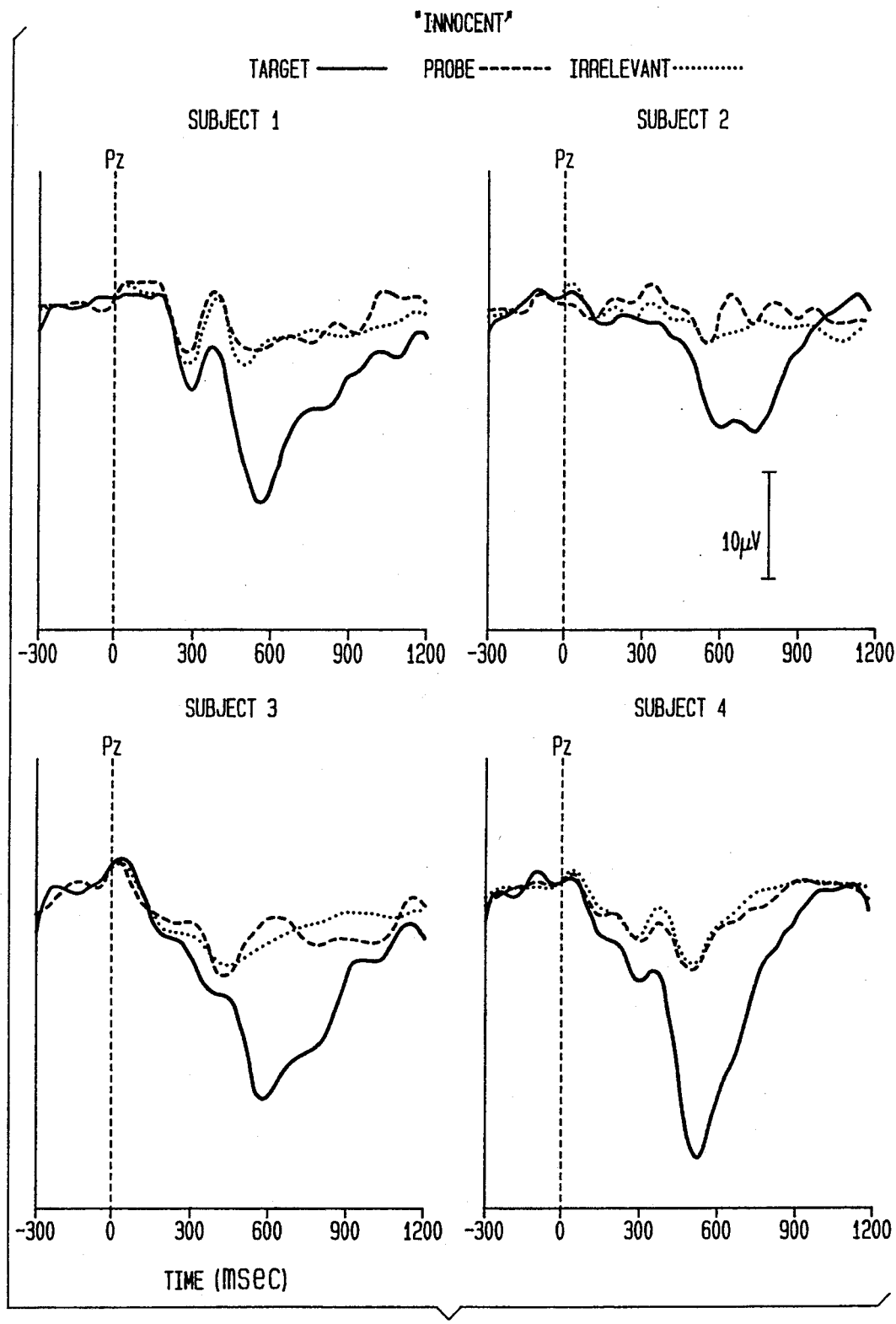
FIG. 8 illustrates ERP waveforms for 4 subjects in the "Innocent" condition (Experiment 3).

The wave-forms for each of the subjects in Experiment 3 in the "guilty" and "innocent" conditions are displayed in FIGS. 7 and 8 respectively. As with the previous experiments, the hypotheses are supported by the data. All subjects in both conditions exhibit large P300s to the targets and not to the irrelevants. In the guilty condition, all subjects exhibit a large P300 to the probes.

As before, data were analyzed using bootstrapping. The results are summarized in Table 5.

Table 5A: Accuracy of determinations, Experiment 3. In the 75% of the cases where a determination was made, 100% of the determinations were accurate. Positive and negative predictive values reflect the probability that guilty and innocent subjects, respectively, will be correctly deter-mined, when a determination is made (i.e., excluding indeterminates). Validity reflects the overall probability of correctly determining a subject's state.

Decision rule:
Bootstrap statistic<0.10→Guilty
Bootstrap statistic>0.70→Innocent
Bootstrap statistic>=0.10 and=<0.70→Indeterminate Tables 5B & 5C. Determinations and statistical confidence, Experiment 3. Bootstrap statistic is the proportion of iterations (out of 100) where the correlation between the probe and irrelevant wave-forms at Pz was greater than the correlation between the probe and target wave-forms. Note that a higher value indicates "innocence" and a lower value indicates "guilt."

As in Experiments 1 and 2, there are no false negatives and no false positives. All subjects in the guilty condition are clustered at the low end of the bootstrap criterion spectrum, and all innocents are clustered at the high end. However, I have chosen to use a very conservative criterion for a guilty determination (bootstrap index of less than 0.10), resulting in two guilty subjects being classified as indeterminate. With this stringent criterion, innocent or guilty determinations can be made in 75% of the cases; 100% of these determinations, as in previous experiments, are correct.

Note that the 25% indeterminate figure could be reduced to 0% by utilizing a somewhat less stringent guilty criterion, e.g., a bootstrap index of 0.20. Since the lowest ground truth innocent subject's score in this study is 0.78, a guilty criterion of 0.20 would not come close to any risk of false positives. (The 0.20 criterion also would have avoided any false positives in Experiments 1 and 2, albeit by a lesser margin.) The conservative 0.10 bootstrap criterion, however, has been retained in an effort to set a precedent of caution in reaching a guilty determination.

Button-press response times are listed in Table 6.

Table 6. Manual response times, Experiment 3. Mean response times to the probe, irrelevant, and target stimuli for each subject in each condition.

In most cases, subjects were considerably slower to respond to probes than to irrelevants when they were guilty and not when they were innocent. Subject 2, however, was 50 msec slower to respond to probes than to irrelevants when he/she was innocent, and only 24 msec slower when he/she was guilty.

Discussion

Brain Responses

Experiments 1 and 2 demonstrated that an explicitly task-irrelevant stimulus can elicit a P300 if it is particularly relevant to the subject's experience and it is given particular significance within the context of the events surrounding the test session.

Experiment 3 is designed to test whether or not a P300 can be elicited by an item solely on the basis of its relevance to a prior experience of the subject, without the stimulus and its significance being in any way emphasized during any of the events surrounding the ERP test. In Experiment 3, throughout not only the ERP testing session proper but all aspects of the experimental procedure and surrounding events, the probe stimuli (and any events to which they are relevant) are treated in no way differently from the irrelevant stimuli.

As mentioned previously, extensive prior research has identified explicit task relevance as an important factor in the elicitation of the P300. The results of Experiment 3 unequivocally identify relevance to the subject's prior experience, entirely independent of the test and surrounding circumstances, as a sufficient condition (on the task relevance dimension) for the elicitation of the P300.

The comprehensive delineation of all of the factors controlling implicit task relevance will be a subject for future research. This series of studies is sufficient, however, to demonstrate that implicit task relevance, combined with rarity but in the absence of explicit task relevance, can elicit a P300. Experiment 3 also demonstrated the effectiveness of the Farwell Truth Detector in detecting real-life events considerably separated in time and context from the detection session. Although this successful demonstration is still not a field application of the system in the detection of concealed information regarding actual crimes, it more closely approaches that realm than the two previous experiments.

Manual Responses

As discussed with regard to Experiment 1, the finding of slower manual performance in response to probes is not a robust phenomenon. In this experiment three out of four subjects exhibited markedly slower responses to probes than to irrelevants when guilty but not when innocent; one subject exhibited markedly slower responses to probes than to irrelevants when innocent, and not when guilty.

Thus, in the two experiments where manual responses were recorded, different patterns of responses were, in general, characteristic of innocent and guilty subjects. Although there were exceptions to the rule, generally guilty subjects' responses to probes were slower than their responses to irrelevant stimuli, and innocent subjects' responses to probes were not slower than their responses to irrelevants. This raises the question of whether manual responses, instead of brain responses, could be used effectively to detect concealed information. The former, of course, are much easier to measure.

One might suspect, however, that subjects could easily eliminate the relative delay in probe manual responses by a simple shift in strategy, but could not easily eliminate the pattern of P300 responses characteristic of an individual who possesses the relevant knowledge sought by the test. This was tested in a pilot study with four subjects. They were instructed to make sure that their manual responses to probe items (that is, items that they recognized as relevant to the investigation but had been instructed to treat in responding like irrelevant stimuli) were not slower than their manual responses to irrelevant items, and their P300 responses to probes were not larger than their P300 responses to irrelevant items. This one sentence change in the instructions to subjects was effective in every case in eliminating the delay in probe responses relative to irrelevants (for guilty subjects). There was no effect on the pattern of P300 responses, even for subjects who had extensive knowledge regarding the theory and antecedent conditions of the P300. It appears, therefore, that at least in this paradigm, manual response times are not a robust means of detecting concealed information.

GENERAL DISCUSSION

Brief Summary of Results

A new system for the psychophysiological detection of concealed information was tested on innocent and guilty subjects who were concealing three different kinds of information: information regarding a mock crime committed as a part of the experiment; information regarding a real, minor transgression committed prior to the experiment but discussed in the course of the experiment prior to the test; and information regarding real-life events that took place a considerable time prior to the experiment and were not discussed prior to the test (the information for structuring the test having been obtained from friends of the subjects). In all three experiments the results were essentially the same: 100% of the determinations made were correct. There were no false negatives, no false positives, and, overall, 14% indeterminate.

Theoretical Significance for Interrogative Polygraphy

Comparison of the Old and New Paradigms

Previous attempts to detect concealed information, dating back for thousands of years, have been founded in an emotional/physiological arousal paradigm. The premise has been that a higher level of emotional, and, consequently, physiological arousal will arise in a deceptive than in a truthful individual. This research introduces a new information-processing brain activity paradigm for the psychophysiological detection of concealed information. The Farwell Truth Detector founded in this new paradigm detects information—which may constitute concealed information—on the basis of the electrophysiological manifestations of information-processing brain activity.

Because of its foundation in brain information processing rather than emotional responses, the Farwell Truth Detector is able to incorporate safeguards against some of the pitfalls of conventional interrogative polygraphy techniques. In this new system, the crime-relevant probe stimuli are indistinguishable from the irrelevant stimuli for an innocent subject, who lacks detailed knowledge of the situation being investigated. This minimizes false positives, which are the most difficult problem for the conventional control question test. The Farwell Truth Detector also employs a control stimulus known as a target stimulus, which provides an information-processing (as opposed to an emotional) control. This minimizes false negatives, the most difficult problem for the conventional guilty knowledge test.

The Farwell Truth Detector also eliminates subjective judgments in the interpretation of results. The brain-wave responses to the crime-relevant probe stimuli are compared to responses to the target and irrelevant stimuli through a mathematical algorithm that computes a determination of "innocent" or "guilty" and a statistical confidence for that determination.

For a detailed comparison of this new paradigm with the conventional paradigm, see the above sections on "Theory in Conventional Interrogative Polygraphy," "The Autonomic Nervous System in Interrogative Polygraphy," and "Advantages of the Farwell Truth Detector over Conventional Techniques."

Conclusion

The results reported here suggest that this new system shows promise as a means of detecting concealed information. Similar results that have been obtained in other studies undertaken since some of the results reported here were originally reported (Rosenfeld, Nasman, Whalen, Cantwell, & Mazzeri, 1987; Rosenfeld, Angell, Johnson & Qian, 1991) support this conclusion. These results call for additional research, particularly in the application of the new system to the detection of actual criminal activity.

Implications for Theories Regarding ERPs

Competing Theories of the Functional Significance of the P300

The previous sections entitled "The Context Updating Model and the Farwell Truth Detector,""Hypotheses of the Functional Significance of the P300," and "Hypotheses and Theoretical Significance of this Research" described in detail the theory on which this research is founded, the predictions made by this theory as to the results of these experiments, and the different predictions of alternative theories. All that remains is to note that the results were as predicted by the context updating model of the functional significance of the P300. The results also support the notion that explicit task relevance is not necessary for the elicitation of the P300: implicit task relevance is sufficient.

The context updating theory of the P300 predicted that a guilty subject, upon taking special note of the probe stimuli as a result of their relevance to his crime, will update his/her internal representation of the current environment. This context updating will be manifested on the scalp in a P300 component of the event-related brain potential. This prediction was borne out thoroughly by the data: almost all of the guilty, and none of the innocent, oases resulted in large P300s in response to probe stimuli.

The brain deactivation theory made the opposite prediction. This theory holds that the P300 is a result of a transient deactivation of portions of the brain upon relaxation of the activity in which the subject has been engaged while anticipating the stimuli. It is held to be accompanied by subjective feelings of relaxation. When a crime-relevant stimulus appears, a guilty subject is experiencing the opposite of relaxation: a heightened state of activation is indicated. According to the brain deactivation theory of the P300, this activation should result in the opposite of a P300, i.e., a cortical negativity. Since the subjects in fact displayed large P300s in response to probe stimuli, the results of these experiments are incompatible with the brain deactivation theory of the P300.

The significance of this research for theories regarding the functional significance of the P300 is that it supports the context updating theory and provides definitive evidence contrary to the brain deactivation theory. More generally, it supports the notion, of which the context updating theory is one instance, that slow event-related brain potentials are manifestations of specific information-processing functions of the brain. It does not support the contrary notion, exemplified by the brain deactivation theory of the P300, that slow event- related brain potentials do not index specific information-processing activities, but are simply indications of the general state of activation of the brain.

Is Concealment Necessary?

The focus of applied psychophysiological detection of information, particularly in the law enforcement realm, has been on information that the subject is attempting to conceal. In the present studies, the subjects were instructed to behave as if they were innocent, that is, to conceal any guilty knowledge that they possessed. It is possible that this attempt to conceal contributed to the salience of the probe stimuli, and thus resulted in a more substantial updating of the schema upon their occurrence and to the larger P300s they elicited. However, in subsequent unpublished pilot studies, similar results have been obtained when subjects were told simply to carry out the instructions regarding button presses, and not told to attempt to conceal any information. In the light of this, it is reasonable to conclude that concealment is not a necessary ingredient in the present system. This is an information detection system, not a concealed information detection system.

Memory and Behavior

Previously, studies of the storage of information in the human brain have been restricted to information that is revealed through self report, task performance, or other overt behavior. Introspectively, it seems very clear that we do store information that is not so revealed. We do seem to have the capacity to remember things that are not revealed by any overt act. This phenomenon, however, has remained outside the realm of scientific scrutiny. The present experiments provide a technique whereby certain information stored in the brain can be revealed without the necessity for overt behavior. This technique may prove useful in a variety of circumstances where for one reason or another overt evidence of information remembered may be unavailable or unreliable.

For example, a number of studies mentioned previously (e.g., Taylor & Kopelman, 1984) indicated that it is not uncommon for perpetrators of major, violent crimes to experience a profound amnesia regarding the event. Such individuals also undoubtedly have considerable motivation to deny any memory of such an event, even if they do remember it clearly. The technique reported here may make possible the discrimination between actual and feigned amnesia in such cases.

Future Research

Experiment 1 demonstrated that probe stimuli that are sufficiently well learned and involved in activities undertaken in the context of an experiment can evoke a P300 even when they are not explicitly task relevant. This does not necessarily imply that probes based on actual life events that have taken place outside the context of the experiment and are considerably separated in time from the testing session will have the same effect. The latter, of course, is necessary if this new technique is to be effective in practice as a method of psychophysiological detection of concealed information regarding criminal activities and the like. In any investigation of real-life events, particularly events that have taken place months or years ago, many factors necessarily remain uncontrolled, and other factors are difficult to bring under experimental control. Experiments 2 and 3 introduced two levels of realism beyond that achieved by Experiment 1. In Experiment 2, the events that gave rise to the probe stimuli were real-life events that had taken place months or years previously. However, these events were discussed by the subjects in the experimental context on the day prior to their testing. Thus, the previous occurrence of the original event was confounded with recent discussion of it in the context of the experiment. The success of the technique in Experiment 2 demonstrated that significant real-life events might be effective in eliciting P300s to probe stimuli, but did not eliminate the possibility that the elicitation of the P300 (and the context updating process it implies) were the result at least in part of the discussions of the previous day rather than the original occurrence of the event. Experiment 2, then, though it introduced a level of realism not achieved in Experiment 1, did not demonstrate that this technique could be effective in actual practice when the subject did not confess to the event prior to testing. Experiment 3 was designed to address this shortcoming by eliminating any discussion of the events in question at the time of or in the context of the experiment. In Experiment 3, all information for the construction of the probe stimulus set was gleaned not from the subject but from other individuals familiar with the subject's past activities. Thus, the situation was similar to the situation faced in an actual investigation of a crime or other real-life event. Experiment 3 demonstrated that the presence of information stored in the brain regarding an actual event can be sufficient to elicit the P300 process upon presentation of a probe relevant to that event. In terms of the context updating theory, context updating can be elicited by a stimulus relevant to a significant life event: the stimulus elicits recall of the event in question, thus constituting a significant event demanding an updating of the schema.

Many aspects of the situation still remain to be brought under experimental control. Future research should systematically investigate the contribution of the factors known to influence autobiographical to this phenomenon. The Human Brain Research Laboratory is engaged in an ongoing program of research that has been designed to achieve this goal. (For a more detailed description of several of the initial studies undertaken, see the subsequent section entitled The Ongoing Research Program.) The following are factors that could be manipulated in future studies.

1) Recency. P300 responses to probes relevant to more recent events could be compared with responses to probes relevant to more distant events. The prediction would be that recent events would be more effective in eliciting a P300, since they would be more effective in eliciting recall of an autobiographical memory.

2) Rehearsal. Events that had been often rehearsed by subsequent recollection (i.e., events that a subject had often discussed with the informant or had to others written about) could be compared with events that had not had such a high level of rehearsal. Probes relevant to more often rehearsed events are predicted to elicit larger P300s.

3) Consequentiality. P300 responses to probes relevant to more vs. less consequential events could be compared. More consequential events are predicted to elicit a larger P300. Consequentiality could be defined in terms of subjects' subsequent ratings of the events.

4) Uniqueness. Responses to probes relevant to unique vs. common events could be compared. The prediction is that probes relevant to unique events would be more effective.

5) Self-reference. Probes relevant to the subject him-/herself could be compared with probes relevant to the same events but not self-referential. The self-referential probes are predicted to be more effective.

6) Reference to actors, actions, locations, and temporal information. It is predicted that probes relevant to actors and actions should be most effective, probes relevant to locations should also be effective, and probes relevant to temporal information should be much less effective.

7) Emotional involvement. Probes relevant to events with varying levels of emotional involvement can be compared. Probes relevant to events with very low emotional involvement are predicted to be less effective than probes relevant to events of moderate emotional involvement. Probes relevant to events of very high negative emotional involvement present an interesting situation. Perhaps, in some circumstances for some subjects, the not altogether uncommon amnesia for events of extreme stress will result in an attenuation of P300 amplitude in response to probes relevant to such events; in other circumstances or for other subjects, probes relevant to such events might be extremely effective in eliciting recall of the autobiographical event and the concomitant context updating and P300. One interesting subject for future research could be congruence (or lack of same) between P300 responses on the one hand and conscious recollection vs. amnesia on the other hand, in the case of events involving extreme stress.

Several other extensions of this experimental program can be envisioned. Perhaps the most important is to test the Farwell Truth Detector in actual field applications involving alleged criminal activity. As mentioned above, in field applications many variables remain outside of experimental control, and the experiences of the humans involved and concomitant brainwave patterns may be different from those found in the laboratory. Since the phenomenon that is manifested in P300 is held to be a cognitive process, rather than an emotional state, it is unlikely that the different emotions encountered in field applications will interfere with the process or with the successful application of the Farwell Truth Detector. However, this remains an empirical question. (This is further discussed in the section on The Ongoing Research Program.)

The experimental program described here demonstrated that the Farwell Truth Detector can be effective in detecting concealed information regarding specific situations. Another possibility would be to use the Farwell Truth Detector to detect a more generalized kind of information or knowledge, such as the knowledge that would be possessed only by military experts or intelligence experts. A stimulus set could be devised including probe items that are well known within a particular profession, but are unknown to the general public. Targets and irrelevants could be phrases that sound similar to the uninitiated, but are not meaningful to those knowledgeable about the field in question. Such a system might prove useful, for example, in identifying individuals who are concealing their identity as intelligence agents. (This is further discussed in the section on The Ongoing Research Program.)

The generalized information may be uncovered using a method of detecting concealed information stored in a human brain of a subject, which information is not regarding any particular event but rather is indicative of a class including affiliation with a particular group of people, familiarity with a particular realm of knowledge, or expertise in a particular field, The method comprises:

a) Presenting to the subject in oddball series stimuli relevant and irrelevant to the class, and Target stimuli requiring the subject to perform a task;

b) Recording electrical brain activity subsequent to the presentation of each of the stimuli for determining corresponding event related brain potential responses; and c) Comparing the responses to the relevant and Target stimuli, and to the relevant and irrelevant stimuli for determining knowledge or lack of knowledge, respectively, of the relevant stimuli in the subject.

The present Farwell Truth Detector has used visual, verbal stimuli. Pictorial stimuli might prove to be a valuable addition in some circumstances. For example, a picture of a victim or accomplice would contain far more information than could be contained in a short phrase, and may prove to be more effective in eliciting a P300 than verbal stimuli. (This is further discussed in the section on The Ongoing Research Program.)

Verbal stimuli could be presented through the auditory modality, instead of visually, Although this would make time locking to the stimulus more problematic, it might capture the attention more readily and thus result in a better response. It would also allow the Farwell Truth Detector to be used on people who are not literate. Simultaneous visual and auditory stimuli might also prove to be useful.

In the present application, the experimenter knew which stimuli were relevant to the situation under investigation. In some cases, one does not know which of several options is relevant. For example, one may have information that a certain terrorist group plans to plant a bomb on an airplane, but may not know which flight has been targeted. The Farwell Truth Detector could be modified to suit such a circumstance. The possible options would be presented along with a target that was identified as such in instructions to subjects. Analysis would compare each of the options with the other options (and with the target), to determine if a large P300 was elicited by one of the options. If so, this would indicate that that option was significant to the subject, and may be the answer sought. (This is similar to a searching peak of tension test in conventional polygraphy.)

The applications of such an extension of the Farwell Truth Detector might be quite broad, covering virtually any information that could be presented as a multiple choice test. Since some college students complete their higher education with the majority of the knowledge gained throughout their college career having been tested on computer scored, multiple choice tests, such a modified version of the Farwell Truth Detector might potentially have very far-reaching applicability.

In summary, the three experiments reported here demonstrate that electrical brain activity manifesting information processing in the brain can be effectively used in detecting concealed information. This finding introduces a new brain information processing paradigm in psychophysiological detection of concealed information. Such a development calls for extensive additional research to investigate and elucidate the nature and range of applicability of this phenomenon, and the laws of nature that give rise to it.

THE ONGOING RESEARCH PROGRAM

The Human Brain Research Laboratory is currently conducting a series of experiments to further develop the new paradigm introduced in the previous sections. The following is a brief description of the ongoing research. This account will be updated from time to time as results are obtained.

Experiment A: Major Crime Study

The following study is currently being undertaken by the Human Brain Research Laboratory independently. Collaborations with other laboratories and agencies are also under negotiation.

Using the Farwell Truth Detector system described above, Human Brain Research Laboratory shall conduct tests on twenty (20) incarcerated male perpetrators of major crimes. Information regarding the crimes shall be obtained from law enforcement authorities. This information shall be used to construct stimuli to test whether the subjects are guilty of their own crimes and of other crimes about which they have no knowledge. Each subject shall be tested in both the guilty and innocent conditions and classified as guilty or innocent in both conditions. A statistical confidence for each determination shall be computed.

The tests shall be administered by an individual who is blind to the true conditions of the subjects. Subjects shall not be informed of their individual performances, and subject identification data shall be dissociated from specific outcome data after data collection. Results shall be reported either as aggregate data or associated with subject codes, from which subject identities can not be determined.

The experimental design is based on the original research described in previous sections. Fundamental to this design is the "oddball" experimental procedure. In this procedure, a series of stimulus events are presented to a subject. Some of the events (the "oddballs") are relatively rare, and in response to these events the subject is required to perform a task. Extensive research, reviewed in previous sections, has shown that these rare, task-relevant stimuli elicit an event-related brain potential characterized by a P300 component. The P300 is an electrically positive component, maximal at the midline parietal scalp, with a latency in excess of 300 msec. It can be readily recognized through signal averaging procedures, as described above.

In the proposed experiment, visual stimuli consisting of short phrases will be presented on a video screen under computer control. As usual in Farwell Truth Detector tests, three categories of stimuli will be presented: "probes," "targets," and "irrelevants." Probes are stimuli relevant to the crime under investigation. Irrelevants are, as the name implies, irrelevant. For each probe stimulus, there will be approximately four irrelevant stimuli. The stimuli will be structured such that the probes and irrelevants will be indistinguishable for an innocent subject. That is, if a given probe is an article of clothing relevant to the crime, four articles of clothing irrelevant to the crime will also be presented; if a particular probe stimulus is a name, there will be four irrelevant stimuli that are also names, and so on.

In addition to the probes and the irrelevants, a third type of stimuli, designated as targets, will be presented. About one-sixth of the stimuli are targets. The subject is given a list of the targets, and is required to press a particular button whenever a target is presented. (For all other stimuli, the subject is instructed to press another button.) Thus, the targets constitute a rare (probability of 0.17) and task-relevant (button press) stimulus, and therefore will elicit a P300 component in the brain response.

For an innocent subject, then, this is simply an ordinary oddball task. He recognizes only two types of stimuli: rare, relevant targets and frequent, irrelevant stimuli (consisting in fact of true irrelevants, plus probes—which he does not distinguish as being different from the irrelevants). The targets elicit a P300, and the irrelevants and (unrecognized) probes do not. A guilty subject, however, recognizes a second rare, relevant type of stimuli, namely the probes, which are relevant to a crime or other situation in which he has participated. Thus, for a guilty subject, the probes, too, elicit a P300.

What this experimental design accomplishes, essentially, is to create one oddball series for an innocent individual, and two oddball series (with the same stimuli) for a guilty individual. The targets provide a template for stimuli known to be rare and relevant—P300-producing stimuli. The irrelevants provide a template for a response to stimuli that are frequent and irrelevant—non-P300-producing stimuli.

The determination of guilt or innocence consists of comparing the probe responses to the target responses, which contain a P300, and to the irrelevant responses, which do not. If the probe responses are similar to the target responses, one can conclude that the subject recognizes the probes—which only someone knowledgeable about the crime would do—and therefore is "guilty" (or, more correctly, "knowledgeable"). If the brain responses to the probes are like those to the irrelevants—i.e., lacking a P300—then the subject can be determined to be "innocent." (Note that what is detected is not actually guilt or innocence, but knowledge or lack of knowledge regarding the situation under investigation. In order for this to be an effective indicator of guilt or innocence, stimuli must be structured such that only a guilty person would recognize the probe stimuli.)

As described in the accompanying report, the statistical technique of bootstrapping is employed to compare the brain responses to the different types of stimuli, to make a determination of "innocent" or "guilty," and to provide a statistical confidence for this determination.

The following is a more specific plan for the implementation of this experimental design. Some of the details of implementation of this experiment may be modified in the light of experimental data acquired in the course of the research.

The visual stimuli will be presented with a stimulus duration of 300 msec, at an inter-stimulus interval of 1550 msec. Stimuli will be presented in random order. For each test, there will be six unique probes, six unique targets, and 24 unique irrelevants. In each block of trials, each of these 36 stimuli will be presented four times, for a total of 144 trials. (Trials with data contaminated by artifacts generated by eye movements or other muscle-generated noise will be rejected on-line, and additional trials will be presented so that the required number of 144 artifact-free trials is obtained.) Three blocks of trials will be presented to each subject in the guilty condition (i.e., probe stimuli relevant to the subjects' own crime), and three blocks will be presented to each subject in the innocent condition (probe stimuli relevant to another crime unknown to the subject).

Brain responses will be recorded from the midline frontal, central, and parietal scalp locations (Fz, Cz, and Pz respectively, International 10-20 System) referenced to linked mastoids (behind the ear), and from a location on the forehead to track eye movements. Scalp recording will be done with standard EEG electrodes of the type used over the past several decades for electroencephalography. In the event that a new electrode system now under development under Sponsor funding becomes available, this new system will be employed. This system is designed to increase the convenience of the procedure for subjects. It allows the electrodes to be held in place by an expandable headband, instead of being attached with electrode paste. This minimizes the effect of the procedure on hairstyles, and allows the electrodes to be placed and removed more quickly.

Data will be amplified with standard EEG amplifiers and stored on disk for off-line data analysis. EEG artifact removal and correction procedures, digital filtering, and bootstrapping statistical analysis will be applied to the data off-line. These procedures are described in detail in previous sections. The result of this analysis will be a determination in each case of "innocent" or "guilty," and a statistical confidence for this determination. (:) In this way, we propose to apply in a realistic, field setting the brain-wave based information detection system which has proven to be effective in the laboratory. This experiment will serve to test the effectiveness of this system in detecting actual major crimes.

Volunteers will be solicited in prisons through the prison authorities. From among the volunteers, prisoners will be selected for testing who have committed major crimes for which adequate specific details can be obtained through available case records.

The following principles will be followed in selecting probe stimuli for each crime. The stimuli must be specific to the particular crime, not general in nature, such that they could be the kind of information that would be known only to the criminal and knowledgeable authorities. For example, if the crime were an assault, the words "assault," "beat," etc. would be inappropriate. Appropriate items might include specific details regarding the scene of the crime; the method and specific weapon involved; the appearance of the victim; the circumstances under which the crime took place; in some cases the names of the victim, accomplices, witnesses or other people involved; and other specific details. The stimuli should be as salient as possible. Insofar as possible, they should be items directly involved in the crime itself. For example, if a victim was wearing a green scarf at the time of an assault, this would ordinarily not be an appropriate stimulus; but if the victim's hands were tied using the scarf, it would become a salient item likely to be remembered by the criminal and could be effectively used as a probe stimulus.

The following further steps will be taken to insure confidentiality of the subjects. Each subject will be assigned a number when initially recruited. Throughout the experiment, all data regarding the subject will be associated only with the subject number, and not the name of the subject. The names of the subjects will be used only for the purposes of scheduling the actual meetings with the subjects and obtaining information on the subjects' crimes. Once the information in the case files has been reduced to a set of stimuli, these stimuli, too, will be associated with the subject number rather than with the name. Demographic information kept regarding the subjects and any descriptions of the their crimes in reports or publications will be of a general nature, such that the identity of the subject can not be determined from the information.

Experiment B: Pictorial Stimuli Study

The Human Brain Research Laboratory shall replicate the original brain-wave guilty knowledge study (Experiment 1), substituting pictorial stimuli for verbal stimuli. Twenty (20) subjects (approximately equal proportions male and female) shall be trained using an interactive computer program, then carry out one of two espionage scenarios, and then will be tested using the brain-wave guilty knowledge technique. Subjects shall be categorized as guilty or innocent for each scenario, and a statistical confidence for each determination shall be computed.

The interactive training program that will train the subjects in an espionage scenario will be based on the original interactive training program written by the principal investigator of this proposal and used in the original study, except that instead of verbal items, pictures will be presented. Subjects will be interactively tested on their recognition of the pictures relevant to the mock espionage scenario they must enact. In the previous study, the probe stimuli consisted of short phrases designating distinctive items of clothing (e.g., "green hat"), code names (e.g., "Fred Smith", rendezvous locations (e.g., "Pine Street"), the names of a files containing documents, (e.g., "rain file"), and a type of documentation that was contained in the file (e.g., "sub plans"). The pictorial stimuli will be similar in content, except that they will be pictorially presented, for example, pictures of a green hat, of a person, of a rendezvous location, of the place from where the files in question must be retrieved, and of the items to which the documents pertain (e.g., a submarine).

Subjects will be recruited via advertisements and paid for their participation.

The testing and EEG recording procedures will be the same as in the original study, and the same as that described in Experiment B above, except that the stimuli will consist of pictures rather than words. Data analysis and determinations of innocent or guilty also shall be as described above.

The purpose of this study will be to discover the level of effectiveness in detection of guilty knowledge provided by pictorial stimuli. Pictorial stimuli in some cases have the potential to provide far more information in one glance than can be contained in a short phrase. For example, the picture of a person involved in a crime, or of the scene of the crime, might prove to be a very effective probe stimulus. If pictorial stimuli prove to be effective, this will broaden the applicability of the Farwell Truth Detector technique, and may serve to increase the potential accuracy of the technique as well.

Experiment C: Professional Profiles Study

The Human Brain Research Laboratory shall devise and apply a technique based on the Farwell Truth Detector system that obtains information about an individual subject's occupation. HBRL shall conduct a study to devise and conduct a test to determine whether a given subject is employed by the U.S. Navy. The final test shall involve forty (40) subjects, half of whom are employed by the U.S. Navy. Subjects shall be categorized as employed or not employed by the Navy, and a statistical confidence for each determination shall be computed.

Previous research has shown that the Farwell Truth Detector can be effective in detecting knowledge regarding both mock crimes and real-life events, when specific details of the events in question are known. The goal of this study is to extend the realm of applicability of the procedure to the detection of knowledge not confined to a particular event at a particular time and place. For example, it might be important to know whether or not an individual was or was not a member of a particular foreign intelligence organization (or a subversive group, criminal organization, military organization, or other group of interest), or whether or not an individual possessed particular professional knowledge. One may not know what specific events an individual would have witnessed, but nevertheless there is certain knowledge that is not commonly available that members of a particular organization, group, or profession would have. An affiliated, and therefore knowledgeable, individual would recognize certain technical terms, organizational titles, names of significant people and places, etc., that would mean nothing to a member of the general public. A system that employs such items as probe stimuli, interspersed with target and irrelevant stimuli as in previous studies, may be effective in detecting members of particular organizations or groups, or people with particular kinds of professional knowledge.

The testing, data acquisition, and analysis procedures in this study will be as described for Experiment A, except that the probe stimuli will be relevant to the kinds of knowledge that an employee of the U.S. Navy would be likely to possess.

EXPERIMENT D:
Multiple-option Concealed Knowledge Test
4.3.1. Overview

The contractor shall perform a multiple choice concealed knowledge on 20 subjects. The essential component of this study is to determine if the Farwell Truth Detector can be used to identify guilty knowledge in a situation in which the examiner does not have details of the event under question. Presumably, the examiner is in a position to make an educated guess as to things (events, details of an event, etc.) the subject may know, but will not admit to knowing. A test will be constructed in which the subject is presented multiple stimuli, only a small subset of which are likely to be relevant to him. The challenge of the examination is to determine which subset of the stimuli is relevant to the subject and ensure that the reaction is due to guilty knowledge, and nothing else.

Data analysis for this experiment will go beyond the bootstrap technique used in the original Farwell Truth Detector. Algorithms shall be developed to determine what stimulus is relevant to a given subject compared to the other irrelevant stimuli. Guidance for creating stimuli in different situations shall be established.

4.3.2. The Multiple-option Design

In the tests conducted to date with the Farwell Truth Detector, the experimenter knew that specific stimuli were crime-relevant probes, and the task was to determine whether or not the subject possessed that guilty knowledge. Another situation in which the Farwell Truth Detector could be useful is in a situation where the investigator does not know the answer to a question, but can narrow it down to a few possibilities, and where the subject is suspected to know the answer but is unwilling to reveal it.

For example, one may have evidence that a terrorist group is planning an attack at a major airport on the East Coast, but not know where the attack is to take place. If a series of verbal stimuli are presented, each containing the name of a different airport, then the relevant airport will be a rare and noteworthy stimulus for the subject, and can be expected to elicit a P300 brain response.

The data analysis for such an experiment will be somewhat different than the data analysis for the usual Farwell Truth Detector experiments. The Farwell Truth Detector ordinarily compares known probe (crime-relevant) with known irrelevant and target stimuli (targets are somewhat analogous to control questions in a conventional lie detection test, but provide an information- processing, rather than an emotional, control). In this case, one will not know which stimuli, if any, are relevant, so responses to each stimulus will need to be compared to all of the others to select the correct alternative. One of the major challenges of this experiment will be to develop algorithms implementing this procedure and establish decision criteria.

Two options are available for this experiment: 1) a mock crime study similar to the original study conducted with the Farwell Truth Detector (Experiment 1 in the accompanying technical report); or 2) an investigation of real-life events in the lives of subjects. These options are described below.

4.3.3. Option 1: Mock Espionage Experiment

The stimuli to be used in the mock crime experiment, the training in the mock crime, and the carrying out of the crime itself will be the same as those used in the original study conducted with the Farwell Truth Detector, except that there will be five different mock crimes, and the task will be to determine which, if any, was committed by the subject.

In the original study, subjects were trained by an interactive computer program to perform one of two different mock espionage scenarios, which they then proceeded to enact. Each subject learned one scenario and was unaware of the other scenario. Thus, each subject could be tested on the knowledge of the scenario which he or she experienced (this was that subject's "guilty" scenario) as well as on the scenario of which he was innocent. Each of the scenarios required the subjects to go to a specific location and meet a person with whom a password was exchanged. The subject then asked that person for a file which had a particular designation and which pertained to a specific operation.

Six critical details were associated with each of the two scenarios. Knowledge of these details could be used as indication that the subject participated in the scenario.

The interactive training program consisted of a series of instructions as to the critical items which the subjects were instructed to memorize and actions they were to follow. The instructions were repeated several times, and subjects were repeatedly tested on the instructions until they had responded correctly at least five times to questions regarding each of six key items. Following the training session, when the computer had established that the subjects had learned the scenario to criterion, they were instructed to undertake the mission. In each case, the appropriate file folders were handed to the subject and he/she proceeded to the assignation and exchanged information and files with his/her contact.

After executing the scenario each subject underwent an examination with the Farwell Truth Detector designed to test if the subject possessed "guilty" knowledge. Subjects were tested for knowledge of each of the two scenarios, the one in which they had actually participated and the other scenario of which they knew nothing.

The proposed study will be based on the original study, except that instead of being "guilty" or "innocent" of one crime, there will be five different mock espionage scenarios, involving five different sets of crime-relevant stimuli Each subject will either participate in one of the five mock espionage scenarios, or will not participate in any scenario. The task of the Farwell Truth Detector will be to determine which one of the scenarios, if any, each subject has participated in. Instead of an binary "innocent" or "guilty" determination, there will be six different possible conclusions: the subject's brain has stored knowledge regarding one of the five scenarios, or none of them.

Human Brain Research Laboratory will run 20 subjects in this experiment. Each subject will be randomly assigned to enact one of the five crime scenarios (17% probability of each), or to enact none of the scenarios (17% probability). Stimuli relevant to each of the five scenarios will be presented, along with target stimuli. Subjects will be given a list of the target stimuli prior to the test. Subjects will be instructed to push one button in response to targets, and another button in response to all other stimuli.

The predicted result is that the targets and the stimuli relevant to the one scenario each subject has enacted will elicit a P300, and the stimuli relevant to the four scenarios each subject has not enacted will not elicit a P300. For the subjects who have enacted none of the scenarios, only the targets are predicted to elicit a P300. The data analysis task will be to detect which is the correct information for each subject, or whether none of the scenarios are relevant. Since it is not known which are the probe stimuli in this case, each of the five sets of stimuli (each relevant to one scenario) will have to be compared with the targets and with the other sets of non-targets. HBRL will develop and test an algorithm for making this comparison and drawing a conclusion regarding each subjects participation in the scenario. A number of different metrics for the P300 will be included in the algorithm. These may include peak amplitude, integrated area, correlation, covariance, and other metrics.

4.3.4. Option 2: Real-life Experiment

The second option for the multiple option experiment will be to use actual information regarding each subject's life to structure the stimulus sets. The stimulus presentation, data acquisition, and analysis will be the same as described for the mock espionage option. The only difference lies in the type of information detected.

In the real-life option, the information detected will consist of specifics regarding the individual's life experiences. One set of stimuli containing information from each subject's own life will be presented along with four sets of stimuli, each similar in content but irrelevant to the subject. In one-sixth of the cases, as before, none of the stimuli will be relevant to the subject. As before, target stimuli, which will be identified to the subject in the course of experimental instructions, will also be presented. Subjects will press one button in response to targets, and another button in response to all other stimuli. As before, the prediction is that a P300 will be elicited only by the targets and the stimuli (if any) relevant to each particular subject.

Information for structuring the stimulus sets will be obtained from interviews with subjects prior to testing. No attempt will be made to obtain information regarding actual crimes that may have been committed by the subjects, or to obtain information of a sensitive, private, or potentially embarrassing nature. Informed consent will be obtained in advance. The information obtained from subjects will be nothing more than the kind of information that would often be volunteered in a conversation—for example, their occupation, recreational activities, friends and relatives, place of residence, etc. The information obtained from subjects will be used only to structure stimulus sets, and will be kept confidential.

4.4. Task 2. Advanced Data Analysis

The previous data analysis conducted in the Farwell Truth Detector has utilized one metric to determine the similarities and differences between the event-related potential waveforms, namely bootstrapping performed on double-centered correlations. The results with this one metric have been excellent. However, there is considerable information contained in the data that is not effectively reflected by this particular metric. In cases where a decision may have major human consequences, it will be important to extract as much information as possible from the data.

The advanced data analysis task will develop several different algorithms for analyzing the data and making determinations of subject status, test these algorithms on the data obtained in the three studies conducted under this contract, and refine the algorithms based on these tests.

Different individuals produce data sets with different characteristics, for example, latency, amplitude, and shape of the waveform, amount of latency variability across single trials, relative amplitude of responses to different types of stimuli, etc. Different metrics are optimum for different individual data sets. The optimum data analysis algorithm will probably be a combination of several different metrics, each of which takes advantage of somewhat different characteristics of the data. In addition to testing the relative effectiveness of several different metrics, HBRL will develop and test algorithms that combine different metrics in a systematic manner. Some of the different algorithms that may prove useful in this task are P300 integrated area; P300 base-to-peak amplitude; peak-to-peak amplitude; single-centered correlation; covariance; a comparison of difference scores all of the previous measures; computations based on both single averages and bootstrapped averages for all of the previous measures; latency variability correction (Woody filter); eye movement correction procedure; and digital filtering.

The advanced data analysis task will consist of developing, testing, and comparing these and other metrics and algorithms, reporting on their effectiveness in making determinations on the data obtained in the studies performed for this contract, and making recommendations for future data analysis in the laboratory and in the field.

Technical description:

Farwell Truth Detector ERP "Headband"

The headband apparatus for collection of event-related brain potentials (ERPs) eliminates the need for complicated and uncomfortable structures which are difficult to size to the head on the one hand and for painstaking individual placement of electrodes on the scalp on the other. Combining the location stability of the first with the comfort of the second, the headband forms a superior alternative to both.

Three basic designs, all variations on the headband theme, will be described below. The "headband" apparatus utilized in the measurement of electrical brain activity has the following general features:
a) assured sizing through extreme structural flexibility;
b) assured placement of electrodes by affixing them to a highly flexible super-structure;
c) construction of a comfortable cloth material that stretches easily;
d) disposable electrodes affixed to the headband by snaps;
e) electrode wires running within the headband sheath.

The headband may also have the following specific features:
a) a strap that wraps around the head from the forehead to the back of the head and a second strap that crosses from the front to the back of the head, to position electrodes across the midline of the scalp;
b) construction of a cloth material that stretches easily;
c) fastening of the two ends of the headband and the third end of the cross-scalp strap with Velcro at the back of the head;
d) wires to conduct the brain signals, running inside of the cloth straps to a connector that can be connected to a cable leading to an EEG amplifier;
e) snaps at the desired electrode locations on the headband: Fz, Cz, Pz, forehead ground; forehead eye movement lead; left mastoid, and right mastoid;
f) disposable electrodes affixed to the headband by snaps.

The headband may also have the following features:
a) an additional flap of material attached perpendicularly to the overflap whose ends are to be tucked under the band in two locations;
b) left and right mastoid snap-in electrode sites attached to such a flap.

The headband may also have the following features:
a) Velcro pads attached to the anterior side of the headband at each electrode site;
b) Velcro sizing flaps also attached to the anterior side of the headband, to be positioned on the pads as required.

The headband may also have the following features:
(a) one or more flexible straps of a length sufficient to surround a subject's head,
(b) electrodes removably affixed to the one or more straps, and
(c) electrode wires providing electrical connection of the electrodes to an EEG amplifier, the electrodes having a surface which provides contact to the subject's skin without abrasion or adhesive.

Yet further, the headband may have the following features:
(a) a flexible primary strap that wraps around the head of a subject from the forehead to the back of the head and a flexible secondary strap that crosses from the front to the back of the head and is affixed to the primary strap at one end;
(b) fasteners at both ends of the primary strap and the free end of the secondary strap;
(c) snaps affixed to the primary and secondary straps at the desired electrode locations on the headband, including those positions corresponding to the Fz, Cz, and Pz positions on the head; the left mastoid; and the right mastoid; and
(d) electodes removably affixed to the headband by the Snaps.

The method of measuring electrical brain activity may utilize a headband having the features listed above.

All three headband designs are composed of elastic stretch materials, with Velcro bands acting as fasteners, and seven internally-wired female sides of snap-in electrode sites sewn into the head-touching, or "posterior," side. The electrode wires, grouped and enclosed in the material sheath, terminate in a DB9 female connector. The headband has an upside-down T-shape. The "bar" of the T (or "band") wraps around the head on a plane perpendicular to the ground with the intersection of the overflap and the band (or "crossbar") at the center of the forehead, placing four electrodes on the forehead (EOG and ground) and behind the ears (left and right mastoid), and fastens at the back of the head with Velcro. The "leg" of the T (or "overflap") wraps back up and over the top of the head, placing the other three electrodes on the Fz, Cz, and Pz sites (the International 10-20 System), and fastens to the Velcro hook pad on the left anterior end of the band. The DB9 connector at the top end of the overflap (or "mouth") plugs directly into the amplifiers.

Basic Headband

Referring to FIGS. 9 and 10, the headband 10 includes a flexible band 12 also referred to as a crossbar or strap which has first and second opposite ends 12a, 12b and a center portion 12c therebetween. The band 12 is sized to have a suitable length to wrap around the subject's head for joining together the first and second ends 12a,b, with the right side of the band 12 (which includes the band first end 12a) configured for placement over the right mastoid, and the left side of the band 12 (which includes the band second end 12b) configured for placement over the left mastoid. A flexible overflap 14 also referred to as a strap is integrally joined to the band 12 in a general T-configuration. The overflap 14 includes first and second opposite ends 14a, 14b, with the overlap first end 14a being integrally joined to the band center portion 12c. The overflap 14 is sized for having a length to cross from the front to the back of the subject's head over the scalp frontal, central, and parietal locations for joining together the overflap second end 14b to the joined-together band first and second ends 12a, 12b.

More specifically, first and second means are provided for releasably joining together the band first and second ends 12a, 12b; and the overflap second end 14b with the joined-together band first and second ends 12a,b. In the preferred embodiment illustrated in FIGS. 9 and 10, cooperating Velcro pads or strips are used. (Velcro, according to Webster's New World Dictionary, is a trademark for a nylon material made with both a surface of tiny hooks and a complementary surface of an adhesive pile typically used in garments in matching strips that can be pressed together or pulled apart for easy fastening and unfastening.)

As shown in FIG. 9, the posterior side of the headband 10 includes similar Velcro loop pads 16 illustrated as rectangles with curved corners suitably attached to the respective second ends 12b and 14b of the band 12 and overflap 14, respectively. FIG. 10 illustrates complementary Velcro hook pads 18 suitably attached to the anterior side of the headband 10 at the band first and second ends 12a, 12b. The hook pads 18 are illustrated as rectangles with sharp corners to distinguish them from the loop pads 16. The Velcro loop and hook pads 16, 18 allow the band 12 to be configured around the scalp of the subject and held in place by the cooperation thereof. The overflap 14 extends over the midline of the scalp, with the loop pad 16 on the second end 14b thereof being joined to the hook pad 18 on the second end 12b of the band 12. In this way, the headband 10 may be positioned over the scalp of the subject, with the overflap 14 extending along the scalp midline.

In the embodiment illustrated in FIG. 9, seven female sides of snap-in electrode sites, designated 20a–20g, are suitably spaced apart along the posterior side of the band 12 and the overflap 14 for alignment with the scalp frontal (Fz), central (Cz), parietal (Pz), left mastoid, and right mastoid locations, upon placement or installation of the headband 10 on the subjects's scalp. Respective electrode wires 22 extend from the electrode sites 20 and extend internally through, and are enclosed by, the material sheath defining the band 12 and the overflap 14 arid have proximate ends wired or joined to a DB9 female connector 24 disposed adjacent to the overflap second end 14b.

The female electrode sites 20 are fixedly joined by being sewn to the band 12 and overflap 14 on the posterior, or head-touching, side thereof. The female sites 20 receive electrodes for sensing the electrical responses from the subjects scalp. In order to properly align the electrodes on the scalp, the band center portion 12c is placed at the center of the forehead, with the band 12 being wrapped around the head. The overflap 14 wraps back up and over the top of the head for placing the first three electrode sites 20a, 20b, and 20c at the frontal (Fz), central (Cz), and parietal (Pz) sites, respectively.

The remaining four electrode sites 20d, 20e, 20f, and 20g are disposed along the posterior side of the band 12 for aligning the respective electrodes therein with the left mastoid, electro-oculogram (EOG), ground, and right mastoid sites, respectively.

The basic headband 10 adds no features to the T-shaped apparatus described above. Its approximate optimal dimensions are as follows: The overflap 14 measures 14" mouth to crossbar; the band 12 measures 24.5" end to end and 1.25" across. Both band and overflap are 1.25" wide. The posterior side of the overflap begins with a 3" band of Velcro loops placed 0.5" below the mouth (see FIG. 9). The overflap's three electrodes are placed every 2.75" on the posterior side, starting 2.5" below the Velcro band (with Pz). This leaves 1.75" between the last electrode (Fz) and crossbar. The posterior side of the band, then, starts on the left with a 3.5" pad of Velcro loops, placed 0.25" from its end. 1.5" separate the pad from the first electrode (the left mastoid); 5.5" separate that electrode from the next (EOG/-ground). The electrode placement dimensions are repeated on the other side without a Velcro pad. On the anterior side, a 3.5" pad of Velcro hooks is placed 0.25" from both ends of the band (see FIG. 10). The anterior side of the overflap is featureless.

Mastoid-Flap Headband

Figure 11:
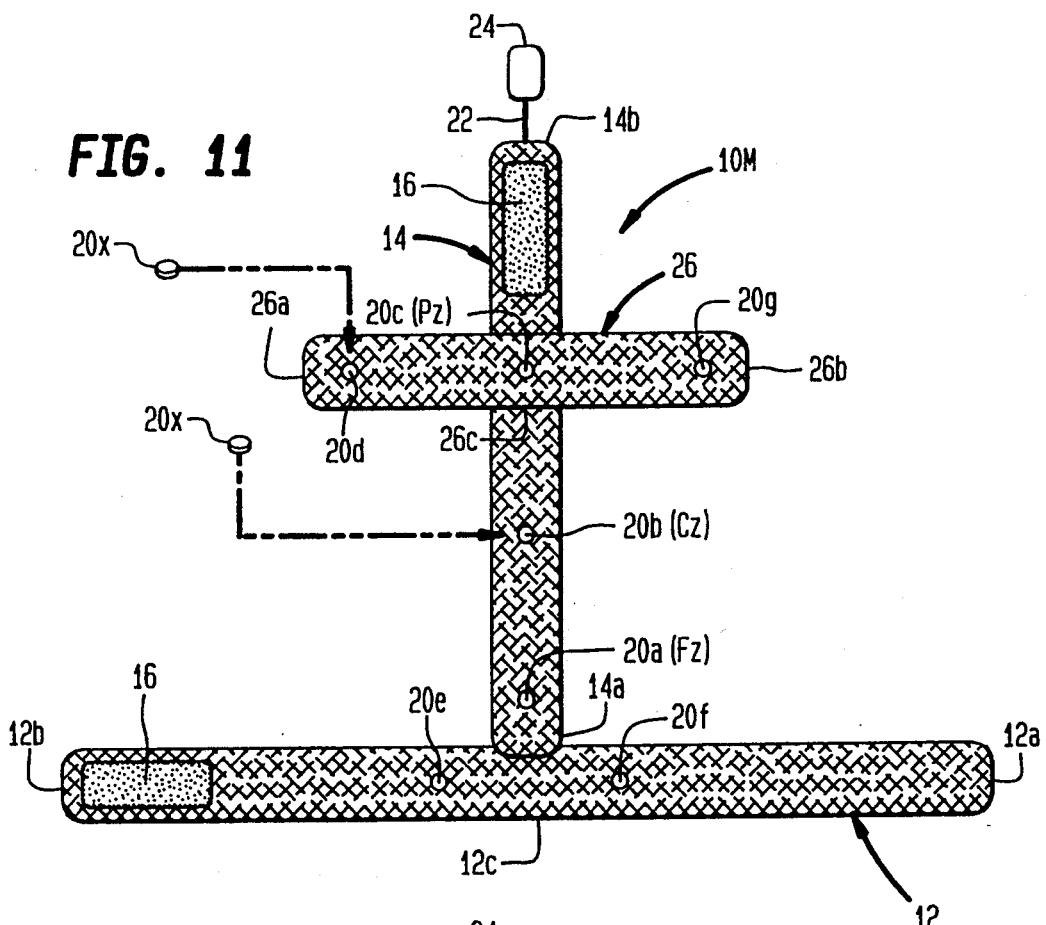
FIG. 11 is a schematic of the posterior side of the "mastoid-flap" version of the headband, which has a secondary crossbar attached perpendicularly to the overflap. The figure indicates placement of electrodes on the band, overflap, and secondary crossbar, as well as Velcro loops.
Figure 12:
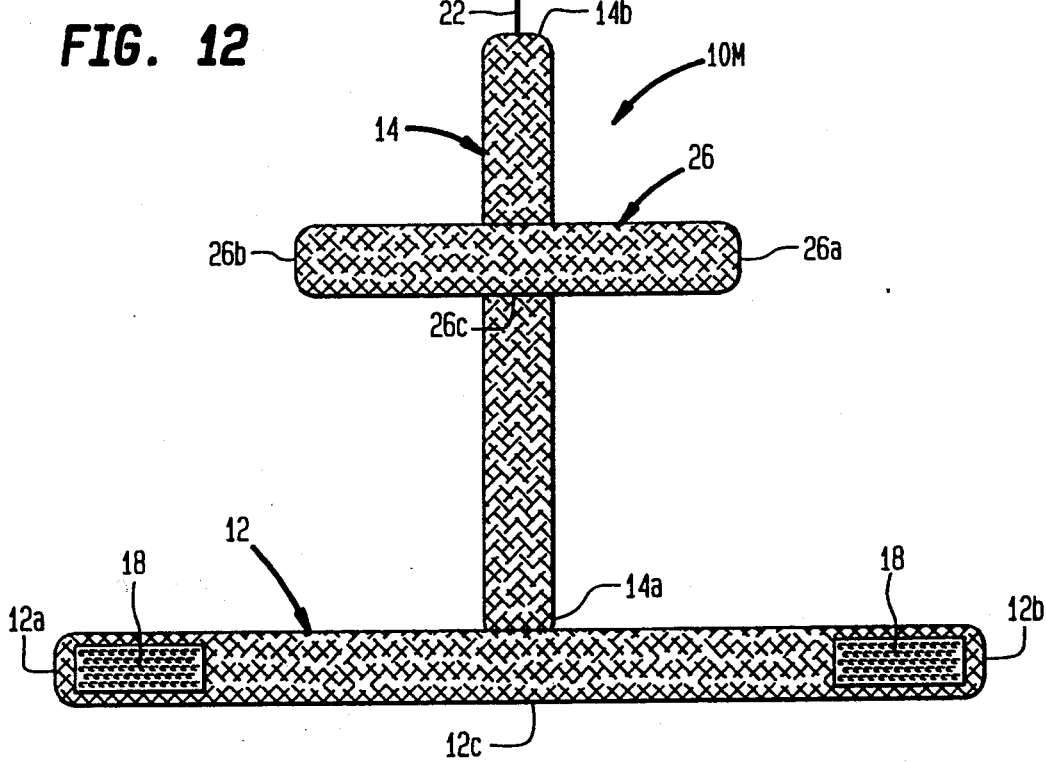
FIG. 12 is a schematic of the anterior side of the "mastoid-flap" version of the headband, showing the secondary crossbar's featureless anterior side and the placement of Velcro hook pads.

Illustrated in FIGS. 11 and 12 is an alternate embodiment of the headband referred to as a Mastoid-flap headband 10M. The second headband 10M is similar to the basic headband 10 with the band 12, overflap 14, and Velcro pads 16, 18, but further includes a secondary crossbar 26 attached to an intermediate portion of the overflap 14 at the parietal (Pz) electrode site and being disposed generally parallel to the band 12 as shown. The crossbar 26 has first and second opposite distal ends 26a and 26b, and a center section 26c joined to the overflap 14.

The crossbar 26 is sized for positioning the first and second ends 26a,b thereof underneath the band 14 behind the ears when installed on the subject's head. In this embodiment, the electrode sites 20a–c for the frontal (Fz), central (Cz), and parietal (Pz) locations are disposed along the overflap 14, and the electrode sites 20d, 20g for the left and right mastoid locations are disposed along the secondary crossbar 26 adjacent to the first and second ends 26a,b, respectively. Since the secondary crossbar is attache to the overflap 14 at the parietal (Pz) location, the electrode sites 20d, 20c, and 20b for the left mastoid, parietal (Pz), and right mastoid locations, respectively, are colinearly spaced apart along the secondary crossbar 26 for holding the corresponding electrodes in place at the desired locations when the secondary crossbar 26 is inserted behind the ears under the installed band 12.

The mastoid-flap headband 10M increases the mobility of the left and right mastoid electrodes by moving them to the secondary crossbar 26 attached to the overflap at the level of the top Pz electrode (see FIGS. 11 and 12). When the band is positioned around the head and the overflap fastened in place, the ends of the secondary crossbar may be inserted behind the ears underneath the band, which holds the electrodes in place at the desired location.

The ideal approximate dimensions of the primary crossbar and the overflap are identical to the basic headband without the mastoid electrodes. The secondary crossbar should measure about 5" end to end and 1" across and be attached to the overflap approximately 6" from the mouth. The left and right mastoid electrodes should be placed approximately 0.75" from either end of the secondary crossbar.

Velcro-Sizing Headband

Illustrated in FIGS. 13 and 14 is an alternate embodiment of the headband referred to as a Velcro-sizing headband 10V. The third headband 10V is similar to the basic headband 10 with the band 12, overflap 14, Velcro pads 16,18, and electrode sites 20a–g, but further includes a plurality of spaced apart, flexible, rectangular flaps 28a–g fixedly joined at one edge thereof to the anterior side of the band 12 and the overflap 14. There are preferably seven flaps 28a-g, one each for each of the corresponding electrode sites 20a-g, disposed on the anterior side behind each of the electrode sites 20a-g on the posterior side.

Each of the seven flaps 28a-g has a Velcro hook pad 30 on its underside which mates with a complementary Velcro loop pad 32 sewn on the anterior side of the band 12 or the overflap 14. The complementary pairs of Velcro hook and loop pads 30,32 releasably join together each of the flaps 28a-g with the band 12 or the overflap 14 by tightening and loosening to increase the mobility or position of each electrode site 20a-g, and the electrode thereat.

The Velcro-sizing headband 10V (see FIGS. 13 and 14) allows increased mobility of each individual electrode by attaching flaps to the anterior side behind each electrode which can be tightened and loosened. Each flap approximates the width of the band and overflap and runs parallel to them, has a pad of Velcro hooks on its underside, and fastens to a pad of Velcro loops sewn directly onto the anterior side of the headband. The optimal approximate length of each flap is 3.5", with a 3.25" Velcro pad sewn in lengthwise; the other Velcro pad should be about 4" long.

| APPENDIX | | |
|---|---|---|
| The stimuli used in Experiment 1 | | |
| PROBE | TARGET | IRRELEVANT |
| Scenario 1 | | |
| Blue Coat | Green Hat | Brown Shoes |
| | | Red Scarf |
| | | Gray Pants |
| | | Black Gloves |
| Phil Jenks | Tim Howe | Ray Snell |
| | | Neil Rand |
| | | Gene Falk |
| | | Ralph Croft |
| Op Cow | Op Pig | Op Horse |
| | | Op Goat |
| | | Op Sheep |
| | | Op Mule |
| Rain File | Snow File | Hail File |
| | | Wind File |
| | | Sleet File |
| | | Fog File |
| Sub Plans | Ship Plans | Tank Plans |
| | | Plane Plans |
| | | Bomb Plans |
| | | Gun Plans |
| Perch Street | Shark Street | Cod Street |
| | | Carp Street |
| | | Pike Street |
| | | Trout Street |
| Scenario 2 | | |
| White Shirt | Green Tie | Beige Suit |
| | | Red Vest |
| | | Tan Belt |
| | | Black Socks |
| Dale Spence | Wayne Brant | Glenn Platt |
| | | Walt Rusk |
| | | Tod Ames |
| | | Earl Dade |
| Op Spruce | Op Fir | Op Oak |
| | | Op Birch |
| | | Op Elm |
| | | Op Pine |
| Owl File | Swan File | Wren File |
| | | Duck File |
| | | Crow File |
| | | Goose File |
| Brass Plans | Steel Plans | Tin Plans |
| | | Zinc Plans |
| | | Lead Plans |
| | | Iron Plans |
| Lion Street | Fox Street | Deer Street |
| | | Wolf Street |
| | | Bear Street |
| | | Elk Street |

REFERENCES CITED IN THE SPECIFICATION

Allison, T., Wood, C. C., & McCarthy, G. (1986). The central nervous system. In M. G. H. Coles, S. W. Porges, & E. Donchin (Eds.), Psychophysiology: Systems, Processes, and Applications (pp. 5-25). New York, NY: Guilford.

Andersen, P. & Andersson, S. A. (1968). Physiological Basis of the Alpha Rhythm. New York: Appleton-Century-Crofts.

Ansley, N. (Ed.) (1975). Legal Admissibility of the Polygraph. Springfield, Ill.: Charles C. Thomas.

Appian of Alexandria, early second century A.D. (1962). The Syrian wars. In H. White (Transl.), Roman History (XI, cap. x. Vol. 2.). Cambridge, Mass.: Loeb Classical Library.

Aubry, A. S. & Caputo, R. R. (1980). Criminal Interrogation (Third Edition). Springfield, Ill.: Charles C. Thomas.

Ax, A. F. (1953). Goals and methods of psychophysiology. Psychophysiology, 1, 8-25.

Backster, C. (1962). Methods of strengthening our polygraph technique. Police, 6, 61-68.

Baddeley, A.D. (1981). The concept of working memory: a view of its current state and probable future development. Cognition, 10: 17-23.

Baddeley, A.D. (1990). Human Memory: Theory and Practice. Boston: Allyn and Bacon.

Baddeley, A.D. & Hitch, G. J. (1974). Working memory. In G. A. Bower (Ed.), The Psychology of Learning and Motivation: Vol. 8, Academic Press, New York.

Balloun, K. D. & Holmes, D. S. (1979). Effects of repeated examinations on the ability to detect guilt with a polygraphic examination: A laboratory experiment with a real crime. Journal of Applied Psychology, 64, 316-322.

Barland, G. H. (1981). A Validity and Reliability Study of Counterintelligence Screening Test. Fort George G. Meade, Maryland: Security Support Battalion, 902d Military Intelligence Group. Barland, G. H. (1982). Detection of Deception Theory. Unpublished.

Barland, G. H. (1985). Criminal investigation. Society, 22, 46-51.

Barland, G. H. (1988). The polygraph test in the USA and elsewhere. In A. Gale (Ed.), The Polygraph Test: Lies, Truth and Science. London: Sage Publications.

Barland, G. H. & Raskin, D.C. (1973). Detection of deception. In W. F. Prokasy & D.C. Raskin (Eds.), Electrodermal Activity in Psychological Research (pp. 417-477). New York: Academic Press.

Barland, G. H. & Raskin, D.C. (1975). An evaluation of field techniques in detection of deception. Psychophysiology, 12, 321-330.

Barland, G. H. & Raskin, D.C. (1976). Validity and Reliability of Polygraph Examinations of Criminal Suspects (report No. 76-1, contract No. 75-N1-99-0001). Washington, D.C.: National Institute of Justice, Department of Justice.

Ben-Shakar, G., Bar-Hillel, M., & Lieblich, I. (1986), Trial by polygraph: Scientific and juridical issues in lie detection. Behavioral Sciences and the Law, 4, 459–479.

Ben-Shakar, G., Lieblich, I., & Kugelmass, S. (1975). Detection of information and GSR habituation: An attempt to derive detection efficiency from two habituation curves. Psychophysiology, 12, 283–288.

Benussi, V. (1914). Die atmungssymptome der luge. Archives of Ges. Psychologie, 31, 244.

Bersh, P. J. (1969). A validation study of polygraph examiner judgements. Journal of Applied Psychology, 53, 399–403.

Bower, G. H. (1981). Mood and memory. American Psychologist, 36, 129–148.

Bradley, M. T. & Ainsworth, D. (1984). Alcohol and the psychophysiological detection of deception. Psychophysiology, 21, 63–71.

Bradley, M. T. & Janisse, M.P. (1981). Accuracy demonstrations, threat and the detection of deception: Cardiovascular, electrodermal, and pupillary measures. Psychophysiology, 18, 307–314.

Bradley, M. T. & Warfield, J. F. (1984). Innocence, information, and the guilty knowledge test in the detection of deception. Psychophysiology, 21, 683–689.

Brewer, W. F. (1986). What is autobiographical memory? In Rubin, D.C. (Ed.), Autobiographical Memory. Cambridge: Cambridge University Press.

Brown, B. (1971). Awareness of EEG-subjective activity relationships detected within a closed-feedback system. Psychophysiology, 7, 451–464.

Brown, R. & Kulik, J. (1977). 'Flashbulb memories.' Cognition, 5, 73–99.

Buchwald, J. & Squires, N. (1982). Endogenous auditory potentials in the cat: a P300 model. In C. Woody (Ed.), Conditioning (pp. 503–515). New York: Plenum.

Bunuel, L. (1985). My Last Breath. London: Fontaria.

Burtt, H. E. (1918). A pneumograph for inspiration-expiration ratios, Psychological Bulletin, 15, 325.

Burtt, H. E. (1921a). The inspiration-expiration ratio during truth and falsehood. Journal of Experimental Psychology, 4, 1–23.

Burtt, H. E. (1921 b). Further technique for inspiration-expiration ratios. Journal of Experimental Psychology, 4, 106–110.

Coles, M. G. H., Donchin, E. & Porges, S. W. (Eds.) (1986). Psychophysiology: Systems, Processes, and Applications. New York: Guilford Press.

Conway, M. A. (1990). Autobiographical Memory: An Introduction. Philadelphia: Open University Press.

Courchesne, E., Hillyard, S. A., & Galambos, R. (1975). Stimulus novelty, task relevance and the visual evoked potential in man. Electroencephalography and Clinical Neurophysiology, 39, 131–143.

Davidson, P.O. (1968). Validity of the guilty-knowledge technique: The effects of motivation. Journal of Applied Psychology, 52, 62–65.

Davidson, W. A. (1979). Validity and reliability of the Cardio Activity Moniter. Polygraph, 8, 104–111.

Davidson, R. J. (1984a). Affect, cognition and hemispheric specialization. In C. E. Izard, J. Kagan, & R. Zajonc (Eds.), Emotion, Cognition and Behavior (pp. 320–365). New York: Cambridge University Press.

Davidson, R. J. (1984b). Hemispheric asymmetry and emotion. In K. Scherer & P. Ekman (Eds.), Approaches to Emotion (pp. 39–57). Hillsdale, N.J.: Erlbaum.

Davidson, R. J. (1987). Cerebral asymmetry and the nature of emotion: Implications for the study of individual differences and psychopathology. In R. Takahashi, P. Flor-Henry, J. Gruzelier, & S. Niwa (Eds.), Cerebral Dynamics, Laterality and Psychopathology (pp. 71–83). New York: Elsevier.

Davidson, R. J. & Tomarken, A. J. (1989). Laterality and emotion: An electrophysiological approach. In F. Boiler & J. Grafman (Eds.), Handbook of Neuropsychology Volume 3 (pp. 419–441). Amsterdam: Elsevier.

Davidson, R. J., Ekman, P., Saron, C. D., Senulis, J. A., & Friesen, W. V. (1990). Approach-withdrawal and cerebral asymmetry: Emotional expression and brain physiology I. Journal of Personality and Social Psychology, 58, 330–341.

Davis, R. C. (1961). Physiological responses as a means of evaluating information. In A.D. Biderman, & H. Zimmer (Eds.), The Manipulation of Human Behavior (142–168). New York: Wiley.

Dawson, M. E. (1980). Physiological detection of deception: Measurement of responses to questions and answers during countermeasure maneuvers. Psychophysiology, 17, 8–17.

Department of Defense, (1984). The Accuracy and Utility of Polygraph Testing. Washington, D.C.: Department of Defense.

Desmedt, J. E. (1980). P300 in serial tasks: An essential post-decision closure mechanism. In H. H. Kornhuber, & L. Deecke (Eds.), Motivation, Motor and Sensory Processes of the Brain. Progress in Brain Research, 54: 682–686. Amsterdam: Elsevier-North Holland.

Desmedt, J. E. (1981). Scalp-recorded cerebral event-related potentials in man as point of entry into the analysis of cognitive processing. In F. O. Schmitt, F. G. Worden, G. Adelman, & S. D. Dennis (Eds.), The Organization of the Cerebral Cortex (chapter 19, pp. 441–473). Cambridge, Mass.: The MIT Press.

Desmedt, J. E. & Debecker, J. (1979a). Wave form and neural mechanism of the decision P350 elicited without pre-stimulus CNV or readiness potential in random sequences of near-threshold auditory clicks and finger stimuli. Electroencephalography and Clinical Neurophysiology, 47, 648–670.

Desmedt, J. E. & Debecker, J. (1979b). Slow potential shifts and decision making: P350 interactions in tasks with random sequences of near-threshold clicks and finger stimuli delivered at regular intervals. Electroencephalography and Clinical Neurophysiology, 47, 671–679.

Diaconis, P. & Efron, B. (1983). Computer-intensive methods in statistics. Scientific American, 248, 116–130.

Donchin, E. (1979). Event-related brain potentials: A tool in the study of human information processing. In H. Begleiter (Ed.), Evoked Potentials and Behavior (pp. 13–75). New York: Plenum.

Donchin, E. (1981). Surprise! Surprise? Psychophysiology, 18, 493–513.

Donchin, E. & Cohen, L. (1967). Average evoked potentials and intramodality selective attention. Electroencephalography and Clinical Neurophysiology, 22, 537–546.

Donchin, E. & Coles, M. G. H. (1988a). Is the P300 component a manifestation of context updating? Behavioral and Brain Sciences, 11, 357-372.

Donchin, E. & Coles, M. G. H. (1988b). On the conceptual foundations of cognitive psychophysiology. Behavioral and Brain Sciences, 11, 406-415.

Donchin, E., Gratton, G., Dupree, D., & Coles, M. G. H. (1988). After a rash action: Latency and amplitude of the P300 following fast guesses. In G. Galbraith, M. Klietzman, & E. Donchin (Eds.), Neurophysiology and Psychophysiology: Experimental and Clinical Applications (pp. 173-188). Hillsdale, N.J.: Lawrence Erlbaum.

Donchin, E. & Heffley, E. (1978). Multivariate analysis of event-related brain potential data: A tutorial review. In D. Otto (Ed.), Multidisciplinary Perspectives in Event-related Potential Research, (pp. 555-572). EPA-600/9-77-043, Washington, D.C.: U.S. Government Printing Office.

Donchin, E., Kramer, A. F., & Wickens, C. (1986). Applications of brain event-related potentials to problems in engineering psychology. In M. G. H. Coles, E. Donchin, & S. Porges (Eds.), Psychophysiology: Systems, Processes, and Applications. New York: Guilford Press.

Donchin, E., Karis, D., Bashore, T. R., Coles, M. G. H., & Gratton, G. (1986). Cognitive psychophysiology and human information processing. In M. G. H. Coles, E. Donchin, & S. W. Porges (Eds.), Psychophysiology: Systems, Processes and Applications (pp. 244-267). New York: Guilford Press.

Donchin, E., McCarthy, G., Kutas, M., & Ritter, W. (1983). Event-related brain potentials in the study of consciousness. In R. Davidson, G. Schwartz, and D. Shapiro (Eds.), Consciousness and Self Regulation, Volume 3. New York: Plenum Press, 81-121.

Donchin, E., Ritter, W., & McCallum, W. C. (1978). Cognitive psychophysiology: The endogenous components of the ERP. In E. Callaway, P. Tueting, & S. Koslow (Eds.), Brain Event-related Potentials in Man (pp. 349-441). New York: Academic Press.

Donchin, E., Tueting, P., Ritter, W., Kutas, M., & Heffley, E. (1975). On the independence of the CNV and the P300 components of the human averaged evoked potential. Electroencephalography and Clinical Neurophysiology, 38, 449-461.

Duncan-Johnson, C. C., & Donchin, E. (1977). On quantifying surprise: The variation of event-related brain potentials with subjective probability. Psychophysiology, 14, 456-467.

Edel, E. C. & Jacoby, J. (1975). Examiner reliability in polygraph chart analysis: Identification of physiological responses. Journal of Applied Psychology, 60, 632-634.

Efron, B. (1979). Bootstrap methods: Another look at the jackknife. Annals of Statistics, 7, 1-26.

Efron, B. (1982). The jackknife, the bootstrap, and other resampling plans. Society of Industrial and Applied Mathematics, 38, CMVS-NSF monographs.

Efron, B. & Gong, G. (1983). A leisurely look at the bootstrap, the jackknife, and cross-validation. American Statistician, 37, 36-48.

Ekman, P. (1985). Telling lies: Clues to Deceit in the Marketplace, Politics, and Marriage. New York: Norton.

Ekman, P., Davidson, R. J., & Friesen, W. V. (1990). The Duchenne smile: Emotional expression and brain physiology II. Journal of Personality and Social Psychology, 58, 342-353.

Elaad, E. & Ben-Shakar, G. (1989). Effects of motivation and verbal response type on psychophysiological detection of information. Psychophysiology, 26, 442-451.

Eysenck, M. W., Mogg, K., May, J., Richards, A., & Mathews, A. (1991). Bias in interpretation of ambiguous sentences related to threat in anxiety. Journal of Abnormal Psychology, 100, 144-155.

Fabiani, M., Gratton, G., Karis, D., & Donchin, E. (1987). The definition, identification, and reliability of measurement of the P300 component of the event-related brain potential. In P. K. Ackles, J. R. Jennings, & M. G. H. Coles (Eds.), Advances in Psychophysiology, 2, (pp. 1-78). Greenwich, Conn.: JAI Press, Inc.

Fabiani, M., Karis, D., & Donchin, E. (1986). P300 and recall in an incidental memory paradigm. Psychophysiology, 23, 298-308.

Fabiani, M., Karis, D., & Donchin, E. (1990). Effects of mnemonic strategy manipulation in a Von Restorff paradigm. Electroencephalography and Clinical Neurophysiology, 75, 22-35.

Farwell, L. A. (1991). The Brain-wave Information Detection (BID) System: A New Paradigm for Psychophysiological Detection of Information. Unpublished doctoral dissertation, University of Illinois at Urbana-Champaign.

Farwell, L. A., Martinerie, J. M., Bashore, T. B., Rapp, P. E.. & Goddard, P. (1993). Optimal digital filters for long latency event-related brain potentials. In Press, Psychophysiology. Farwell, L. A. & Donchin, E. (1986). The "brain detector": P300 in the detection of deception. Psychophysiology, 24, 434 (Abstract).

Farwell, L. A. & Donchin, E. (1988). The truth will,-out: Interrogative polygraphy with event-related brain potentials. Psychophysiology, 25, 445 (Abstract).

Farwell, L. A. & Donchin, E. (1989). Detection of guilty knowledge with ERPs. Psychophysiology, 26, 4A, S8.

Farwell, L. A., & Donchin, E. (1991). The truth Will out: Interrogative polygraphy ("lie detection") with event-related brain potentials. Psychophysiology, 28, 531-547.

Ferguson, R. J. & Miller, A. L. (1973). The Polygraph in Court. Springfield: Thomas.

Ferguson, R. J. & Miller, A. L. (1974). Polygraph for the Defense. Springfield, Ill.: Charles C. Thomas.

Ferraro, G.L. (1911). Criminal Man: According to the Classification of Cesare Lombroso. New York: G.P. Putnam's Sons.

Forman, R. F. & McCauley, C. (1986). Validity of the positive control polygraph test using the field practice model. Journal of Applied Psychology, 71, 691-698.

Furedy, J. J. (1987). Evaluating polygraphy from a psychophysiological perspective: A specific-effects analysis. Pavlovian Journal of Biological Science, 22, 145-152.

Furedy, J. J. & Helsgrave, R. J. (1988). Validity of the lie detector: A psychophysiological perspective. Criminal Justice and Behavior, 15, 219-246.

Gale, A. (1988). Introduction: The polygraph test, more than scientific investigation. In A. Gale (Ed.), The Polygraph Test: Lies, Truth and Science. London: Sage Publications.

Galen of Pergamum, second century A.D. (1827). De praenotione. In D.C. G. Kuhn (Ed.), Opera omnia (cap. vi. Vol. 9) (pp. 630–635). Lipsiae: Officina Libraria Car. Cnoblochii.

Galton, F. (1883). Inquiries into Human Faculty and its Development. London: Macmillan, 1st edition.

Gatchel, R. J., Smith, J. E., & Kaplan, N.M. (1984). The Effect of Propanol on Polygraphic Detection of Deception. Unpublished manuscript, University of Texas Health Sciences Center.

Gay, W. O. (1948). The search for truth. English Police Journal, 21, 284.

Giesen, M., & Rollison, M.A. (1980). Guilty knowledge verses innocent associations: Effects of trait anxiety and stimulus context on skin conductance. Journal of Research on Personality, 14, 1–11.

Ginton, A., Dale, N., Elaad, E., & Ben-Shakar, G. (1982). A method for evaluating the use of the polygraph in a real-life situation. Journal of Applied Psychology, 62, 131–137.

Gratton, G., Bosco, C. M., Kramer, A. F., Coles, M. G. H., Wickens, C. D., & Donchin, E. (1990). Event-related brain potentials as indices of information extraction and response priming. Electroencephalography and Clinical Neurophysiology, 75, 419–432.

Gugas, C. (1979). The Silent Witness. Englewood Cliffs, N J: Prentice-Hall, Inc.

Halgren, E., Squires, N. K., Wilson, C. L., Rohrbaugh, J. W., Babb, T. L., & Randall, P. H. (1980). Endogenous potentials generated in the human hippocampal formation and amygdala by infrequent events. Science, 210, 803–805.

Hammond, D. L. (1980). The Responding of Normals, Alcoholics, and Psychopaths in a Laboratory Lie-detection Experiment. California School of Professional Psychology, Unpublished Doctoral Dissertation.

Harrelson, L. H. (1964). The Keeler Technique (Second Edition). Chicago: Keeler Polygraph Institute.

Heffley, E. F. (1985). Elements of a neural theory of human information processing derived from an analysis of cognitive event-related potentials. Manuscript in preparation. Cited in Donchin, E., Karis, D., Bashore, T. R., Coles, M. G. H., & Gratton, G. (1986). Cognitive psychophysiology and human information processing. In Coles, M. G. H., Donchin, E. & Porges, S. W. (Eds.) (1986). Psychophysiology: Systems, Processes, and Applications. New York: Guilford Press. Heffley, E., Wickens, C. D., & Donchin, E. (1978). Intramodality selective attention and P300-reexamination in a visual monitoring task. Psychophysiology, 15, 269–270.

Hillyard, S. A. (1984). Event-related brain potentials and selective attention. In E. Donchin (Ed.), Cognitive Psychophysiology: Event-related Potentials and the Study of Cognition. The Carmel Conferences, 1, (pp. 51–72). Hillsdale, N.J.: Erlbaum.

Hillyard, S. A. & Kutas, M. (1983). Electrophysiology of cognitive processing. In M. R. Rosenzweig & L. W. Porter (Eds.), Annual Review of Psychology, 34, (pp. 33–61). Palo Alto, Calif.: Annual Reviews, Inc.

Honts, C. R., Hodes, R. L., & Raskin, D.C. (1985). Effects of physical counter-measures on the physiological detection of deception. Journal of Applied Psychology, 70, 177–187.

Honts, C. R., Raskin, D.C., & Kircher, J. C. (1983). Detection of deception: Effectiveness of physical countermeasures under high motivation conditions. Psychophysiology, 20.

Honts, C. R., Raskin, D.C., & Kircher, J. C. (1987). Effects of physical countermeasures and their electromyographic detection during polygraph tests for deception. Journal of Psychophysiology, 1, 241–247.

Horst, R., Johnson, R., & Donchin, E. (1980). Event-related brain potentials and subjective probability in a learning task. Memory and Cognition, 8, 476–488.

Horvath, F. S. (1973). Verbal and nonverbal clues to truth and deception during polygraph examinations. Journal of Police Science and Administration, 1, 138–152.

Horvath, F. S. (1975). The accuracy and reliability of police polygraphic ("lie detector") examiners' judgments of truth and deception: The effect of selected variables. Dissertation Abstracts International, 36, 420B–421B.

Horvath, F. S. (1977). The effect of selected variables on interpretation of polygraph records. Journal of Applied Psychology, 62, 127–136.

Horvath, F. S. (1985). Job Screening. Society, 22, 43–46.

Horvath, F. S., & Reid, J. E. (1971). The reliability of polygraph examiner diagnoses of truth and deception. Journal of Criminal Law, Criminology, and Police Science, 62, 276–281.

Hudson, J. A. & Fivush, R. (1987). As time goes by: Sixth graders remember a kindergarten experience. Report No. 13, Emory Cognition Project. Cited in Baddeley, A.D. (1990). Human Memory: Theory and Practice (pp. 309). Boston: Allyn and Bacon.

Hunter, F. L. & Ash, P. (1973). The accuracy and consistency of polygraph examiners diagnosis. Journal of Police Science and Administration, 1, 370–375.

Iacono, W. G (1985). Guilty knowledge. Society, 22, 52–54.

Iacono, W. G., Boisvenu, G. A., & Fleming, J. A. (1984). Effects of diazepam and methylphenidate on the electrodermal detection of guilty knowledge. Journal of Applied Psychology, 69, 289–299.

Iacono, W. G., Cerri, A.M., Patrick, C. J., & Fleming, J. A. E. (1987). The effect of antianxiety drugs on the detection of deception. Psychophysiology, 24, 594.

Ibn Sina (Avicenna, tenth century A.D.) (1608). De ilisci. Insania ex amoribus. In Canon Medicinae (Liber III, Tract. 4, cap. 24. Vol. 1) (pp. 494). Venice: Apud Iuntas.

Inbau, F. E. & Reid, J. E. (1953). Lie Detection and Criminal Investigation (3rd Edition). Baltimore: Williams and Wilkins Company.

Inbau, F. E. & Reid, J. E. (1962). Criminal Interrogation and Confessions. Baltimore: Williams and Wilkins Company.

Isreal, J. B., Chesney, G. L., Wickens, C. D., & Donchin, E. (1980). P300 and tracking difficulty: Evidence for multiple resources in dual task performance. Psychophysiology, 17, 259–273.

Isreal, J. B., Wickens, C. D., Chesney, G. L., & Donchin, E. (1980). The event-related brain potentials: An index of display monitoring workload. Human Factors, 22, 212–224.

Jasper, H. H. (1958). The ten-twenty electrode system of the International Rederation. Electroencephalography and Clinical Neurophysiology, 10, 371–375.

Jennings, J. R. (1986). Bodily changes during attending. In M. G. H. Coles, E. Donchin, & S. W. Porges (Eds.), Psychophysiology: Systems, Processes, and Applications, (pp. 268–289). New York: Guilford Press.

Johnson, M. K. (1983). A multiple entry, modular memory system. In G. H. Bower, (Ed.), The psychology of learning and motivation: Advances in Research Theory, 17, (81–123). New York: Academic Press.

Johnson, M. K. (1985). The origin of memories. In Kendall, P. C. (Ed.), Advances in Cognitive-behavioural Research and Therapy, 4, 1–27. New York: Academic Press.

Johnson, R. Jr. (1986). A triarchic model of P300 amplitude. Psychophysiology, 23, 367–384.

Johnson, R. Jr. & Donchin, E. (1979). On how P300 amplitude varies with the utility of the eliciting stimuli. Electroencephalography and Clinical Neurophysiology, 44, 424–437.

Johnson, R. Jr. & Donchin, E. (1982). Sequential expectancies and decision making in a changing environment: An electrophysiological approach. Psychophysiology, 19, 183–200.

Johnson, R. Jr. & Fedio, P. (1984). P300 elicited by auditory and visual stimuli in temporal lobectomy patients. Paper presented at the Third International Conference on Cognitive Neuroscience (ICON). Bristol: England.

Johnson, R. Jr. & Fedio, P. (1986). Pre- and post-surgical event-related potentials in epilepsy patients. Psychophysiology, 23, 444–445.

Kandel, E. R. & Schwartz, J. H. (1985). Principles of Neural Science. North Holland: Elsevier. Karis, D., Chesney, G. L., & Donchin, E. (1983). "... 'twas ten to one; And yet we ventured...": P300 and decision making. Psychophysiology, 20, 260–268.

Karis, D., Fabiani, M., & Donchin, E. (1984). P300 and memory: Individual differences in the von Restorff effect. Cognitive Psychology, 16, 177–216.

Keeler, L. (1930). A method for detecting deception. American Journal of Police Science, 1, 38–51.

Kinsborne, M. & Bemporad, B. (1984). Lateralization of emotion: A model and the evidence. In N. A. Fox & R. J. Davidson (Eds.), The Psychobiology of affective development (pp. 259–291). Hillsdale, N.J.: Erlbaum.

Kircher, J. C. (1983). Computerized Decision-making and Patterns of Activation in the Detection of Deception. Unpublished doctoral dissertation, University of Utah.

Kircher, J. C. & Horowitz, S. W., & Raskin, D.C. (1988). Meta-analysis of mock crime studies of the control question polygraph technique. Law and Human Behavior, 12, 79–90.

Kircher, J. C. & Raskin, D.C. (1981). Computerized decision-making in the detection of deception. Psychophysiology, 18, 204–205.

Kircher, J. C. & Raskin, D.C. (1982). Cross-validation of a computerized diagnostic procedure for detection of deception. Psychophysiology, 19 (5).

Kircher, J. C. & Raskin, D.C. (1988). Human versus computerized evaluations of polygraph data in a laboratory setting. Journal of Applied Psychology, 73, 291–302.

Klein, M., Coles, M. G. H., & Donchin, E. (1984). People with absolute pitch process tones without producing a P300. Science, 223, 1306–1309.

Kleinmuntz, B. & Szucko, J. J. (1982). On the fallibility of lie detection. Law-and-Society Review, 17, 85–104.

Kleinmuntz, B. & Szucko, J. J. (1984). Lie detection in ancient and modern times: A call for contemporary scientific study. American Psychologist, 39, 766–776.

Kleinsmith, L. J. & Kaplan, S. (1963). Paired associated learning as a function of arousal and interpolated interval. Journal of Experimental Psychology, 65, 190–193.

Knight, R. T., Scabini, D., Woods, D. L., & Clayworth, C. C. (1989). Contributions of temporal-parietal junction to the human auditory P3. Brain Research, 502, 109–116.

Kramer, A., Schneider, W., Fisk, A., & Donchin, E. (1986). The effects of practice and task structure on components of the event-related brain potential. Psychophysiology, 23, 33–47.

Kutas, M. & Donchin, E. (1980). Preparation to respond as manifested by movement-related brain potential. Brain Research, 202, 95–115.

Kutas, M. & Hillyard, S. A. (1980). Reading senseless sentences: Brain potentials reflect semantic incongruity. Science, 207, 203–205.

Kutas, M., McCarthy, G., & Donchin, E. (1977). Augmenting mental chronometry: The P300 as a measure of stimulus evaluation time. Science, 197, 792–795.

Kutas, M., Van Petten, C. (1989). Event-related brain potential studies of language. In P. K. Ackles, J. R. Jennings & M. G. H. Coles (Eds.), Advances in Psychophysiology, 3, (pp. 139–187). Greenwich, Conn.: JAI Press, Inc.

Lacey, J. I. (1967). Somatic response patterning and stress: Some revisions of activation theory. In M. H. Appley and R. Trumbull (Eds.), Psychological Stress: Issues in Research (pp. 14–37). New York: Appleton-Century-Crofts.

Lacey, J. I. & Lacey, B.C. (1970). Some autonomic-central nervous system interrelationships. In P. Black (Ed.), Physiological Correlates of Emotion. New York: Academic Press.

Lang, P. J., Bradley, M. M., & Cuthbert, B. N. (1990). Emotion, attention, and the startle reflex. Psychological Review, 97, 377–395.

Larson, J. A. (1921). Modification of the Marston Deception Test. Journal of Law and Criminology American Institute, XII, 390–399.

Larson, J. A. (1922). The Cardio-pneumo-psychogram and its use in the study of emotions, with practical application. Journal of Experimental Psychology, 5.

Larson, J. A. (1932). Lying and Its Detection. Chicago: University of Chicago Press.

Larson, J. A. (1969). Lying and Its Detection (Reprinting). Philadelphia: Patterson Smith.

Leippe, M. R., Wells, G. L., & Ostrom, T. M. (1978). Crime seriousness as a determinant of accuracy in eyewitness identification. Journal of Applied Psychology, 63, 345–351.

Leventhal, H. & Tomarken, A. J. (1986). Emotion! Today's problems, In M. R. Rosenzweig, & L. Y. Porter (Eds.), Annual Review of Psychology (Vol. 37, pp. 565–610). Palo Alto, Calif.: Annual Reviews, Inc..

Linton, M. (1975). Memory for real-world events. In D. A. Norman & D. E. Rumelhart (Eds.), Explorations in Cognition (pp. 376–404). San Francisco: Freeman.

Linton, M. (1979). I remember it well. Psychology Today, July, 80–86.

Lippold, D.C. J. & Novotny, G. E. K. (1970). Is alpha rhythm an artifact? Lancet, I, 976–979.

Loftus, E. F. & Burns, T. E. (1982). Mental shock can produce retrograde amnesia. Memory and Cognition, 10, 318–323.

Lombroso, C. (1890). L'Anthropologie criminelle. Paris: Sous Presse.

Lombroso, C. (1887). L'Homme Criminel: Etude Anthropologique Et Medico-Legale. Paris: Felix Alcan.

Lombroso, C. (1911). Crime: Its Causes and Remedies. Boston: Little, Brown and Company.

Lombroso, C. (1912). Crime: Its Causes and Remedies. Boston: Little, Brown and Company.

Lykken, D. T. (1959). The GSR in the detection of guilt. Journal of Applied Psychology, 43, 385–388.

Lykken, D. T. (1960). The validity of the guilty knowledge technique: Effects of faking. Journal of Applied Psychology, 44, 258–262.

Lykken, D. T. (1974). Psychology and the lie detector industry. American Psychologist, 29, 725–739.

Lykken, D. T. (1978). The psychopath and the lie detector. Psychophysiology, 15, 137–142.

Lykken, D. T. (1979). Methods of Polygraphic Interrogation. Final Report to Law Enforcement Assistance Administration. Minneapolis: University of Minnesota.

Lykken, D. T. (1981). A Tremor in the Blood: Uses and Abuses of the Lie Detector. New York: McGraw Hill.

Lykken, D. T. (1985). Detecting deception. Society, 22, 34–39.

Lykken, D. T. (1988). Detection of guilty knowledge: A comment on Forman and McCauley. Journal of Applied Psychology, 73, 303–304.

Lynch, J. J. & Paskewitz, D. A. (1971). On the mechanisms of the feedback control of human brain wave activity. Journal of Nervous and Mental Disease, 153, 205–217.

Mackenzie, J. Sir (1908). The ink polygraph. British Medical Journal, I 1411. Cited in W. O. Gay, (1948), The search for truth. English Police Journal, 21, 284.

Magliero, A., Bashore, T., Coles, M. G. H., & Donchin, E. (1984). On the dependence of P300 latency on stimulus evaluation processes. Psychophysiology, 1984, 21, 171–186.

Marston, W. M. (1917). Systolic blood pressure symptoms of deception. Journal of Experimental Psychology, 2, 117–163.

Marston, W. M. (1938). The lie detector test. New York: R. R. Smith.

Mathews, A., May, J., Mogg, K., & Eysenck, M. (1990). Attentional bias in anxiety: Selective search or defective filtering? Journal of Abnormal Psychology, 99, 166–173.

Matte, J. A. (1980). The Art and Science of the Polygraph Technique. Springfield, Ill.: Charles C. Thomas.

McCarthy, G. (1987, June). Generators of N200, N400 and P300. Paper presented at the Fourth International Conference on Cognitive Neuroscience. Paris-Dourdan, France.

McCarthy, G. & Donchin, E. (1981). A metric for thought: A comparison of P300 latency and reaction time. Science, 211, 77–80.

McCarthy, G., Wood, C. C., Williamson, P. D., & Spencer, D. (1989). Task-dependent field potentials in human hippocampal formation. The Journal of Neuroscience, 9, 4253–4268.

Mesulam, M. M. & Perry, J. (1972). The diagnosis of love-sickness: Experimental psychophysiology without the polygraph. Psychophysiology, 9, 546–550.

Mosso, A. (1896). Fear. E. Lough & F. Keisow (Transl.) (5th Edition). London, New York & Bombay: Longmans, Green and Co. Munsterberg, H. (1908). On the Witness Stand: Essays on Psychology and Crime. New York: The McClure Company.

Naatanen, R. (1969). Anticipation of relevant stimuli and evoked potentials: A comment on Donchin's and Cohen's 'Average evoked potentials and intramodality selective attention.' Perceptual and Motor Skills, 28, 639–646.

Naatanen, R. (1970). Evoked potential, EEG, and slow potential correlates of selective attention. Acta Pshchological Supplement, 33, 178–192.

Naatanen, R., & Picton, T. (1987). The N1 wave of the the human electric and magnetic response to sound: A review and an analysis of the component structure. Psychophysiology, 24, 375–425.

Neisser, U. (1982). Snapshots or benchmarks? In. Neisser, U. (Ed.), Memory Observed: Remembering in Natural Contexts (pp. 43–48). San Francisco: Freeman.

Nowlis, D. P. & Kamiya, J. (1970). The control of electroencephalographic alpha rhythms through auditory feedback and the associated mental activity. Psychophysiology, 6, 476–484.

Obrist, P. A., Webb, R. A.., Sutterer, J. R., & Howard, J. L. (1970). The cardiac-somatic relationship: Some reformations. Psychophysiology, 6, 569–587.

Office of Technology Assessment (1983). Scientific Validity of Polygraph Testing: A Research Review and Evaluation—A Technical Memorandum. Washington, D.C.: U.S. Government Printing Office.

Okada, Y. C., Kaufman, L., & Williamson, S. J. (1983). The hippocampal formation as a source of slow endogenous potentials. Electoencephalography and Clinical Neurophysiology, 55, 417–426.

Paller, K. A., Zola-Morgan, S., Squire, L. R., & Hillyard, S. A. (1988). P3-like brain waves in normal monkeys and in monkeys with medial temporal lesions. Behavioral Neuroscience, 102, 714–725.

Peters, D. P. (1988). Eyewitness memory and arousal in a natural setting. In M. M. Gruneberg, P. E. Morris, & R. N. Sykes (Eds.), Practical Aspects of Memory: Current Research and Issues, Vol 1: Memory in Everyday Life (pp. 89–94). Chichester: John Wiley:& Sons.

Pinneo, L., Johnson, P., & Mahoney, R. (1975). Biocybernetic approach to the detection of deception: a feasibility study. ,Polygraph, 4, (6), 311–313.

Plotkin, W. B. & Cohen, R. (1976). Occipital alpha and attributes of the "alpha experience." Psychophysiology, 13, 16–21.

Plutarch, D., first century A.D. (1952). In J. Dryden (Transl.), The Lives of the Noble Grecians and Romans (p. 741). Chicago: Encyclopaedia Britannica.

Podlesny, J. A. & Raskin, D.C. (1977). Physiological measures and the detection of deception. Psychological Bulletin, 84, 782–799.

Podlesny, J. A., & Raskin, D.C. (1978). Effectiveness of techniques and physiological measures in the detection of deception. Psychophysiology, 15, 344–358.

Porges, S. W. & Coles, M. G. H. (1976). Psychophysiology. Stroudsburg, Pa.: Dowden, Hutchinson, and Ross, Inc.

Pritchard, W. S. (1981). Psychophysiology of P300. Psychological Bulletin, 89, 506–540.

Putnam, L. E. & Roth, W. T. (1985). Automatic elicitation of P300 by high-intensity acoustic stimuli: A component of startle? Psychophysiology, 22, 610 (Abstract).

Raskin, D.C., (1976). Reliability of chart interpretation and sources of errors in polygraph examinations. Report No. 76-3 Contract 75-NI-0001. Salt Lake City, Utah: National Institute of Law Enforcement and Criminal Justice, Law Enforcement Assistance Administration, U.S. Department of Justice, Department of Psychology, University of Utah.

Raskin, D.C. (1978). Scientific assessment of the accuracy of detection of deception: A reply to Lykken. Psychophysiology, 15, 143–147.

Raskin, D.C. (1979). Orienting and Defensive Reflexes in the Detection of Deception. Hillsdale, N.J.: Lawrence Erlbaum, pp 587–605.

Raskin, D.C. (1986). The polygraph in 1986: Scientific, professional, and legal issues surrounding applications and acceptance of polygraph evidence. The Utah Law Review, 29–74.

Raskin, D.C. (1987). Methodological issues in estimating polygraphy accuracy in field applications. Special Issue: Forensic Psychology, Canadian Journal of Behavioral Science, 19, 389–404.

Raskin, D.C. (1988). Does science support polygraph research? In A. Gale (Ed.), The Polygraph Test: Lies, Truth and Science. London: Sage Publications.

Raskin, D.C. (1989). Polygraph techniques for the detection of deception. In D.C. Raskin (Ed.), Psychological Methods in Criminal Investigation and Evidence. New York: Springer Publishing Company.

Raskin, D.C. & Hare, R. D. (1978). Psychopathy and detection of deception in a prison population. Psychophysiology, 15, 126–136.

Raskin, D.C., Barland, G. H., & Podlesny, J. A. (1978). Validity and reliability of detection of deception. National Institute of Law Enforcement and Criminal Justice. Washington D.C.: U.S. Government Printing Office.

Raskin, D.C. & Podlesny, J. A. (1979). Truth and deception: A reply to Lykken. Psychological Bulletin, 86, 54–59.

Reid, J. E. (1947). A revised questioning technique in lie-detection tests. Journal of Criminology Law and Criminology, 37, 542–547.

Reid, J. E. & Inbau, R. E. (1966). Truth and Deception: The Polygraph ("Lie Detector") Technique. Baltimore: Williams and Wilkins.

Reid, J. E. & Inbau, F. E. (1977). Truth and Deception—The Polygraph Technique (3rd Ed). Baltimore: The Williams and Wilkins Company.

Restorff, H. von. (1933). Uber die Wirkung von Bereichsbildungen im Spurenfeld. Psychologische Forschung, 18, 299–342.

Restorff, H. von. (1933). Uber die Wirkung von Bereichsbildungen im Spurenfeld. Psychologische Forschung, 18, 299–342.

Richardson, J. R. (1963). Scientific Evidence for Police Officers. Cincinnati: The W. H. Anderson Company.

Rohrbaugh, J. W. & Gaillard, A. W. K. (1983). Sensory and motor aspects of the contingent negative variation. In A. K. W. Gaillard & W. Ritter (Eds.), Tutorials in Event-related Potential Research: Endogenous Components (pp. 269–310). Amsterdam: North-Holland.

Rosenfeld, J.P, Angell, A., Johnson. M., & Qian, J. (1991). An ERP-based, control-question lie detector analog: Algorithms for discriminating effects within individuals' average waveforms. Psychophysiology, 28, 319–335.

Rosenfeld, J.P., Nasman, V. T., Whalen, R., Cantwell, B., & Mazzeri, L. (1987). Late vertex positivity in event-related potentials as a guilty knowledge indicator: A new method of lie detection. International Journal of Neuroscience, 34, 125–129.

Rosler, F. (1983). Endogenous ERPs and cognition: Probes, prospects, and pitfalls in matching pieces of the mind-body problem. In A. W. K. Galliard, & W. Ritter (Eds.), Tutorials in Event-related Brain Potential Research: Endogenous Components (pp. 9–35). Amsterdam: Elsevier.

Rosler, F. (1988). A saddle made for a one-humped dromedary will fit only loosely to the back of a two-humped camel. Behavioral and Brain Sciences, 11, 390–391.

Rosler, F., Borgstedt, J., & Sojka, B. (1985). When perceptual or motor sets are changed: effects of updating demands on structure and energy of P300. Acta Psychologica, 60, 293–321.

Rovner, L. I., Raskin, D.C., & Kircher, J. C. (1978). Effects of information and practice on detection of deception. Psychophysiology, 16, 197.

Rubin, D.C. (1982). On the retention function for autobiographical memory. Journal of Verbal Learning and Verbal Behavior. 21, 21–38.

Rubin, D.C. (Ed.) (1986). Autobiographical Memory. Cambridge: Cambridge University Press.

Rubin, D.C., & Kozin, M. (1984). Vivid memories. Cognition, 16, 81–95.

Saxe, L., Dougherty, D., & Cross, T. (1985). The validity of polygraph testing: Scientific analysis and public controversy. American Psychologist, 40, 355–366.

Schneider, W., & Schiffrin, R. M. (1977). Controlled and automatic human information processing: I. Detection, search, and attention. Psychological Review, 84, 1–66.

Schwartz, G. E. (1986). Emotion and psychophysiological organization: A systems approach. In M. G. H. Coles, E. Donchin, & S. W. Porges (Eds.), Psychophysiology: Systems, Processes, and Applications (pp. 354–377). New York: Guilford Press.

Schwartz, G. E., Weinberger, D. A., & Singer, J. A. (1981). Cardiovascular differentiation of happiness, sadness, anger, and fear following imagery and exercise. Psychosomatic Medicine, 43, 343–364.

Selling, K. S. (1938). The medico-legal aspects of the polygraph or "lie detector". Journal of the Michigan State Medical Society, 37, 897–901.

Shaw, J. C., Foley, J., & Blowers, G. H. (1970). Alpha rhythm: An artifact? Lancet, I, 1173.

Silberman, E. K. & Weingartner, H. (1986). Hemispheric lateralization of functions related to emotion. Brain and Cognition, 5, 322–353.

Simson, R., Vaughan, H. G., & Ritter, W. (1976). The scalp topography of potentials associated with missing visual and auditory stimuli. Eleotroenoephalography and Clinical Neurophysiology, 40, 33–42.

Sirevaag, E. J., Kramer, A. F., Coles, M. G. H., & Donchin, E. (1989). Resource reciprocity: an event-related brain potentials analysis. Acta Psychologica, 70, 77–97.

Skolnick, J. H. (1961). Scientific theory and scientific evidence: An analysis of lie-detection. The Yale Law Journal, 70, 694–728.

Slowick, S. M. & Buckley, J. P. (1975). Relative accuracy of polygraph examiner diagnosis of respiration, bolld pressure, and GSR recordings. Journal of Police Science and Administration, 3, 305–309.

Smith, M. E., (1952). Childhood memories compared with those of adult life. Journal of Genetic Psychology, 80, 151–182.

Smith, M. E., Stapleton, J. M., & Halgren, E. (1986). Human medial temporal lobe potentials evoked in memory and language tasks. Electroencephalography and Clinical Neurophysiology, 63, 145–159.

Sokolov, E. N. (1969). The modeling properties of the nervous system. In I. Maltzman & K. Cole (Eds.), Handbook of Contemporary Soviet Psychology (pp. 671–704). New York: Basic Books.

Squires, K. C., Squires, N. K., & Hillyard, S. A. (1975). Decision-related cortical potentials during an auditory signal detection task with cued intervals. Journal of Experimental Psychology: Human Perception and Performance, 1, 268–279.

Squires, K. C., Wickens, C., Squires, N. K., & Donchin, E. (1976). The effect of stimulus sequence on the wave-form of the cortical event-related potential. Science, 193, 1142–1146.

Stern, R. M., Breen, J.P., Watanable, T., & Perry, B. S. (1981). Effect of feedback of physiological information on responses to innocent associations and guilty knowledge. Journal of Applied Psychology, 66, 677–681.

Summers, W. G. (1939). Science can get the confession. Fordham Law Review, 5, 334–354.

Sutton, S., Braren, M., Zubin, J., & John, E. R. (1965). Evoked-potential correlates of stimulus uncertainty. Science, 150, 1187–1188.

Sutton, S., Tueting, P., Zubin, J., & John, E. R. (1967). Information delivery and the sensory evoked potentials. Science, 155, 1436–1439.

Szucko, J. J. & Kleinmuntz, B. (1981). Statistical versus clinical lie detection. American Psychologist, 36, 488–496.

Taylor, P. J. & Kopelman, M.D. (1984). Amnesia for criminal offences. Psychological Medicine, 14, 581–588.

Towle, V. L., Heuer, D., & Donchin, E. (1980). On indexing attention and learning with event-related potentials. Psychophysiology, 17, 291.

Travis, T. A., Kondo, C. Y., & Knott, J. R. (1975). Subjective aspects of alpha enhancement. British Journal of Psychiatry, 127, 122–126.

Trovillo, P. V. (1939). A history of lie detection. Journal of Criminal Law and Criminology, 29, 848–881, & 30, 104.

Tucker, D. M. & Frederick, S. L. (1989). Emotion and brain lateralization. In H. Wagner & Manstead (Eds.), Handbook of Psychophysiology: Emotion and Social Behaviour (pp. 27–70). London: Wiley.

U.S. Central Intelligence Agency, Director of Central Intelligence (1982). Investigative scope and adjudicative procedures among intelligence community agencies: Personnel security survey. Cited in Office of Technology Assessment (1983). Scientific Validity of Polygraph Testing: A Research Review and Evaluation—A Technical Memorandum. Washington, D.C.: U.S. Government Printing Office.

Valerius Maximus, first century A.D. (1888). De parentum amore et indulgentia in liberos. In Carolus Kempf (Ed.), Factorum et Dictorum Memorabilium (Liber V, cap. vii) (pp. 260–262). Lipsiea: B. G. Tuebner. Vanderhoof, E. & Clancy, J. (1962). Peripheral blood flow as an indicator of emotional reaction. Journal of Applied Physiology, 17, 67–70.

Vaughan, H. G. & Arezzo, J. C. (1988). The neural basis of event-related potentials. In T. W. Picton (Ed.), Handbook of Electroencephalography and Clinical Neurophysiology: Human Event-related Potentials (Vol. 3, pp. 45–96). Amsterdam: Elsevier.

Verleger, R. (1988). Event-related potentials and cognition: A critique of the context updating hypothesis and an alternative interpretation of P3. Behavioral and Brain Sciences, 11, 343–56.

Wagenaar, W. A. (1986). My memory: A study of autobiographical memory over six years. Cognitive Psychology, 18, 225–252.

Walter, W. G, Cooper, R., Aldridge, V. J., McCallum, W. C., & Winter, A. L. (1964). Contingent negative variation: An electrical sign of sensorimotor association and expectancy in the human brain. Nature, 203, 380–384.

Wasserman, S. & Bockenholt, U. (1989). Bootstrapping: Applications to psychophysiology. Psychophysiology, 26, 208–221.

White, R. T. (1982). Memory for personal events. Human Learning, 1, 171–183.

Wickens, C., Isreal, J., & Donchin, E. (1977). The event-related cortical potential as an index of task workload. In A. S. Neal & R. F. Palasek (Eds.), Proceedings of the Human Factors Society 21st Annual Meeting. San Francisco, Calif.

Wicklander, D. E. & Hunter, F. L. (1975). The influence of auxiliary sources of information in polygraph diagnosis. Journal of Police Science and Administration, 3, 405–409.

Widacki, J. & Horvath, F. (1978). An experimental investigation on the relative validity and utility of the polygraph technique and three other common methods of criminal identification. Journal of Forensic Sciences, 23, 596–601.

Wise, T. A. (1845). Commentary on the Hindu System of Medicine (pp. 394, from Mitakshara Shastra). Calcutta, Ind.

Yee, C. M. & Miller, G. A. (1987). Affective valence and information processing. In R. Johnson, Jr., J. W. Rohrbaugh, & R. Parasuraman, Current Trends in Event-Related Potential Research (pp 300–307) (EEG Suppl. 40). Elsevier Science Publishers: B.V., Biomedical Division.

Yee, C. M. & Miller, G. A. (1988). Emotional information processing: Modulation of fear in normal and dysthymic. Journal of Abnormal Psychology, 97, 54.

TABLE 1

| | TYPES OF STIMULI AND PREDICTED ERPs | | | | |
|---|---|---|---|---|---|
| Stimulus Type | Relative Frequency | Description | Instructions | Stimulus Evaluation | Predicted ERP |
| Target | 1/6 | Relevant to Task | Right Button Press | Relevant, Rare | P300 |

TABLE 1-continued

TYPES OF STIMULI AND PREDICTED ERPs

| Stimulus Type | Relative Frequency | Description | Instructions | Stimulus Evaluation | Predicted ERP |
|---|---|---|---|---|---|
| Irrelevant (frequent) | 2/3 | Irrelevant to Task and Crime | Left Button Press | Irrelevant, Frequent | No P300 |
| Probe | 1/6 | Relevant to Crime | Left Button Press (Treat Like Irrelevant Stimuli) | If Innocent: Irrelevant, Frequent (Indistinguishable from Irrelevant Stimuli) | No P300 |
| | | | | If Guilty: Relevant, Rare | P300 |

TABLE 2

Table 2A: ACCURACY OF DETERMINATIONS, EXPERIMENT 1

| | Subject State | | |
|---|---|---|---|
| Decision | Guilty | Innocent | Total |
| Guilty | 18 | 0 | 18 |
| Innocent | 0 | 17 | 17 |
| Indeterminate | 2 | 3 | 5 |
| Total | 20 | 20 | 40 |

| Predictive Values | |
|---|---|
| Positive | Negative |
| 100% | 100% |

| | |
|---|---|
| Validity (excluding inconclusives) | 100% |
| Validity (including inconclusives) | 87.5% |

Table 2B: DETERMINATIONS, GUILTY CONDITION, EXPERIMENT 1

| Subject # | Determination | Statistical Confidence |
|---|---|---|
| 1 | Guilty | .00 |
| 2 | Guilty | .01 |
| 3 | Guilty | .02 |
| 4 | Guilty | .00 |
| 5 | Guilty | .00 |
| 6 | Guilty | .06 |
| 7 | Guilty | .00 |
| 8 | Guilty | .00 |
| 9 | Guilty | .00 |
| 10 | Guilty | .00 |
| 11 | Guilty | .00 |
| 12 | Guilty | .03 |
| 13 | Guilty | .01 |
| 14 | Guilty | .00 |
| 15 | Guilty | .02 |
| 16 | Indeterminate | .45 |
| 17 | Guilty | .03 |
| 18 | Guilty | .00 |
| 19 | Guilty | .00 |
| 20 | Indeterminate | .43 |

Table 2C: DETERMINATIONS, INNOCENT CONDITION, EXPERIMENT 1

| Subject # | Determination | Statistical Confidence |
|---|---|---|
| 1 | Innocent | .80 |
| 2 | Innocent | .95 |
| 3 | Indeterminate | .47 |
| 4 | Innocent | 1.00 |
| 5 | Innocent | 1.00 |
| 6 | Innocent | .98 |
| 7 | Innocent | .93 |
| 8 | Indeterminate | .36 |
| 9 | Innocent | 1.00 |
| 10 | Innocent | .99 |
| 11 | Innocent | .96 |
| 12 | Innocent | .91 |
| 13 | Innocent | 1.00 |
| 14 | Innocent | .83 |
| 15 | Innocent | 1.00 |
| 16 | Innocent | .96 |
| 17 | Innocent | 1.00 |
| 18 | Indeterminate | .46 |
| 19 | Innocent | 1.00 |
| 20 | Innocent | 1.00 |

TABLE 3

MANUAL RESPONSE TIMES (msec), EXPERIMENT 1

| Subject | Target | Probe | Irrelevant |
|---|---|---|---|
| INNOCENT CONDITION | | | |
| 1 | 918 | 775 | 775 |
| 2 | 1001 | 927 | 933 |
| 3 | 919 | 792 | 775 |
| 4 | 900 | 750 | 765 |
| 5 | 839 | 746 | 751 |
| 6 | 838 | 759 | 744 |
| 7 | 948 | 820 | 853 |
| 8 | 982 | 829 | 776 |
| 9 | 887 | 749 | 768 |
| 10 | 982 | 805 | 806 |
| 11 | 904 | 736 | 744 |
| 12 | 951 | 839 | 838 |
| 13 | 892 | 756 | 780 |
| 14 | 855 | 747 | 744 |
| 15 | 928 | 742 | 745 |
| 16 | 915 | 813 | 827 |
| 17 | 874 | 744 | 743 |
| 18 | 948 | 816 | 813 |
| 19 | 887 | 825 | 832 |
| 20 | 861 | 764 | 776 |
| Averages | 911 | 786 | 789 |
| GUILTY CONDITION | | | |
| 1 | 941 | 880 | 810 |
| 2 | 1061 | 1087 | 936 |
| 3 | 999 | 1031 | 880 |
| 4 | 937 | 877 | 762 |
| 5 | 863 | 784 | 730 |
| 6 | 906 | 808 | 762 |
| 7 | 965 | 911 | 835 |
| 8 | 906 | 847 | 773 |
| 9 | 1017 | 872 | 781 |
| 10 | 1146 | 1111 | 905 |
| 11 | 950 | 774 | 759 |
| 12 | 972 | 890 | 826 |
| 13 | 1033 | 991 | 842 |
| 14 | 871 | 767 | 739 |
| 15 | 977 | 869 | 779 |
| 16 | 944 | 869 | 831 |
| 17 | 920 | 792 | 769 |
| 18 | 965 | 833 | 792 |
| 19 | 927 | 933 | 850 |
| 20 | 857 | 785 | 774 |
| Averages | 957 | 885 | 806 |

TABLE 4

Table 4A: ACCURACY OF DETERMINATIONS, EXPERIMENT 2

| | Subject State | | |
|---|---|---|---|
| Decision | Guilty | Innocent | Total |

TABLE 4-continued

| | | | |
|---|---|---|---|
| Guilty | 4 | 0 | 4 |
| Innocent | 0 | 3 | 3 |
| Indeterminate | 0 | 1 | 1 |
| Total | 4 | 4 | 8 |

Predictive Values

| Positive | Negative |
|---|---|
| 100% | 100% |

| | |
|---|---|
| Validity (excluding inconclusives) | 100% |
| Validity (including inconclusives) | 87.5% |

Table 4B: DETERMINATIONS, GUILTY CONDITION, EXPERIMENT 2

| Subject # | Determination | Statistical Confidence |
|---|---|---|
| 1 | Guilty | .07 |
| 2 | Guilty | .03 |
| 3 | Guilty | .01 |
| 4 | Guilty | .02 |

Table 4C- DETERMINATIONS, INNOCENT CONDITION, EXPERIMENT 2

| Subject # | Determination | Statistical Confidence |
|---|---|---|
| 1 | Innocent | .99 |
| 2 | Indeterminate | .27 |
| 3 | Innocent | .96 |
| 4 | Innocent | 1.00 |

TABLE 5

Table 5A: ACCURACY OF DETERMINATIONS, EXPERIMENT 3

| | Subject State | | |
|---|---|---|---|
| Decision | Guilty | Innocent | Total |
| Guilty | 2 | 0 | 2 |
| Innocent | 0 | 4 | 4 |
| Indeterminate | 2 | 0 | 2 |
| Total | 4 | 4 | 8 |

Predictive Values

| Positive | Negative |
|---|---|
| 100% | 100% |

| | |
|---|---|
| Validity (excluding inconclusives) | 100% |
| Validity (including inconclusives) | 75% |

Table 5B: DETERMINATIONS, GUILTY CONDITION, EXPERIMENT 3

| Subject # | Determination | Statistical Confidence |
|---|---|---|
| 1 | Indeterminate | .14 |
| 2 | Guilty | .01 |
| 3 | Guilty | .00 |
| 4 | Indeterminate | .17 |

Table 5C: DETERMINATIONS, INNOCENT CONDITION, EXPERIMENT 3

| Subject # | Determination | Statistical Confidence |
|---|---|---|
| 1 | Innocent | .78 |
| 2 | Innocent | 1.00 |
| 3 | Innocent | .94 |
| 4 | Innocent | 1.00 |

TABLE 6

MANUAL RESPONSE TIMES (msec), EXPERIMENT 3

| Subject | Target | Probe | Irrelevant |
|---|---|---|---|
| | INNOCENT CONDITION | | |
| 1 | 959 | 774 | 791 |
| 2 | 972 | 725 | 775 |
| 3 | 1021 | 899 | 910 |
| 4 | 946 | 864 | 867 |
| Averages | 975 | 816 | 836 |
| | GUILTY CONDITION | | |
| 1 | 1043 | 973 | 865 |
| 2 | 880 | 913 | 889 |
| 3 | 1130 | 1050 | 973 |
| 4 | 1010 | 943 | 856 |

TABLE 6-continued

MANUAL RESPONSE TIMES (msec), EXPERIMENT 3

| Subject | Target | Probe | Irrelevant |
|---|---|---|---|
| Averages | 1016 | 970 | 896 |

I claim:
1. A method of detecting concealed information stored in a human brain of a subject, which information is not including affiliation with a particular group of people, familiarity with a particular realm of knowledge, or expertise in a particular field, comprising:
   a) Informing said subject of stimuli to be presented that are relevant to said class;
   b) Presenting to said subject in oddball series said relevant stimuli of step (a) and stimuli irrelevant to said class, and Target stimuli requiring said subject to perform a task;
   c) Recording electrical brain activity subsequent to the presentation of each of said stimuli for determining corresponding event related brain potential responses; and
   d) Comparing the responses to the relevant and Target stimuli, and to the relevant and irrelevant stimuli for determining knowledge or lack of knowledge, respectively, of said relevant stimuli in said subject.

2. The method according to claim 1 wherein the subject performs a reaction time task in response to each stimulus during step (b).

3. A method of detecting whether or not someone is telling the truth, comprising:
   a) asking questions of the individual;
   b) noting the individual's answers;
   c) asking the individual, in addition to the answers to the questions, to report continuously in a stream-of-consciousness fashion, on their ongoing thought processes;
   d) measuring electrical brain activity during said thought processes; and
   e) comparing the electrical brain activity to standards for activity when a subject is known to be accurately reporting on his/her spontaneous mental activity and for activity when an individual is known to be speaking something that is at variance with his ongoing mental activity.

4. A method of detecting whether a subject is telling the truth comprising:
   (a) asking questions of the subject and asking the subject to report continuously in a stream-of-consciousness fashion on his/her spontaneous mental thoughts,
   (b) recording electrical brain activity during step (a), and
   (c) comparing the electrical brain activity to standards for activity when a subject is known to be accurately reporting his/her spontaneous mental thoughts and for activity when a subject is known not to be reporting his/her spontaneous mental thoughts.

5. A method of detecting information stored in a brain of a subject comprising:
   presenting to said subject in oddball series stimuli including:
   Probe stimuli relevant to a specific situation under investigation for effecting in said subject an event related brain potential when said subject has knowledge thereof:
Irrelevant stimuli not relevant to said situation; and
Target stimuli identified to said subject as being noteworthy, and in response to which said subject is instructed to perform a task, said Target stimuli like said Probe stimuli being relevant to said situation under investigation;
detecting an electrical brain response from said subject in response to each of said stimuli;
analyzing said electrical brain responses for uncovering said event related brain potential therein; and
comparing said electrical brain responses from said Probe stimuli with said Target stimuli for determining whether said subject recognizes said Probe stimuli, and comparing said Probe stimuli with said Irrelevant stimuli for determining whether said subject does not recognize said Probe stimuli.

6. The method in claim 5 wherein the subject is required to perform a reaction time task in response to each stimulus, distinguishing between Target stimuli of which he has been informed by the researcher and Probe and Irrelevant stimuli of which he has not been so informed, the subject performing a first task for the former, and a second, different task for the latter.

7. The method in claim 6 wherein said event related brain potential, is an electrically positive P300 component, and the comparison is on the basis of said P300 component.

8. The method in claim 5 wherein the analysis and comparison steps include:
a) iteratively sampling from the known relevant Probe, unknown relevant Target, and irrelevant stimuli, with replacement, with a sample size in each case equal to the total number of trials of that type in the original data;
b) averaging the samples of each trial type in each iteration;
c) repeatedly, once each iteration, comparing the average unknown relevant Probe brain response with the average known relevant Target brain response and the average irrelevant response;
d) tallying the times that the unknown relevant Probe response is more similar to the Irrelevant brain response than to the known relevant Target brain response; and
e) comparing the tally with a criterion to determine whether the subject is "guilty"(knowledgeable) or "innocent" (not knowledgeable).

9. The method in claim 8 wherein the comparison step includes correlation.

10. The method in claim 9 wherein the grand average waveform is subtracted from each of the averages before computing the correlation.

11. The method in claim 8 wherein the comparison step includes one of:
a) comparing area, defined as the sum of the points in the time range of the P300;
b) comparing base to peak, defined as the most positive point in the time range of the P300, minus the average of the points in the baseline prior to the stimulus onset; and
c) comparing peak to peak, defined as the most positive point in the time range of the P300, minus the most negative point post-stimulus and prior to the time range of the P300.

12. The method in claim 5 wherein:
a) the comparisons of the electrical brain responses for the Probe, target, and Irrelevant stimuli are computed on the basis of a single average of each type, without iterative sampling; and
b) the results of the comparisons of single averages are compared with criteria for determining whether the subject does or does not recognize the Probe stimuli.

13. The method in claim 12 wherein differences and ratios of each of the comparisons of each of the trial types are also computed.

14. The method in claim 13 wherein the results of the different comparisons are combined using multiple regression.

15. The method in claim 5 wherein reaction times in performing the first and second tasks are determined and analyzed for determining recognition of said Probe stimuli.

16. The method in claim 5 wherein the comparison step provides a single index, which is then compared with a criterion to determine whether the subject is "innocent" or "guilty."

17. A method according to claim 5 wherein said information stored in said subject brain regards a particular event, and both said Probe and Target stimuli are relevant to said event whereas said Irrelevant stimuli are not.

18. A method according to claim 5 wherein said information stored in said subject brain does not regard a particular event but rather is indicative of a class including affiliation with a particular group, familiarity with a particular realm of knowledge, or expertise in a particular field, and wherein said Probe stimuli are known to said class and unknown outside said class.

19. A method of detecting information stored in a brain of a subject comprising:
presenting to said subject stimuli including:
rare, Target stimuli identified to said subject as being noteworthy, and in response to which said subject is instructed to perform a task; and
frequent, non-Target stimuli including Probe stimuli preselected as being possibly relevant to a situation under investigation, and Irrelevant stimuli not relevant to said situation;
detecting an electrical brain response from said subject in response to each of said stimuli;
analyzing said electrical brain responses for uncovering any event related brain potentials; and
comparing said electrical brain responses for each of said non-Target stimuli with other non-Target stimuli and with said Target stimuli for uncovering an event related brain potential due to said non-Target stimuli which is similar to an event related brain potential for said Target stimuli and in contrast to non-Target stimuli not eliciting an event related brain potential.

20. A method according to claim 19 wherein said event related brain potential is a P300 component.

21. A method according to claim 20 wherein said non-Target stimuli include multiple choice stimulus sets for eliciting said P300 component in response to one stimulus of each set.

22. A headband for measurement of electrical brain activity from a scalp of a subject, said scalp having frontal, central, parietal, left mastoid, and right mastoid locations, said headband comprising:
a flexible band having first and second opposite ends and a center portion therebetween, and being sized to surround said scalp for joining together said first and second ends;

a flexible overflap having first and second opposite ends, with said overflap first end being integrally joined to said band center portion, and being sized to extend over said scalp frontal, central, and parietal locations for joining together said overflap second end to said band first and second ends;

first means for releasably joining together said band first and second ends;

second means for releasably joining together said overflap second end with said joined together band first and second ends;

a plurality of spaced-apart female electrode sites fixedly joined to said band and to said overflap for alignment with said scalp frontal, central, parietal, left mastoid, and right mastoid locations upon placement of said headband on said subject scalp; and a plurality of electrode wires joined to respective ones of said electrode sites.

23. A headband according to claim 22 wherein said electrode wires extend from said electrode sites and internally through said overflap, and have proximate ends joined to a connector disposed adjacent to said overflap second end.

24. A headband according to claim 22 wherein said first and second joining means include complementary pairs of Velcro hook and loop pads joined to said band and overflap.

25. A headband according to claim 22 wherein said electrode sites for said frontal, central, and parietal scalp location are disposed along said overflap, and said electrode sites for said left and right mastoid locations are disposed along said band.

26. A headband according to claim 22 further comprising:

a flexible secondary crossbar attached to said overflap at an intermediate portion thereof and disposed generally parallel to said band, said secondary crossbar having first and second opposite distal ends; and wherein said electrode sites for said frontal, central, and parietal scalp locations are disposed along said overflap, and said electrode sites for said left and right mastoid locations are disposed along said secondary crossbar adjacent to said first and second ends thereof, respectively; and further wherein said secondary crossbar is sized for positioning said first and second ends thereof underneath said band when said band and overflap are positioned over said subject scalp.

27. A headband according to claim 26 wherein said secondary crossbar is attached to said overflap at said electrode site for said parietal scalp location, and said electrode sites for said left mastoid, parietal, and right mastoid locations are colinearly spaced apart along said secondary crossbar.

28. A headband according to claim 22 further comprising:

a plurality of spaced apart flaps fixedly joined at one edge thereof to said band and said overflap; and third means for releasably joining together each of said flaps with respective ones of said band and said overflap so that each of said flaps is individually repositionable on said band and said overflap.

29. A headband according to claim 28 wherein each of said flaps is disposed on said band and said overflap behind a respective one of said electrode sites for adjusting mobility thereof.

30. A headband according to claim 29 wherein:

said first and second joining means include complementary pairs of Velcro hook and loop pads joined to said band and overflap; and said third joining means include complementary pairs of Velcro hook and loop pads joined to said flaps and said band and overflap.

31. A headband according to claim 22 including a plurality of electrodes removably affixed to respective ones of said female electrode sites.

* * * * *